US009829698B2

United States Patent
Haraguchi et al.

(10) Patent No.: US 9,829,698 B2
(45) Date of Patent: Nov. 28, 2017

(54) ENDOSCOPE

(71) Applicant: PANASONIC CORPORATION, Osaka (JP)

(72) Inventors: Naoyuki Haraguchi, Saga (JP); Takafumi Sanada, Fukuoka (JP); Yasuyuki Hanada, Fukuoka (JP); Yuichi Hatase, Fukuoka (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 15/240,706

(22) Filed: Aug. 18, 2016

(65) Prior Publication Data
US 2017/0059848 A1 Mar. 2, 2017

(30) Foreign Application Priority Data

Aug. 31, 2015 (JP) .................................. 2015-171553
Aug. 31, 2015 (JP) .................................. 2015-171557
(Continued)

(51) Int. Cl.
*G02B 23/24* (2006.01)
*A61B 1/00* (2006.01)
(Continued)

(52) U.S. Cl.
CPC .......... *G02B 23/243* (2013.01); *A61B 1/0011* (2013.01); *A61B 1/00018* (2013.01);
(Continued)

(58) Field of Classification Search
CPC .............. G02B 23/243; G02B 23/2848; H04N 5/2256; A61B 1/0011; A61B 1/00114;
(Continued)

(56) References Cited

U.S. PATENT DOCUMENTS 7,116,486 B2 10/2006 Forkey et al.
7,561,351 B2 7/2009 Konno
(Continued)

FOREIGN PATENT DOCUMENTS

CN 101133934 A 3/2008
CN 101183169 A 5/2008
(Continued)

OTHER PUBLICATIONS

English Translation of the First Office Action, dated May 22, 2016, for corresponding Chinese Application No. 201610772959.6, 11 pages.
(Continued)

*Primary Examiner* — Timothy J Neal
(74) *Attorney, Agent, or Firm* — Seed IP Law Group LLP

(57) ABSTRACT

An endoscope includes a single lens that has a square exterior shape in a direction perpendicular to an optical axis, an image sensor that has an square exterior shape which is same as the exterior shape of the single lens, in the direction perpendicular to the optical axis, a sensor cover that has an exterior shape which is same as the exterior shape of the single lens, in the direction perpendicular to the optical axis; and a bonding resin portion that fixes the sensor cover to the single lens, The single lens is a lens which is formed in a prismatic shape. The single lens has first surface on an imaging subject side that has a plane, and has second surface on an imaging side that has a convex surface.

9 Claims, 35 Drawing Sheets

(30) Foreign Application Priority Data

Aug. 31, 2015 (JP) ................................ 2015-171558
Apr. 5, 2016 (JP) ................................ 2016-076173

(51) Int. Cl.

| | |
|---|---|
| A61B 1/05 | (2006.01) |
| A61B 1/07 | (2006.01) |
| A61B 1/04 | (2006.01) |
| A61B 1/06 | (2006.01) |
| H04N 5/225 | (2006.01) |
| A61B 1/307 | (2006.01) |

(52) U.S. Cl.

CPC .......... *A61B 1/00096* (2013.01); *A61B 1/051* (2013.01); *A61B 1/0607* (2013.01); *A61B 1/07* (2013.01); *G02B 23/2469* (2013.01); *G02B 23/2484* (2013.01); *H04N 5/2253* (2013.01); *A61B 1/0676* (2013.01); *A61B 1/0684* (2013.01); *A61B 1/307* (2013.01); *H04N 2005/2255* (2013.01)

(58) Field of Classification Search

CPC ... A61B 1/00135; A61B 1/051; A61B 1/0684; A61B 1/07

See application file for complete search history.

(56) References Cited

U.S. PATENT DOCUMENTS

| | | |
|---|---|---|
| 8,355,216 B2 | 1/2013 | Orihara et al. |
| 8,803,960 B2 | 8/2014 | Sonnenschein et al. |
| 9,329,740 B2 | 5/2016 | Chao et al. |
| 2005/0083581 A1 | 4/2005 | Forkey et al. |
| 2006/0262415 A1 | 11/2006 | Forkey et al. |
| 2008/0055748 A1 | 3/2008 | Konno |
| 2008/0117292 A1 | 5/2008 | Orihara et al. |
| 2009/0173875 A1 | 7/2009 | Ichimura et al. |
| 2010/0085466 A1 | 4/2010 | Fujimori et al. |
| 2011/0063428 A1 | 3/2011 | Sonnenschein et al. |
| 2013/0038948 A1 | 2/2013 | Okai |
| 2013/0329026 A1 | 12/2013 | Hida et al. |
| 2014/0320621 A1 | 10/2014 | Sonnenschein et al. |
| 2014/0346322 A1 | 11/2014 | Fujimori et al. |
| 2015/0029138 A1 | 1/2015 | Chao et al. |
| 2015/0238069 A1 | 8/2015 | Osada et al. |

FOREIGN PATENT DOCUMENTS

| | | |
|---|---|---|
| CN | 101517448 A | 8/2009 |
| CN | 102955219 A | 3/2013 |
| JP | 11-076156 A | 3/1999 |
| JP | 2000-037343 A | 2/2000 |
| JP | 2001-128930 A | 5/2001 |
| JP | 2007-504892 A | 3/2007 |
| JP | 2010-091986 A | 7/2012 |
| JP | 2012-139308 A | 7/2012 |
| JP | 2013-504400 A | 2/2013 |
| JP | 2014-089334 A | 5/2014 |
| JP | 2015-026375 A | 2/2015 |
| JP | 2015-045837 A | 3/2015 |
| JP | 2015-058118 A | 3/2015 |
| JP | 2015-073540 A | 4/2015 |
| JP | 2015-127741 A | 7/2015 |
| WO | 2013/031276 A1 | 3/2013 |
| WO | 2013/146091 A1 | 10/2013 |
| WO | 2014/034839 A1 | 3/2014 |

OTHER PUBLICATIONS

Japanese Office Action dated Dec. 8, 2015, for corresponding JP Application No. 2015-171553, 2 pages.
Japanese Office Action dated Dec. 8, 2015, for corresponding JP Application No. 2015-171557, 2 pages.
Japanese Office Action dated Dec. 8, 2015, for corresponding JP Application No. 2015-171558, 3 pages.

*FIG. 10*

|  | NO ADDING | ADDING 1 wt% | ADDING 5 wt% |
|---|---|---|---|
| RESISTANCE VALUE Ω/cm | $1.8 \sim 5.0 \times 10^{13}$ | $2.5 \sim 3.0 \times 10^{13}$ | $3.5 \sim 5.0 \times 10^{10}$ |
| LIGHT BLOCKING RATE (THIKNESS 50 μm) | — | 95% OR GREATER | 99% OR GREATER |

ENDOSCOPE

BACKGROUND

1. Technical Field

The present invention relates to an endoscope.

2. Description of the Related Art

In the related art, an endoscope for imaging an internal state of a patient's body, and an interior of a device or a structure has been widely used in a medical field or an industrial field. In the endoscope of this type, in an insertion part inserted into an observation target, light from an imaging site is received by an objective lens system so as to form an image on a light-receiving surface of an image sensor. The endoscope converts imaging forming light into an electrical signal, and transmits the electrical signal as a video signal to an external image processing apparatus via a signal cable.

For example, as for the endoscope used in the medical field, in order to reduce the burden of a surgical target person, it is important to further reduce an exterior diameter of the insertion part on a distal side inserted into a body of the surgical target person. In the related art, an oral endoscope with a normal diameter has the maximum exterior diameter of approximately 8 to 9 mm. Therefore, in some cases, the oral endoscope is likely to touch a tongue's root when being inserted, thereby causing the surgical target person to suffer nausea or a feeling of dyspnea. Therefore, in recent years, a small-diameter nasal endoscope has been rapidly and widely used. The small-diameter nasal endoscope has the maximum exterior diameter of approximately 5 to 6 mm, which is approximately half the maximum exterior diameter of the oral endoscope in the related art. Accordingly, the small-diameter nasal endoscope enables nasal insertion. The small-diameter nasal endoscope is as thin as approximately 5 mm, thereby inducing less vomiting reflex. In many cases, the surgical target person does not worry about the insertion too much.

For example, an electronic endoscopic system 501 disclosed in the WO2013/031276 illustrated in FIG. 33 is configured to mainly include an endoscope 503, a light source device 505, a video processor 507, and a monitor 509. The endoscope 503 is configured to have an elongated and thin insertion part 511, an operation unit 513, and a universal cable 515 serving as an electric cable. The insertion part 511 of the endoscope 503 is configured to have a distal portion 517, a bending portion 519, and a flexible tube portion 521, sequentially from a distal side inserted into the surgical target person. The operation unit 513 is configured to have an operation unit main body 523 and a surgical instrument channel insertion portion 525 through which various surgical instruments are inserted into the insertion part 511. A bending operation knob 527 for causing the bending portion 519 to perform a bending operation is arranged in the operation unit main body 523. The bending operation knob 527 includes a UD bending operation knob 529 for causing the bending portion 519 to perform the bending operation in a vertical direction, and an RL bending operation knob 531 for causing the bending portion 519 to perform the bending operation in a lateral direction.

In an endoscope 533 disclosed in WO2013/146091 illustrated in FIG. 34, a distal portion thereof is provided with an exterior cylinder 535. An imaging mechanism 539 covered with a filling light blocking material 537 is disposed in the exterior cylinder 535. The imaging mechanism 539 includes an image sensor 543 that has a light-receiving portion 541 on one surface, a cover member 545 that covers the surface on which the light-receiving portion 541 of the image sensor 543 is disposed, a lens unit 547 that is optically coupled to the light-receiving portion 541 of the image sensor 543, and a flexible printed wiring board 549. From an object side, the lens unit 547 has an objective cover member 551, an iris 553, a plano-convex lens 555, a plano-convex lens 557, and a lens barrel 559 for fixing all of these. An adhesive 561 fixes a section between the plano-convex lens 557 and the cover member 545.

Incidentally, an endoscope needs to have a further reduced exterior diameter (for example, a reduced exterior diameter of an insertion part which is a distal side of WO2013/031276 or an object side of WO2013/146091). The reason is based on a medical demand to observe internal details by inserting a new endoscope other than the above-described existing small-diameter nasal endoscope into a site where the existing small-diameter nasal endoscope is less likely to be inserted into a body of a surgical target person (for example, vessels or holes having very small diameter, such as blood vessels).

However, it is presumed that the endoscope 503 disclosed in WO2013/031276 is mainly inserted into a digestive organ of a human body from a viewpoint of an external shape illustrated in FIG. 1 of WO2013/031276 and a described application example (for example, the insertion part 511 for being inserted into an upper or lower digestive organ of a living body is a so-called flexible endoscope). Therefore, it is difficult to observe the inside of the human body by inserting the endoscope 503 into vessels or holes having very small diameter, for example, such as blood vessels of the human body.

In the endoscope 533 disclosed in WO2013/146091, the image sensor 543 and the flexible printed wiring board 549 are larger than an exterior diameter of the lens barrel 559 in a radial direction in the imaging mechanism 539. Additionally, the endoscope 533 is configured so that the imaging mechanism 539 having these members is accommodated in the exterior cylinder 535, and so that the imaging mechanism 539 is covered with the light blocking material 537 filling the exterior cylinder 535. Therefore, a distance of the image sensor 543 and the flexible printed wiring board 549 which protrude outward from the lens barrel 559 in the radial direction, and a thickness of the exterior cylinder 535 lead to a disadvantageous structure in miniaturizing the endoscope 533. Since the exterior cylinder 535 is required, the number of components increases, and the cost increases.

BRIEF SUMMARY

The present invention has an object to provide an endoscope with a reduced size (for example, the thinning of the exterior diameter of a distal insertion part) and a reduced cost.

According to an aspect of the present invention, there is provided an endoscope having a single lens that has a square exterior shape in a direction perpendicular to an optical axis, an image sensor that has an square exterior shape which is same as the exterior shape of the single lens, in the direction perpendicular to the optical axis, a sensor cover that covers an imaging area of the image sensor, and has an exterior shape which is same as the exterior shape of the single lens, in the direction perpendicular to the optical axis, and a bonding resin portion that fixes the sensor cover to the single lens, the optical axis of the single lens coinciding with a center of the imaging area. The image sensor has one side whose length is 0.5 mm or smaller. The single lens is a lens which is formed in a prismatic shape, and whose first surface on an imaging subject side has a plane and whose second surface on an imaging side has a convex surface. A central portion of the single lens has a convex curved surface which protrudes in a substantially spherical shape configuring a lens surface of the convex surface on the imaging side. A peripheral edge portion of the single lens has a planar end surface, and has a bonding plane with the sensor cover over an entire area of the planar end surface.

According to an aspect of the present invention, there is provided an endoscope having an image sensor that is disposed in a distal portion of an insertion portion, and whose imaging area is covered with a sensor cover, a single lens that has a square exterior shape in a direction perpendicular to an optical axis, and a bonding resin portion that fixes the single lens and the sensor cover glass. The single lens is a lens which is formed in a prismatic shape, and whose first surface on an imaging subject side has a plane and whose second surface on an imaging side has a convex surface. A central portion of the single lens has a convex curved surface which protrudes in a substantially spherical shape configuring a lens surface of the convex surface on the imaging side. A peripheral edge portion of the single lens has a planar end surface, and has a bonding plane with the sensor cover glass over an entire area of the end surface. The peripheral edge portion of the single lens has an inclined portion which is tapered so as to be inclined from the planar end surface to the lens surface of the convex surface.

According to the present invention, it is possible to provide a miniaturized and cost-reduced endoscope.

BRIEF DESCRIPTION OF THE SEVERAL VIEWS OF THE DRAWINGS

FIG. 10 is a view illustrating an example of a relationship among the additive adding amount, a resistance value, and a light blocking rate in the molded part.

DETAILED DESCRIPTION

Hereinafter, appropriately with reference to the drawings, each embodiment in which an endoscope according to the present invention is specifically disclosed will be described in detail. However, in some cases, detailed description more than necessary may be omitted. For example, in some cases, detailed description of well-known items or repeated description of substantially the same configurations may be omitted. The reason is to facilitate the understanding of those skilled in the art by avoiding the following description from being unnecessarily redundant. The accompanying drawings and the following description are provided in order for those skilled in the art to fully understand the present disclosure, and these are not intended to limit the gist disclosed in the scope of claims.

First, a basic configuration example common to the endoscope according to each embodiment will be described. The configuration example means a configuration requirement in which the endoscope according to the present invention can be included therein. The endoscope according to the present invention does not exclude that respective configuration examples described below are included therein by overlapping each other.

First Embodiment

Basic Configuration Example

Figure 1:
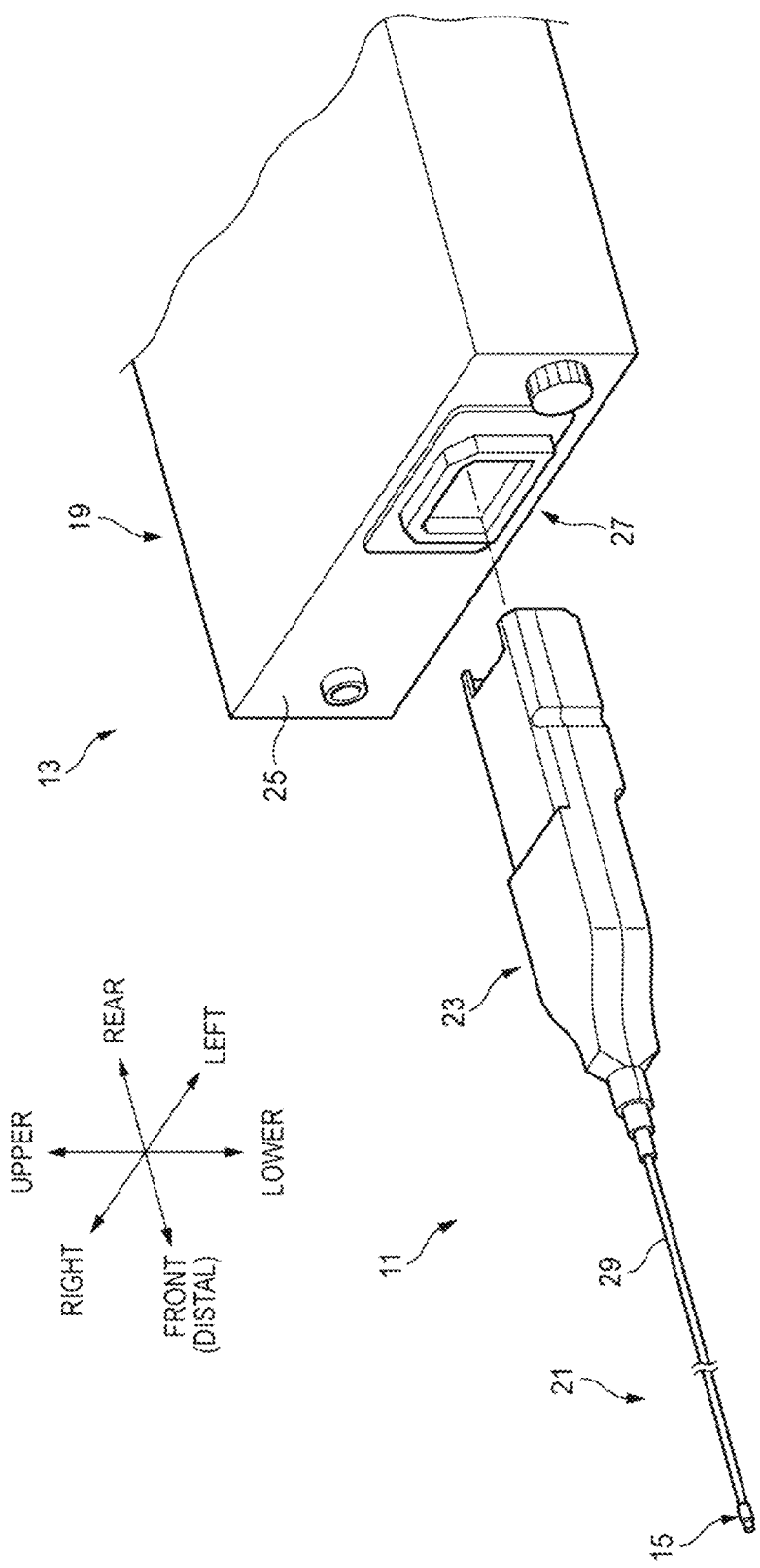
FIG. 1 is an overall configuration diagram illustrating an example of an endoscopic system using an endoscope according to each embodiment.

FIG. 1 is an overall configuration diagram illustrating an example of an endoscopic system using the endoscope according to each embodiment. FIG. 1 illustrates a perspective view of an overall configuration of an endoscopic system 13 including an endoscope 11 and a video processor 19.

A direction used for description herein is indicated in accordance with description of a direction in each drawing. Here, "up" and "down" respectively correspond to a top and a bottom of the video processor 19 placed on a horizontal plane. "Front (distal)" and "rear" respectively correspond to a distal side of an insertion part 21 of an endoscope main body (hereinafter, referred to as the "endoscope 11") and a proximal side of a plug part 23 (in other words, the video processor 19 side).

As illustrated in FIG. 1, for example, the endoscopic system 13 is configured to include the endoscope 11 serving as a medical flexible endoscope, and the video processor 19 which performs known image processing on a still image or a moving image obtained by imaging the inside of an observation target (for example, a blood vessel of a human body). The endoscope 11 includes the insertion part 21 which extends in a substantially longitudinal direction and is inserted into the observation target, and the plug part 23 to which a rear portion of the insertion part 21 is connected.

The video processor 19 has a socket portion 27 which is open on a front wall 25. A rear portion of the plug part 23 of the endoscope 11 is inserted into the socket portion 27, thereby enabling the endoscope 11 to transmit or to receive power and various signals (video signals and control signals) to or from the video processor 19.

The above-described power and various signals are introduced from the plug part 23 to a flexible portion 29 via a transmission cable 31 (refer to FIG. 3 or 4) inserted into the flexible portion 29. Image data output from an image sensor 33 disposed in a distal portion 15 is transmitted from the plug part 23 to the video processor 19 via the transmission cable 31. The video processor 19 performs known image processing such as color correction and gradation correction on the image data transmitted from the plug part 23, and outputs the image data subjected to image processing to a display device (not illustrated). For example, the display device is a monitor device having a display device such as a liquid crystal display panel. The display device displays an image of an imaging subject which is captured by the endoscope 11 (for example, image data indicating intravascular conditions of a person who is the imaging subject).

The insertion part 21 has the flexible portion 29 whose rear end is connected to the plug part 23, and the distal portion 15 extending to a distal end of the flexible portion 29. The flexible portion 29 has a suitable length corresponding to a method of various endoscopic inspections and endoscopic surgeries. For example, the flexible portion 29 is configured so that an exterior periphery of a helically wounded metal sheet is covered with a net and the exterior periphery is further coated, and is formed so has to have sufficient flexibility. The flexible portion 29 connects the distal portion 15 and the plug part 23 to each other.

Endoscopes 11 and 111 according to the respective embodiments described below can be inserted into a small-diameter body lumen by being formed so as to have a small diameter. Without being limited to blood vessels of a human body, the small-diameter body lumen includes ureters, pancreatic tubes, bile ducts, and bronchioles, for example. That is, the endoscopes 11 and 111 can be inserted into the blood vessels, the ureters, the pancreatic tubes, the bile ducts, and the bronchioles of the human body. In other words, the endoscopes 11 and 111 can be used in order to observe intravascular lesions. The endoscopes 11 and 111 are effectively used in identifying atherosclerotic plaques. In addition, the endoscopes 11 and 111 are also applicable to observation using the endoscope at the time of a cardiac catheter test. Furthermore, the endoscopes 11 and 111 are effectively used in detecting a thrombus or an arteriosclerotic yellow plaque. In a case of arteriosclerotic lesions, a color tone (white, pale yellow, or yellow) or a surface (smooth, irregular) is observed. In a case of the thrombus, a color tone (red, white, dark red, yellow, brown, or mixed color) is observed.

The endoscopes 11 and 111 can be used in diagnosing and treating a cancer of the renal pelvis and the ureter. In this case, the endoscopes 11 and 111 are inserted into the bladder through the urethra, and are moved forward into the ureter. In this manner, it is possible to observe the inside of the ureter and the renal pelvis.

The endoscopes 11 and 111 can be inserted into a Vater's papilla which is open in the duodenum. Bile is made in the liver, and passes through the bile duct. Pancreatic juice is made in the pancreas, passes through the pancreatic duct, and is discharged from the Vater's papilla located in the duodenum. The endoscopes 11 and 111 can be inserted through the Vater's papilla serving as an opening of the bile duct and the pancreatic duct, and can observe the bile duct and the pancreatic duct.

Furthermore, the endoscopes 11 and 111 can be inserted into the bronchus. The endoscopes 11 and 111 are inserted through an oral cavity or a nasal cavity of a test body (that is, a surgical target person) located at a face-up position. The endoscopes 11 and 111 are inserted into the bronchus while the vocal chord is visibly checked after passing through the pharynx and the larynx. The bronchus becomes thinner each time the bronchus is bifurcated. For example, according to the endoscopes 11 and 111 whose maximum exterior diameter Dmax is smaller than 2 mm, it is possible to check the lumen up to the sub-segmental bronchus.

Next, various configuration examples belonging to the endoscope according to the first embodiment will be described. The endoscope 11 according to each embodiment can adopt each configuration from a first configuration example to a twenty fourth configuration example.

Figure 2:
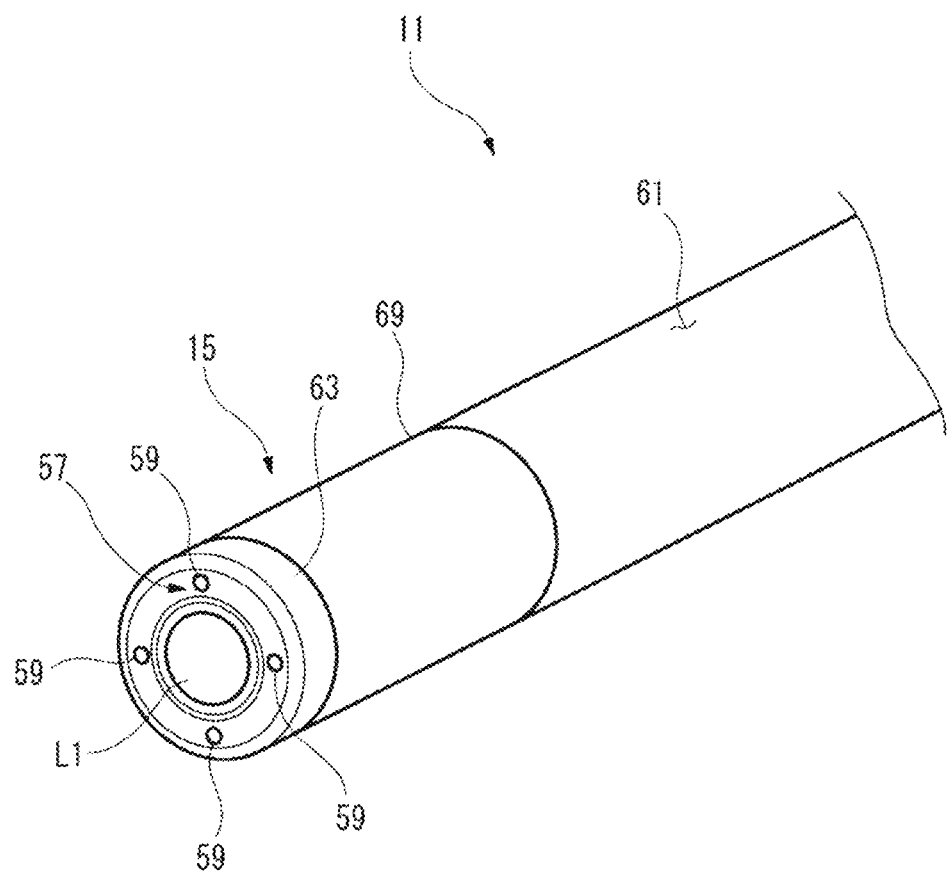
FIG. 2 is a perspective view illustrating a state when a distal portion of an endoscope according to a first embodiment is viewed from a front side.
Figure 3:
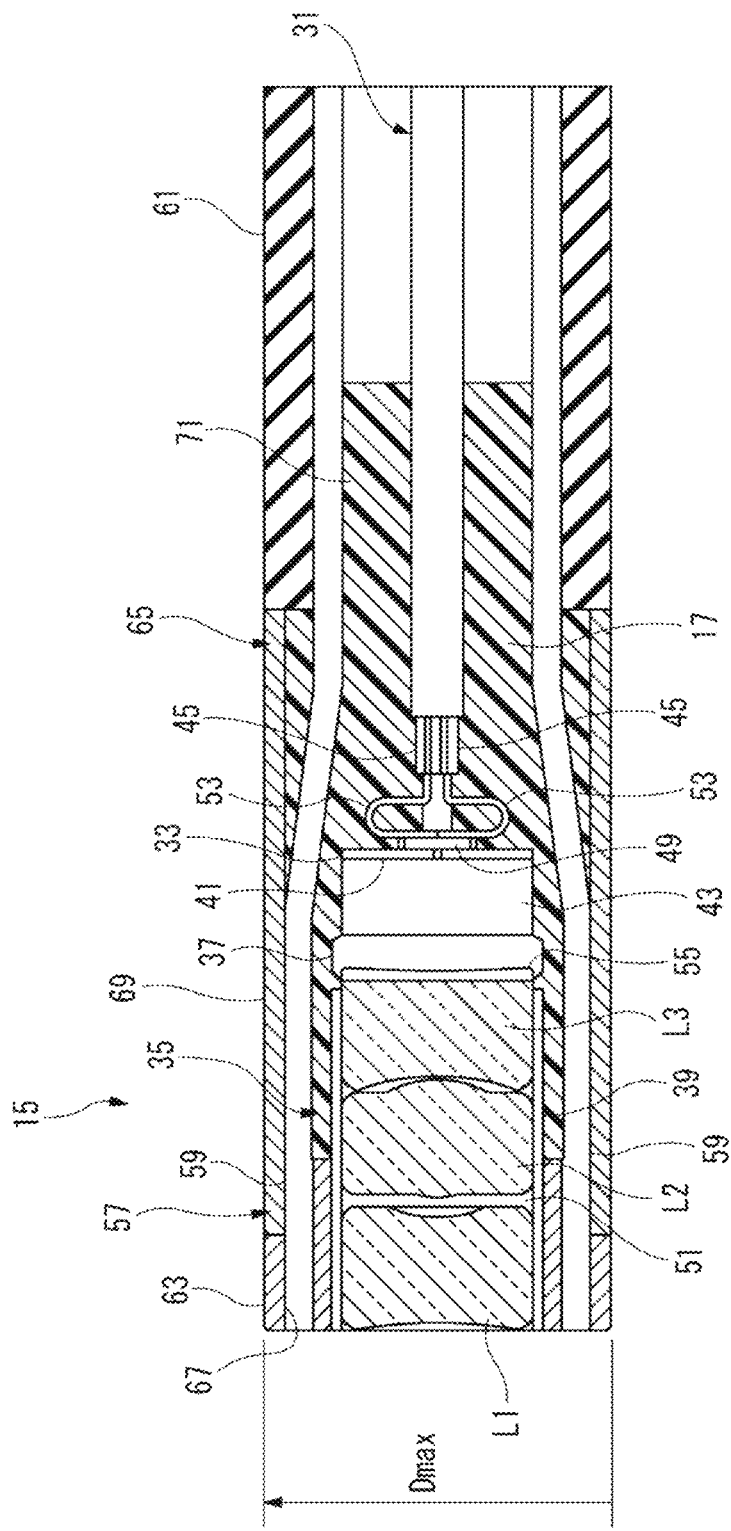
FIG. 3 is a sectional view illustrating an example of the distal portion of the endoscope according to the first embodiment.
Figure 4:
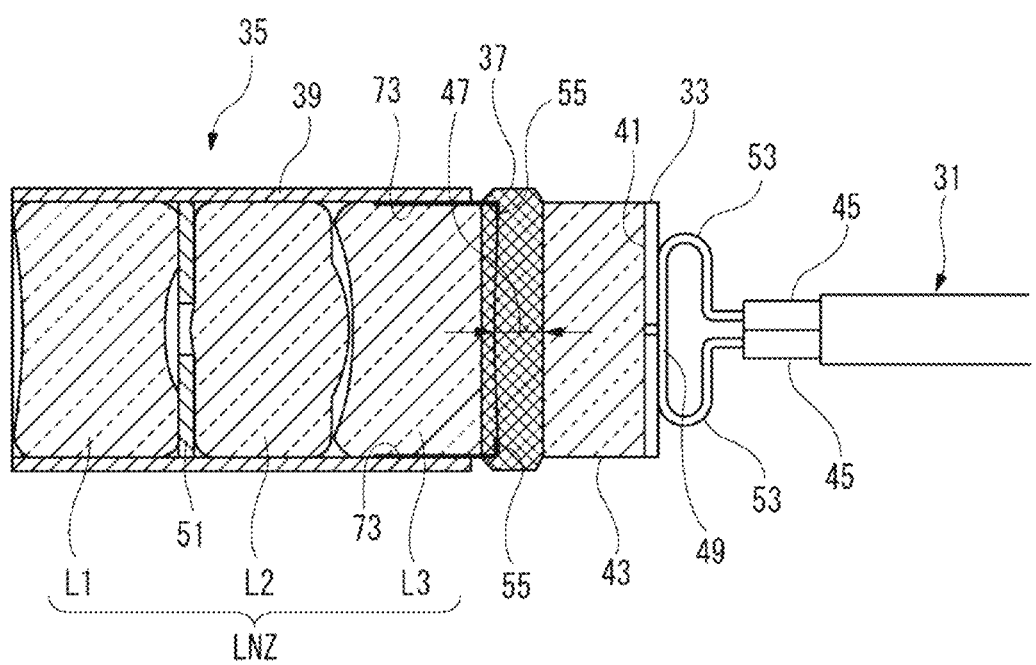
FIG. 4 is a sectional view illustrating an example of a configuration in which a separation portion of the endoscope according to the first embodiment is filled with a bonding resin.
Figure 5:
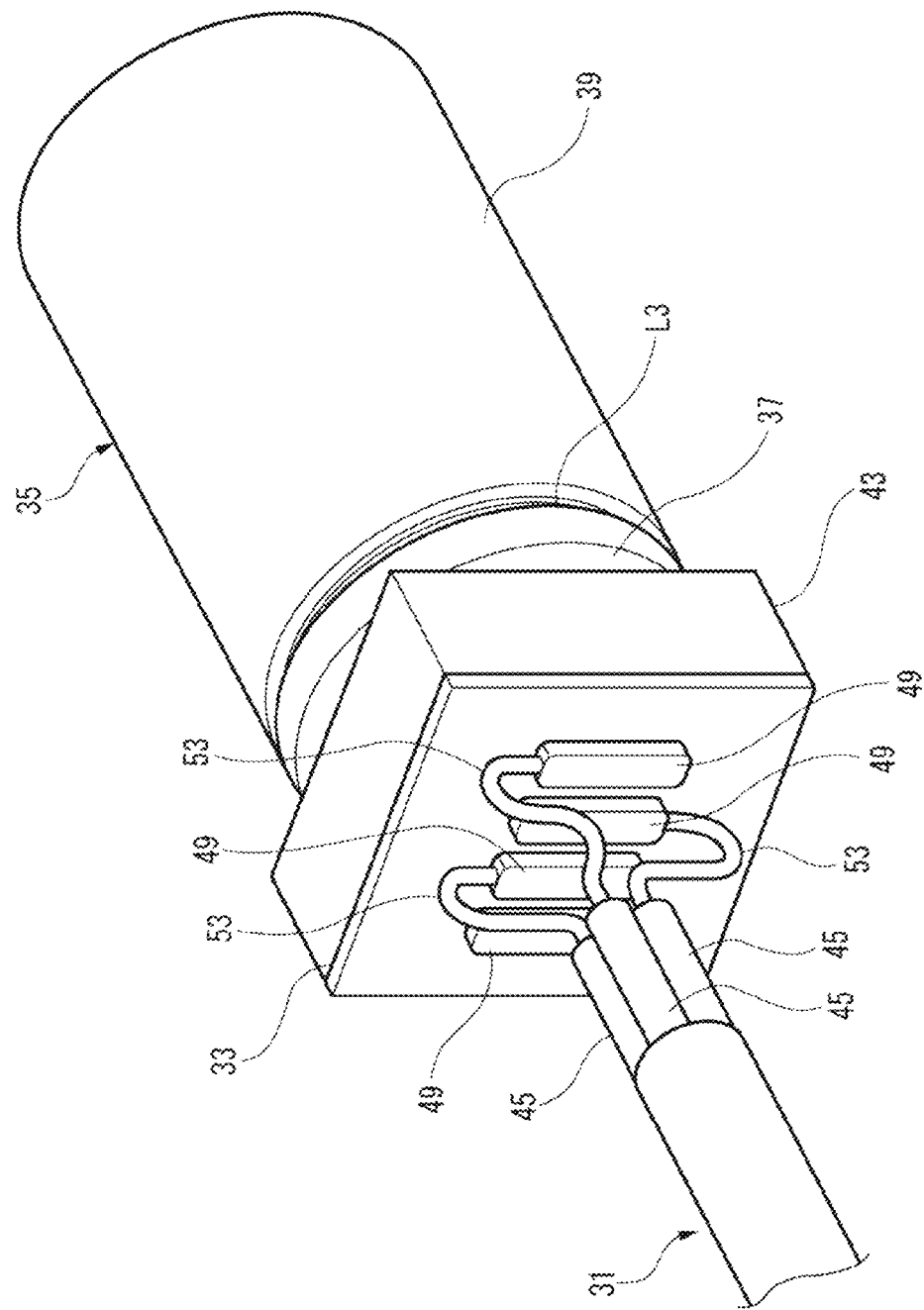
FIG. 5 is a perspective view illustrating a state where an image sensor having a transmission cable connected to a conductor connection part of the endoscope according to the first embodiment is viewed from a rear side.

FIG. 2 is a perspective view illustrating a state when the distal portion 15 of the endoscope 11 according to the first embodiment is viewed from a front side. FIG. 3 is a sectional view illustrating an example of the distal portion 15 of the endoscope 11 according to the first embodiment. FIG. 4 is a sectional view illustrating an example of a configuration in which a separation portion 47 of the endoscope 11 according to the first embodiment is filled with a bonding resin 37. FIG. 5 is a perspective view illustrating a state where the image sensor 33 having the transmission cable 31 connected to a conductor connection part 49 of the endoscope 11 according to the first embodiment is viewed from a rear side.

FIG. 2 illustrates a perspective view of a configuration of the distal portion 15 of the endoscope 11 illustrated in FIG. 1. FIG. 3 illustrates a sectional view of the configuration of the distal portion 15 illustrated in FIG. 2. FIG. 4 illustrates a sectional view of a configuration excluding a mold resin 17 in the distal portion 15 illustrated in FIG. 2. FIG. 5 illustrates a perspective view of a configuration when the image sensor 33 illustrated in FIG. 4 is viewed from a side opposite to a lens unit 35.

First Configuration Example

The endoscope 11 according to the first configuration example includes the lens unit 35 that accommodates a lens in a lens support member 39, the image sensor 33 whose imaging area is covered with the sensor cover glass 43, the bonding resin 37 that fixes the lens unit 35 and the sensor cover glass 43 in which an optical axis of the lens is coincident with the center of the imaging area, and the transmission cable 31 that has four electric cables 45 respectively connected to four conductor connection parts 49 disposed on a surface opposite (that is, rear side) to the imaging area of the image sensor 33.

Multiple (three in the illustrated example) lenses L1 to L3 formed of an optical material (for example, glass or a resin) and an iris 51 formed by being interposed between the lens L1 and the lens L2 in a state where all of these are close to each other in a direction of the optical axis are incorporated in the lens support member 39. The iris 51 is disposed in order to adjust the amount of light incident on the lens L2 or a lens 93. Only the light passing through the iris 51 can be incident on the lens L2 or the lens 93. Closing to each other means that these are slightly separated in order to avoid damage caused by the mutual contact between the lenses. The lenses L1 to L3 are fixed on an inner peripheral surface of the lens support member 39 over the entire periphery by using an adhesive.

The term of the "adhesive" in the following description does not strictly mean a substance used in order to bond a surface to a surface of a solid object. The "adhesive" is used in a broad meaning such as a substance which can be used for coupling of two objects or a substance having a function as a sealing material in a case where the cured adhesive includes a high barrier property against gases and liquids.

A front end of the lens support member 39 is hermetically enclosed (sealed) with the lens L1, and a rear end of the lens support member 39 is hermetically enclosed (sealed) with the lens L3. A configuration is adopted so that air or water does not enter the inside of the lens support member 39. Accordingly, the air cannot escape from one end to the other end of the lens support member 39. In the following description, the lenses L1 to L3 are collectively referred to as an optical lens group LNZ.

For example, nickel is used as a metal material configuring the lens support member 39. Nickel has relatively high rigidity and high corrosion resistance, and is suitable for a material configuring the distal portion 15. It is preferable that the periphery of the lens support member 39 is evenly coated with the mold resin 17 and the distal portion 15 is subjected to biocompatible coating before an inspection or at the time of surgery, so that nickel configuring the lens support member 39 is not directly exposed from the distal portion 15 at the time of the inspection or the surgery using the endoscope 11. For example, instead of nickel, a copper-nickel alloy may be used. The copper-nickel alloy also has the high corrosion resistance, and is suitable for the material configuring the distal portion 15. As a metal material configuring the lens support member 39, it is preferable to select a material which can be manufactured by means of electroforming (electroplating). Here, the reason for using the electroforming is that dimensions of a member manufactured by means of the electroforming are very accurate to an extent smaller than 1 μm (so-called submicron accuracy), and further that there are few irregularities when many member are manufactured. As the metal material configuring the lens support member 39, stainless steel (for example, SUS316) may also be used. The stainless steel (also referred to as a SUS tube) is very biocompatible, and is considered as suitable for the endoscope inserted into a small-diameter site such as the blood vessel of the human body, for example. The lens support member 39 is a very small member, and an error between the dimensions of the inner and exterior diameters affects the optical performance (that is, image quality of a captured image) of the endoscope 11. For example, the lens support member 39 is configured to include an electroformed nickel tube. In this manner, it is possible to obtain the endoscope 11 which can capture a high quality image while high dimensional accuracy is secured despite the small diameter.

The lens support member 39 may be a sheet material in addition to metal. The lens support member 39 may be configured so that positioning can be achieved when the optical axes of the respective lenses of the lens unit 35 are aligned with each other. If the lens unit 35 is covered with the mold resin 17, the relative positions of the respective lenses are fixed to each other. Therefore, the lens support member 39 can employ a material whose strength is weak, whose thickness is thin, and whose weight is light for the lens barrel used in order to support multiple lenses in the related art. This can contribute to the small-diameter distal portion 15 in the endoscope 11. The lens support member 39 is not intended to exclude the use of the metal-made lens barrel similar to that in the related art.

As illustrated in FIG. 5, for example, the image sensor 33 is configured to include an imaging device of a compact charge coupled device (CCD) or complementary metal-oxide semiconductor (CMOS) which has a square shape when viewed in the longitudinal direction. In the image sensor 33, light incident from the outside is caused to form an image on the imaging area 41 by the optical lens group LNZ inside the lens support member 39. In the image sensor 33, the imaging area 41 is covered with the sensor cover glass 43.

For example, the bonding resin 37 is configured to include a UV thermosetting resin. It is preferable that the bonding resin 37 has a light-transmitting property and a refractive index is close to that of air. In a case where the UV thermosetting resin is used as the bonding resin 37, an external surface portion can be cured by ultraviolet light irradiation, and the inside of the filling adhesive which cannot be irradiated with the ultraviolet light can be cured by heat treatment. The bonding resin 37 fixes the lens unit 35 in which the optical axis of the lens is coincident with the center of the imaging area 41, to the sensor cover glass 43. In this manner, the lens unit 35 and the image sensor 33 are directly bonded and fixed to each other by the bonding resin 37. That is, the lens unit 35 and the image sensor 33 are directly attached to each other via the bonding resin 37. For example, although the bonding resin 37 requires the heat treatment in order to obtain final hardness, the bonding resin 37 is a type of adhesives which are progressively cured to some degree of hardness by the ultraviolet light irradiation.

In the endoscope 11, in a case where a light-emitting surface of the lens which faces the sensor cover glass 43 is a concave surface, an edge portion 55 which is an annular end surface around the lens is bonded to the sensor cover glass 43. In this case, the exterior periphery of the lens and the exterior periphery of the lens support member 39 may also be concurrently fixed by the bonding resin 37. The edge portion 55 of the lens is bonded to the sensor cover glass 43, thereby disposing an air layer between the lens and the image sensor 33. Since the air layer is disposed between the lens and the image sensor 33, it is possible to improve optical performance of the lens. For example, it is possible to increase a refractive index difference of light emitted from the lens to the air layer. Accordingly, it is possible to obtain power for refracting the light. This facilitates optical design when the resolution is improved and a viewing angle is widened. As a result, the image quality of the image captured by the endoscope 11 is improved.

The four conductor connection parts 49 are disposed in the rear part on the rear surface side of the image sensor 33. For example, the conductor connection part 49 can be formed by land grid array (LGA). The four conductor connection parts 49 include a pair of power connection portions and a pair of signal connection portions. The four conductor connection parts 49 are electrically connected to the four electric cables 45 of the transmission cable 31. The transmission cable 31 includes a pair of power lines serving as the electric cable 45 and a pair of signal lines serving as the electric cable 45. That is, the pair of power lines of the transmission cable 31 are connected to the pair of power connection portions of the conductor connection part 49. The pair of signal lines of the transmission cable 31 are connected to the pair of signal connection portions of the conductor connection part 49.

As described above, according to the endoscope 11 of the first configuration example, the lens unit 35 and the image sensor 33 are fixed to each other in a state where the bonding resin 37 maintains a predetermined distance between the lens 35 and the image sensor 33. In the lens unit 35 and the image sensor 33 which are fixed to each other, the optical axis of the lens unit 35 and the center of the imaging area 41 are aligned with each other. A distance between the lens unit 35 and the image sensor 33 is aligned with a distance in which the incident light from an imaging subject, which passes through the lens unit 35, is focused on the imaging area 41 of the image sensor 33. The lens unit 35 and the image sensor 33 are fixed after being aligned with each other.

The separation portion 47 (refer to FIG. 4) is formed between the lens unit 35 and the image sensor 33 which are fixed to each other. The lens unit 35 and the image sensor 33 are relatively aligned with each other, and are fixed to each other by the bonding resin 37, thereby forming a shape of the separation portion 47. That is, the separation portion 47 functions as an adjusting gap for aligning the lens unit 35 and the image sensor 33 with each other. This adjusting gap does not disappear even if the adjusting gap is filled with the bonding resin 37. In a specific example having the above-described dimensions, the dimensions are adjusted in a range from at least approximately 30 μm to approximately 100 μm. In this case, tolerance is ±20 μm. Accordingly, the minimum adjusting gap remains to be 10 μm.

After the separation portion 47 serves as the adjusting gap and the alignment is completed between the lens unit 35 and the image sensor 33 in the endoscope 11, the separation portion 47 is used as a fixing space of the bonding resin 37. In this manner, the lens unit 35 and the image sensor 33 can be directly fixed to each other. Accordingly, it is unnecessary to provide an interposing member which is required in the related art, such as a frame or a holder for fixing the lens unit 35 to the image sensor 33. Since the frame or the holder can be omitted, the number of components is reduced, thereby simplifying a fixing structure. In this manner, the distal portion 15 of the endoscope 11 can be miniaturized. Even in a case where the distal portion 15 needs to be further miniaturized (for example, a reduced exterior diameter in the insertion part on the distal side), a configuration having the minimum dimensions can be adopted. In addition, it is possible to reduce the component cost. Furthermore, a few interposing members are required when the lens unit 35 and the image sensor 33 are fixed to each other. Accordingly, it is possible to reduce man-hour needed to carry out work for alignment and fixing, and it is possible to easily perform accurate alignment. The manufacturing cost can be reduced, and productivity can be improved.

According to the endoscope 11, the transmission cable 31 having the four electric cables 45 is connected to the image sensor 33. The endoscope 11 employs the transmission cable 31 having the four electric cables 45. In this manner, it is possible to compatibly achieve miniaturization and cost reduction. For example, four or less (for example, three) electric cables 45 of the transmission cable 31 can be employed in view of a relationship of an arrangement space of the conductor connection part 49 for the rear part on the rear surface side of the image sensor 33. However, in this case, for example, if one signal line is removed, a signal of a captured image or a controlling signal transmitted from the video processor 19 has to be superposed on a waveform of power passing through the power line. In this case, it is necessary to provide a modulation circuit or a demodulation circuit for signal superposition, thereby increasing the number of components and increasing total cost. If a dedicated signal line is used in order to transmit and receive various signals (image signal of a captured image or controlling signal), a circuit configuration is facilitated, but it is disadvantageous to use the dedicated signal line when the endoscope needs the small diameter. On the other hand, if the electric cables 45 more than four (for example, five) of the transmission cable 31 are employed, the arrangement space of the individual conductor connection part 49 for the rear part on the rear surface side of the image sensor 33 is narrowed. In a case of manufacturing the endoscope 11 in which the maximum exterior diameter of the distal portion 15 is set to 1.8 mm or smaller as will be described later, it is difficult to carry out connection work by means of soldering, and it is difficult to manufacture the endoscope 11. As described above, in the endoscope 11, the transmission cable 31 employs the four electric cables 45. Therefore, while the miniaturization and the cost reduction are compatibly achieved, an operation effect is remarkably obtained.

Second Configuration Example

According to the endoscope 11 of a second configuration example, in the endoscope 11 according to the present embodiment, the maximum exterior diameter Dmax of the distal portion 15 can be formed within a range from a limited diameter to 1.8 mm which corresponds to a diameter of a circumscribed circle of a substrate of the image sensor 33 which can be diced.

In the endoscope 11 according to the present embodiment, as the image sensor 33 whose cross section in the direction perpendicular to the optical axis has a square shape, those which have one side dimension of 1.0 mm are used. In this manner, in the endoscope 11, a diagonal dimension of the image sensor 33 is approximately 1.4 mm. If a light guide 57 (for example, (φ150 μm) serving as lighting means is included therein, it is possible to set the maximum exterior diameter Dmax to 1.8 mm or smaller.

As described above, according to the endoscope 11 of the second configuration example, since the maximum exterior diameter Dmax is set to be smaller than 1.8 mm, for example, it is possible to easily insert the endoscope 11 into the blood vessel of the human body.

Third Configuration Example

According to the endoscope 11 of a third configuration example, in the endoscope 11 according to the present embodiment, the substrate of the image sensor 33 is formed in a square shape as illustrated in FIG. 5, and the four conductor connection parts 49 are arranged parallel to each other along one side of the substrate of the image sensor 33. One of the conductor connection parts 49 is formed in a rectangular shape. The four conductor connection parts 49 are arranged separate from each other while long sides thereof are parallel to each other. The four conductor connection parts 49 are arranged in a central part of the substrate of the image sensor 33. Accordingly, the respective conductor connection parts 49 are separated from a peripheral edge of the substrate of the image sensor 33.

In the transmission cable 31, each conductor of the power line and the signal line which are the electric cables 45 is covered with an insulating coating material. Among the four electric cables 45, two are laterally arranged, and two are vertically arranged at two stages. The exterior periphery of the insulating coating material is further bundled by an exterior cover, thereby forming one transmission cable 31. Each conductor has a bending portion 53 which bends in a U-shape along the longitudinal direction of the conductor connection part 49. The electric cable 45 is brought into contact with the conductor connection part 49 by the bending portion 53 which is formed in advance. In the electric cable 45, a distal end of the bending portion 53 is connected to the conductor connection part 49 by means of soldering. The image sensor 33 and the transmission cable 31 are covered with the mold resin 17. Accordingly, each exterior cover of the conductor connection part 49, the bending portion 53, the electric cable 45, and the transmission cable 31 is embedded in the mold resin 17.

As described above, according to the endoscope 11 of the third configuration example, the four conductor connection parts 49 can be arranged parallel to each other in the central part of the substrate of the image sensor 33, thereby facilitating the formation of the conductor connection parts 49. The conductor of the electric cable 45 is connected to each of the four conductor connection parts 49 which are separated in one direction, by means of soldering. Accordingly, it is possible to easily carry out the connection work. The conductor connection parts 49 are arranged in the central part of the substrate of the image sensor 33. Accordingly, it is possible to form the bending portion 53 in the conductor. The bending portion 53 is embedded and fixed by the molded part 65. Accordingly, it is possible to minimize tension acting on the transmission cable 31 to be applied to a bonded portion between the conductor and the conductor connection part 49 (acts as a strain relief). In this manner, it is possible to improve connection reliability between the electric cable 45 and the conductor connection part 49.

Fourth Configuration Example

According to the endoscope 11 of a fourth configuration example, in the endoscope 11 according to the present embodiment, the lighting means is disposed along the lens unit. That is, the endoscope 11 according to the fourth configuration example has the light guide 57 serving as an example of the lighting means. Hereinafter, a case where the lighting means is the light guide 57 will be described as an example. However, the lighting means can be an LED which is directly attached to a distal insertion surface of the distal portion 15. In this case, it is unnecessary to provide the light guide 57.

The light guide 57 is formed of one optical fiber 59. For example, as the optical fiber 59, a plastic optical fiber (POF) is preferably used. The plastic optical fiber is formed of plastic by using a material such as a silicone resin or an acrylic resin for both core and cladding. For example, the optical fiber 59 may be a bundle fiber in which terminal metal fittings are attached to both ends after multiple optical fiber strands are bundled. In the optical fiber 59, a distal end functions as a light-emitting end surface in the distal portion 15, and a proximal end is connected to a ferrule of the plug part 23. For example, a light source is an LED disposed in the socket portion 27. In the endoscope 11, the plug part 23 is connected to the socket portion 27, thereby causing the light emitted from the LED to propagate through the optical fiber 59 of the light guide 57 and to be emitted from the distal end. According to this configuration, one optical fiber can configure a route from the light source to the light-emitting end of the illumination light. Therefore, it is possible to minimize the optical loss.

As described above, according to the endoscope 11 of the fourth configuration example, since the light guide 57 is provided, it is possible to capture an image in a dark site by using the endoscope 11 alone.

Fifth Configuration Example

Figure 6:
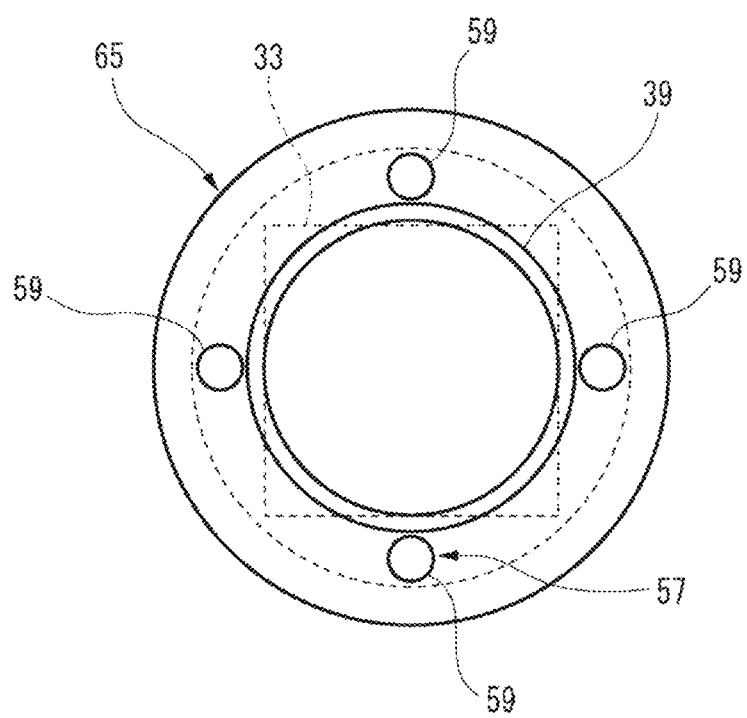
FIG. 6 is a front view illustrating an example of the distal portion which represents an arrangement example of a light guide as an example of lighting means.

FIG. 6 is a front view illustrating an example of the distal portion which represents an arrangement example of the light guide 57 as an example of the lighting means. According to the endoscope 11 of a fifth configuration example, in the endoscope 11 according to the present embodiment, a configuration is adopted in which multiple light guides 57 serving as an example of the lighting means are disposed in the circumferential direction of the lens unit 35. Four light guides 57 can be disposed at equal intervals in the circumferential direction of the lens unit 35.

As described above, according to the endoscope 11 of the fifth configuration example, the four light guides 57 are disposed at equal intervals in the circumferential direction of the lens unit 35. Accordingly, a shadow is less likely to appear vertically and laterally in an imaging subject. In this manner, the endoscope 11 can clearly capture an image, compared to a configuration having one or two light guides 57.

Sixth Configuration Example

According to the endoscope 11 of a sixth configuration example, in the endoscope 11 according to the present embodiment, the image sensor 33 is formed in a square shape. The optical fiber 59 of the four light guides 57 are arranged at substantially the center of each side of the substrate of the image sensor 33 in a space interposed between the substrate of the image sensor 33 and the circumscribed circle of the substrate of the image sensor 33.

As described above, according to the endoscope 11 of the sixth configuration example, it is possible to effectively utilize the space interposed between the square-shaped image sensor 33 and the circular molded part 65 which is substantially circumscribed to the image sensor 33. Without increasing the exterior diameter of the distal portion 15, it is possible to easily arrange the multiple (particularly, four) optical fibers 59. In this manner, in the endoscope 11, without increasing the exterior diameter of the distal portion 15, a clear image can be obtained while the manufacturing is facilitated.

Seventh Configuration Example

According to the endoscope 11 of a seventh configuration example, in the endoscope 11 according to the present embodiment, at least a portion of the lens unit, the image sensor, a portion of the transmission cable, and a portion of the lighting means are coated with and fixed by the mold resin. The molded part 65 formed of the mold resin is configured to include a resin material containing an additive. In this manner, a light transmittance rate can be set to 10% or smaller.

Figure 7:
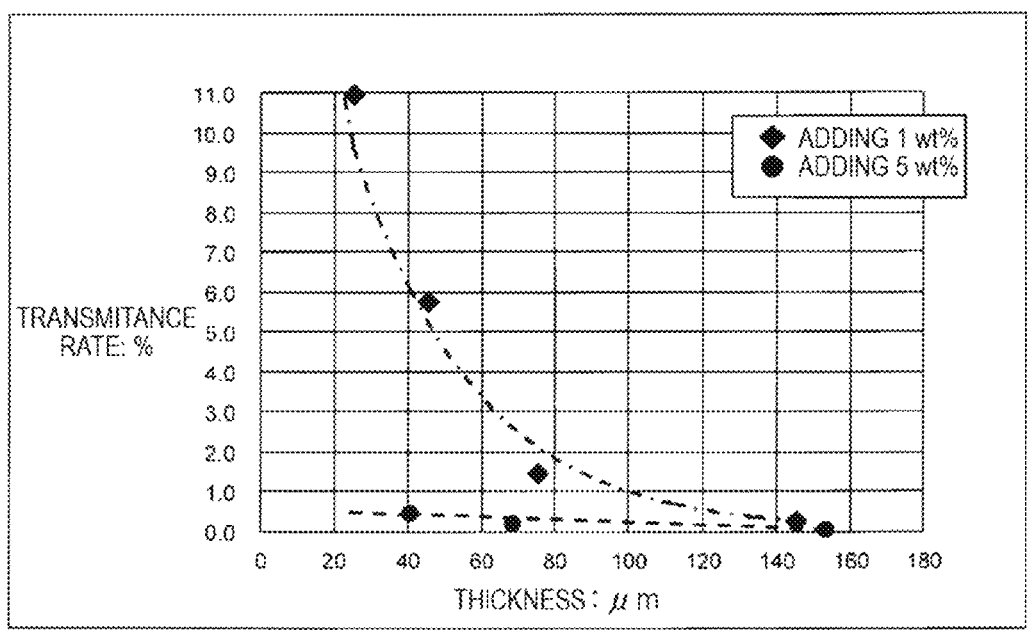
FIG. 7 is a characteristic diagram illustrating an example of a relationship between a thickness and a transmittance rate of a molded part.

FIG. 7 is a characteristic diagram illustrating an example of a relationship between the thickness and the transmittance rate of the molded part 65. FIG. 7 illustrates an example of measuring the transmittance rate in a case where carbon black as the additive is added to a mold resin material (epoxy-based resin). In FIG. 7, a black circle and a broken line indicate a case where the carbon black is added as much as 5% by weight (wt %), and a black diamond and a dashed line indicate a case where the carbon black is added as much as 1% by weight (wt %).

In the case where the carbon black is added as much as 5% by weight, without depending on a size of the thickness of the molded part 65 at all, excellent light blocking performance can be obtained to such an extent that the light transmittance rate is approximately 0.5% (light blocking rate 99.5%), even if the thickness is 30 μm or smaller. In the case where the carbon black is added as much as 1% by weight, the transmittance rate increases as the thickness of the molded part 65 decreases. In the case of adding the carbon black as much as 1% by weight, if the thickness of the molded part 65 is 30 μm or greater, it is possible to minimize the transmittance rate to 8.0% or smaller. Accordingly, the molded part 65 can sufficiently satisfy a condition that the transmittance rate is 10% or smaller by setting a thickness T to 30 μm or greater. For example, if the thickness of the molded part 65 is set to 50 μm or greater, when the carbon black is added as much as 1% by weight, the transmittance rate is 4.5% or smaller, and when the carbon black is added as much as 5% by weight, the transmittance rate is 0.5% or smaller. Therefore, it is possible to more reliably block the light.

If the transmittance rate in the molded part 65 is 10% or smaller, the imaging unit including the lens unit 35 and the image sensor 33 can satisfactorily obtain a captured image which is less affected by stray light. If the transmittance rate in the molded part 65 is 6% or smaller, it is possible to sufficiently minimize the influence of the stray light even if sensitivity of the image sensor 33 is high. If the transmittance rate is greater than 10%, the captured image receives the influence of the stray light, thereby causing a problem of a poorly captured image.

Figure 8A:
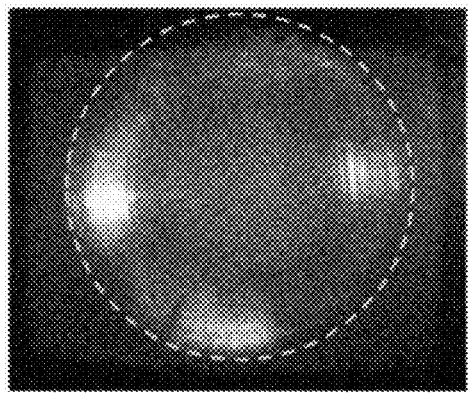
FIG. 8A is a view illustrating an example of a captured image in a case where stray light is present.
Figure 8B:
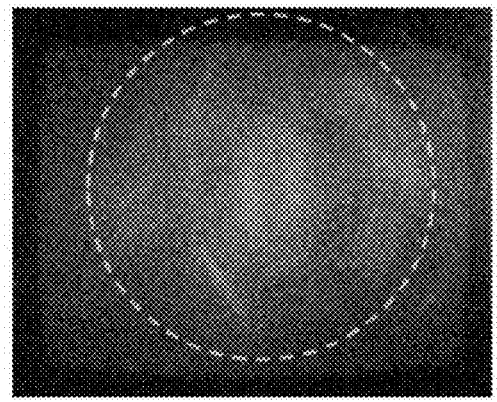
FIG. 8B is a view illustrating an example of a captured image in a case where stray light is absent.

FIG. 8A is a view illustrating an example of the captured image in a case where the stray light is present, and FIG. 8B is a view illustrating an example of the captured image in a case where the stray light is absent. In a case where the stray light is present as illustrated in FIG. 8A, whiteout occurs in an annular shape due to the stray light on the captured image, and thus, a clear image cannot be obtained. The imaging unit using the endoscope 11 needs to be in a state where the stray light is absent as illustrated in FIG. 8B.

In a case where the additive is added to the molded part 65, as in the example illustrated in FIG. 7, the light blocking performance is improved as the adding amount (containing amount) of the additive increases. On the other hand, bonding strength of the molded part 65 tends to be degraded. Accordingly, it is necessary to add a suitable amount to the mold resin material in accordance with bonding strength characteristics of the additive.

Figure 9:
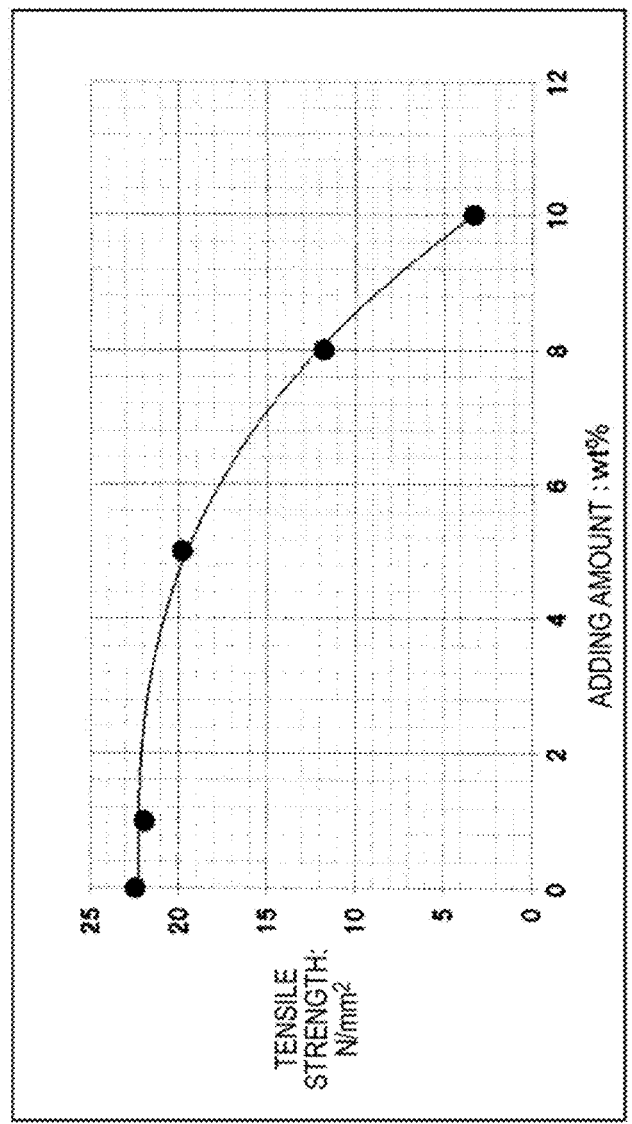
FIG. 9 is a characteristic diagram illustrating an example of a relationship between an additive adding amount and tensile strength in the molded part.

FIG. 9 is a characteristic diagram illustrating an example of a relationship between an adding amount of the additive and tensile strength in the molded part 65. FIG. 9 illustrates an example of measuring the tensile strength in a case where the carbon black as the additive is added to the mold resin material (epoxy-based resin). Here, the tensile strength corresponds to the bonding strength of the molded part 65. As illustrated in FIG. 9, in a case where the adding amount is 1% by weight, the tensile strength decreases as much as approximately 2.5% only. In a case where the adding amount is 5% by weight, the tensile strength decreases as much as approximately 12%. If the tensile strength decreases as much as approximately 20%, the bonding strength cannot be sufficiently obtained as a material of the molded part in some cases. Accordingly, in a case where the carbon black is added, it is preferable to set the adding amount to 5% by weight or smaller.

In a case where a conductive material such as the carbon black is used as the additive, electrical resistance increases as the adding amount increases, thereby allowing conductivity to be added.

FIG. 10 is a view illustrating an example of a relationship among the adding amount of the additive, a resistance value, and a light blocking rate in the molded part 65. FIG. 10 illustrates an example of measuring the resistance value and the light blocking rate in a case where the carbon black as the additive is added to the mold resin material (epoxy-based resin). As the adding amount of the carbon black, three cases of no addition (adding 0% by weight), adding 1% by weight, and adding 5% by weight are measured. The light blocking rate is an example in a case where the thickness of the molded part 65 is set to 50 μm. In the case of no adding, the resistance value is 1.8 to $5.0 \times 10^{13}$. In the case of adding 1% by weight, the resistance value is 2.5 to $3.0 \times 10^{13}$, and the light blocking rate is 95% or greater. In the case of adding 5% by weight, the resistance value is 3.5 to $5.0 \times 10^{10}$, and the light blocking rate is 99% or greater. In the case of adding 5% by weight, compared to the case of adding 1% by weight, the electrical resistance value decreases 1,000 times or more. Therefore, it is necessary to add a suitable amount to the mold resin material in accordance with conductive characteristics of the additive and insulation characteristics required in an internal configuration element (electronic circuit) which is a sealing target.

In a case where the electrical resistance is small in the molded part 65, a leakage current is generated in the conductor connection part 49 and the transmission cable 31 which are connected to the image sensor 33. Thus, in some cases, electrical characteristics around a signal processor of the imaging unit are degraded. On the other hand, suitable conductivity is provided for the molded part 65. Accordingly, in a case where static electricity is generated in the imaging unit, the impact of electrostatic discharge is reduced. Therefore, it is possible to minimize an excessive current flowing to the image sensor 33, and it is possible to prevent electrostatic breakdown of the image sensor 33. That is, a countermeasure against electrostatic surge is available for the imaging unit.

As described above, according to the endoscope 11 of the seventh configuration example, the resin material (mold resin 17) of the molded part 65 contains the additive. Accordingly, the light transmittance rate can decrease to 10% or smaller in the molded part 65, and the thickness of the molded part 65 can decrease. In this manner, while light blocking characteristics are sufficiently provided for the imaging unit of the endoscope 11, the endoscope 11 can be miniaturized.

Eighth Configuration Example

According to the endoscope 11 of an eighth configuration example, as illustrated in FIG. 3, the endoscope 11 according to the present embodiment can include the lens unit 35 that accommodates the lens in the lens support member 39, the image sensor 33 whose imaging area 41 is covered with the sensor cover glass 43, the bonding resin 37 that fixes the lens unit 35 and the sensor cover glass 43 in which the optical axis of the lens is coincident with the center of the imaging area 41, the distal portion 15 in which the maximum exterior diameter Dmax is formed within a range from the limited diameter to 1.8 mm which corresponds to the diameter of the circumscribed circle of the substrate of the image sensor 33 which can be diced, the molded part 65 that causes the mold resin 17 to cover and fix at least a portion of the lens unit 35 and the image sensor 33, and a tubular sheath 61 that is formed so as to have the same exterior diameter as that of the distal portion 15, and that is connected to the distal portion 15 by covering at least a portion of the molded part 65.

In the following description, the same reference numerals will be given to the same members or the same configurations, and description thereof will be omitted. The endoscope 11 (refer to FIG. 3) according to the eighth configuration example will be appropriately described in comparison with the endoscope 11 (refer to FIG. 11) according to a tenth configuration example.

The sheath 61 is formed of a flexible resin material. In order to provide strength for the sheath 61, the sheath 61 can include a single wire on the inner peripheral side, multiple lines, and a braided tensile strength wire. As an example, the tensile strength wire can include aramid fibers such as poly-p-phenylene terephthalamide fibers, polyester-based fibers such as polyarylate fibers, polyparaphenylene benzobisoxazole fibers, and polyethylene terephthalate fibers, nylon fibers, thin tungsten wires, or thin stainless steel wires.

Similarly to the endoscope 11 (refer to FIG. 11) according to the tenth configuration example (to be described later), in the endoscope 11 according to the eighth configuration example, the overall image sensor 33, at least a portion on the image sensor 33 side of the lens unit 35, a portion of the transmission cable 31, and a portion of the light guide 57 are coated with and fixed by the mold resin 17. The concept of "at least" also includes that the mold resin 17 covers the entire exterior periphery of the lens support member 39. The mold resin 17 covers the image sensor 33 and the lens unit 35, thereby also continuously covering the separation portion 47 therebetween. The distal portion 15 of the endoscope 11 according to the eighth configuration example may include an X-ray opaque marker. In this manner, the endoscope 11 according to the eighth configuration example easily checks a distal position under X-ray fluoroscopy.

Similarly to the endoscope 11 (refer to FIG. 11) according to the tenth configuration example (to be described later), in the endoscope 11 according to the eighth configuration example, the distal portion 15 includes a distal flange portion 63. For example, the distal flange portion 63 can be formed using stainless steel. The distal flange portion 63 is formed in a cylindrical shape in which a large-diameter portion and a small-diameter portion are continuous with each other from the distal side. The exterior diameter of the large-diameter portion of the distal flange portion 63 is formed to be the maximum exterior diameter Dmax (1.8 mm). An insertion hole (not illustrated) for inserting the four optical fibers 59 is disposed in the large-diameter portion. The respective optical fibers 59 are inserted into the insertion hole. An insertion hole (not illustrated) for inserting the lens unit 35 is disposed in the small-diameter portion. The lens unit 35 is inserted into the insertion hole. The distal flange portion 63 coaxially holds the lens unit 35. A fiber holding hole 67 for holding a distal side of the optical fiber 59 is drilled on the exterior side from the small-diameter portion, in the large-diameter portion of the distal flange portion 63. Four fiber holding holes 67 are disposed at equal intervals in the circumferential direction. The optical fiber 59 whose distal side is inserted into the fiber holding hole 67 is drawn out rearward along the small-diameter portion.

In the endoscope 11 according to the eighth configuration example, the optical fiber 59 in the rear of the distal flange portion 63 is arranged inside a cover tube 69 (refer to FIG. 3). The cover tube 69 is formed so as to have the same exterior diameter as that of the distal flange portion 63. The cover tube 69 is formed of a material such as metal and a resin. The cover tube 69 has a total length in which a distal end thereof comes into contact with the large-diameter portion of the distal flange portion 63 and at least a rear end reaches the transmission cable 31. The inside of the cover tube 69 is filled with the mold resin 17. That is, in the endoscope 11 according to the eighth configuration example, the molded part 65 is covered with the cover tube 69. In the endoscope 11 according to the tenth configuration example (to be described later), the cover tube 69 is omitted. Except that the distal end of the sheath 61 is in contact with the rear end of the distal flange portion 63 and both of these are bonded to each other (refer to FIG. 11), the endoscope 11 according to the eighth configuration example has the same configuration as that of the endoscope 11 according to the first configuration example.

The molded part 65 filling the cover tube 69 has a small-diameter extension portion 71 (refer to FIG. 3) which extends rearward from the rear end of the cover tube 69. The small-diameter extension portion 71 is formed in a columnar shape, and has the four optical fibers 59 embedded therein. The small-diameter extension portion 71 has the transmission cable 31 embedded inside the four optical fibers 59. The inner diameter side of the sheath 61 is fixed to the exterior periphery of the small-diameter extension portion 71 by using an adhesive. That is, in the endoscope 11 according to the eighth configuration example illustrated in FIG. 3, the distal flange portion 63, the cover tube 69, and the sheath 61 are continuous with each other so as to coaxially have the maximum exterior diameter Dmax of 1.8 mm. In the endoscope 11 according to the tenth configuration example illustrated in FIG. 11, the distal flange portion 63 and the sheath 61 are continuous with each other so as to coaxially have the maximum exterior diameter Dmax of 1.8 mm.

As described above, according to the endoscope 11 of the eighth configuration example and the tenth configuration example, at least a portion of the lens unit 35, the image sensor 33, and a portion of the transmission cable 31 are coated with and fixed by the mold resin 17. Accordingly, a small number of interposing components is disposed when the lens unit 35 and the image sensor 33 are fixed to each other. In this manner, the distal portion 15 of the endoscope 11 can have a small diameter. Even in a case where the diameter of the distal portion 15 is further reduced, a configuration having the minimum dimension can be adopted. In addition, the component cost can be reduced. For example, it is possible to realize the endoscope 11 applicable so that the endoscope 11 can image a very thin lesion site such as the blood vessel of the human body. As a result, it is possible to provide the miniaturized and cost-reduced endoscope 11.

The molded resin 17 is continuously molded across the image sensor 33 and the lens unit 35, thereby contributing to increased fixing strength between the image sensor 33 and the lens unit 35. The mold resin 17 also improves airtightness (that is, few minor gaps), water-tightness, and light blocking performance of the separation portion 47. Furthermore, the mold resin 17 also improves the light blocking performance when the optical fiber 59 for light guide 57 is embedded therein.

In the distal portion 15 of the endoscope 11, the light guide 57 is molded by the mold resin 17. The light guide 57 is caused to act as a structural member. Accordingly, even in the small-diameter endoscope 11, it is possible to improve connection strength between the flexible portion 29 and the distal portion 15. Furthermore, in the endoscope 11, in a case where the distal portion 15 is viewed from the exterior most surface on the insertion side (refer to FIG. 6) of the distal flange portion 63, a portion between the insertion hole (not illustrated) of the lens unit 35 which is disposed in advance in the distal flange portion 63 and the lens unit 35, and further portions between the four fiber holding holes 67 disposed in advance in the distal flange portion 63 so as to correspond to each optical fiber 59 and the respective optical fibers 59 are respectively filled with the bonding resin 37. Therefore, in the endoscope 11, there is no gap between the above-described respective insertion holes or fiber holding holes 67 and each member (that is, the lens support member 39 and the optical fiber 59). In the endoscope 11, a portion between the distal flange portion 63 and the cover tube 69, a portion between the cover tube 69 and the sheath 61, and a portion between the distal flange portion 63 and the sheath 61 are respectively bonded by the bonding resin 37, thereby removing the gap between the distal flange portion 63 and the cover tube 69, between the cover tube 69 and the sheath 61, and between the distal flange portion 63 and the sheath 61 respectively. Accordingly, if the endoscope 11 is subjected to sterilization (that is, cleaned) after being used during the inspection or the surgery, this reduces possibilities that cleaning remnants such as unnecessary liquids may adhere to the endoscope 11. Therefore, the endoscope 11 can be very conveniently used in terms of hygiene when the endoscope 11 is used for the subsequent inspection or surgery.

According to the endoscope 533 in the related art disclosed in WO2013/146091, the axis of the distal portion and the optical axis of the lens unit 547 are eccentric with each other. Therefore, a distance to an imaging subject is likely to vary due to a rotation angle of the distal portion, and it is difficult to stably obtain a satisfactory image. Furthermore, if the axis of the distal portion and the optical axis of the lens unit 547 are eccentric with each other, an interference condition between a tube inner wall and the distal portion varies due to the rotation angle of the distal portion, thereby degrading operability particularly when the distal portion enters a thin hole. In contrast, according to the endoscope 11 of the eighth configuration example, the distal flange portion 63, the cover tube 69, and the sheath 61 are coaxially continuous with each other. According to the endoscope 11 of the tenth configuration example, the distal flange portion 63 and the sheath 61 are coaxially continuous with each other. Accordingly, all of these are likely to have a small diameter. Therefore, it is possible to stably obtain a satisfactory image, and it is possible to improve insertion operability.

Ninth Configuration Example

According to the endoscope 11 of a ninth configuration example, in the endoscope 11 according to the present embodiment, the thickness of the sheath 61 can be set within a range of 0.1 to 0.3 mm. The thickness of the sheath 61 is coincident with a step dimension in a step portion between the cover tube 69 and the small-diameter extension portion 71. The small-diameter extension portion 71 protrudes to a side opposite to the lens unit 35 across the image sensor 33. That is, one transmission cable 31 is arranged around the center of the small-diameter extension portion 71, and the four optical fibers 59 are arranged outside the small-diameter extension portion 71. Accordingly, compared to the molded part 65 having the image sensor 33 embedded therein, the small-diameter extension portion 71 can easily have a small diameter. That is, the sheath 61 has the same exterior diameter as that of the cover tube 69. Therefore, the thickness of the sheath 61 is more freely designed.

As described above, according to the endoscope 11 of the ninth configuration example, the thickness of the sheath 61 can be as thick as 0.3 mm. Accordingly, it becomes easy to increase tensile strength of the sheath 61.

Tenth Configuration Example

Figure 11:
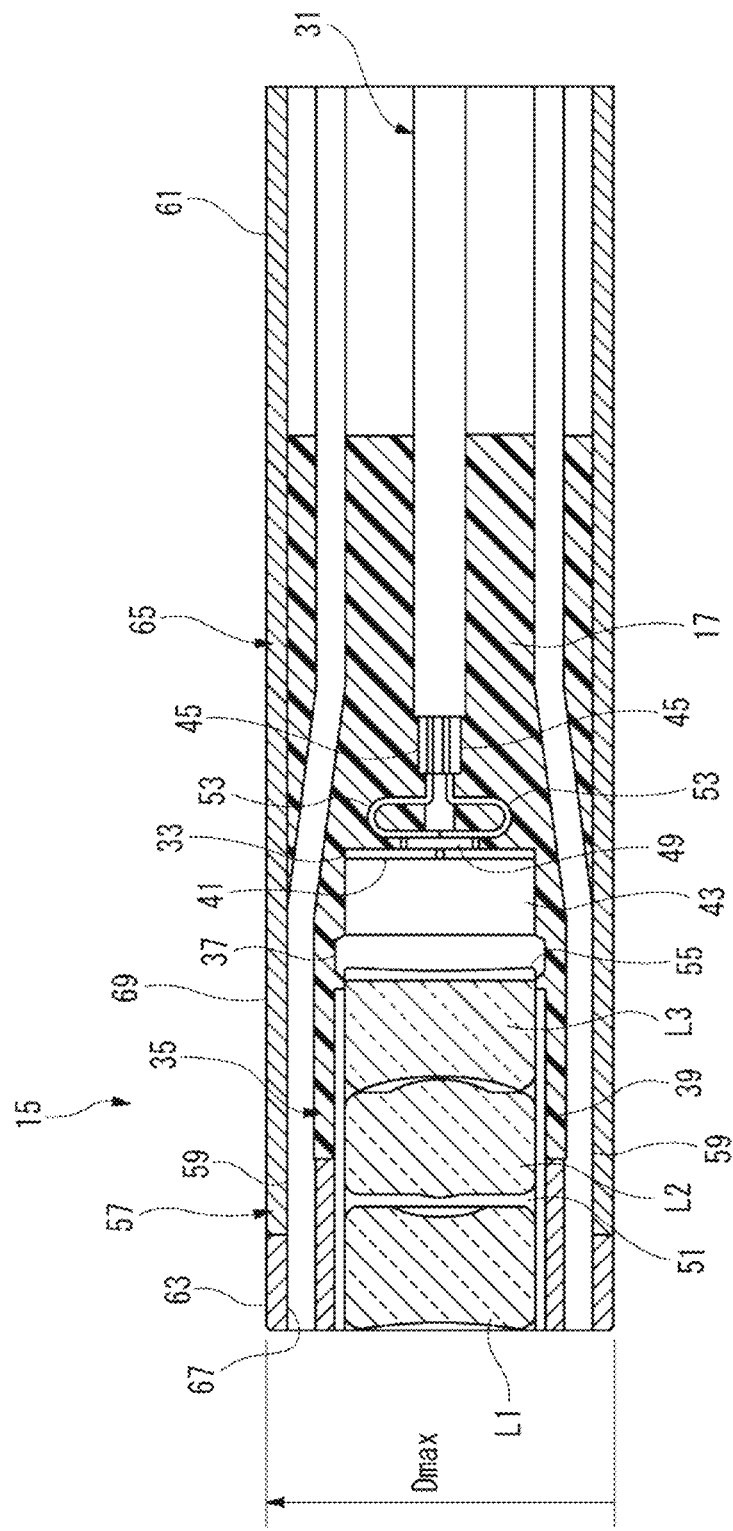
FIG. 11 is a sectional view illustrating an example of a configuration in which a thin sheath is connected to the distal portion.

FIG. 11 is a sectional view illustrating an example of a configuration in which a thin sheath is connected to the distal portion.

According to the endoscope 11 of a tenth configuration example, in the endoscope 11 according to the present embodiment, the thickness of the sheath 61 can be set to 0.1 mm. In a case where the thickness of the sheath 61 is set to 0.1 mm, the endoscope 11 does not require the cover tube 69 described in the endoscope 11 according to the eighth configuration example. That is, the endoscope 11 according to the tenth configuration example, the sheath 61 is caused to have substantially the same thickness (0.1 mm) as the thickness of the cover tube 69. In this manner, it is possible to cover the molded part 65 having the image sensor 33 and the lens unit 35 which are embedded therein. In the endoscope 11 according to the tenth configuration example, the distal end of the sheath 61 is in contact with and fixed to a rear end surface of the distal flange portion 63 by using an adhesive. In the sheath 61, the above-described tensile strength wire can compensate degraded tensile strength caused by the thinned thickness.

As described above, according to the endoscope 11 of the tenth configuration example, the cover tube 69 can be omitted, and the sheath 61 can be directly connected to the distal flange portion 63. Therefore, it is possible to decrease the number of components.

Second Embodiment

Next, an endoscope 111 according to a second embodiment will be described.

Figure 12:
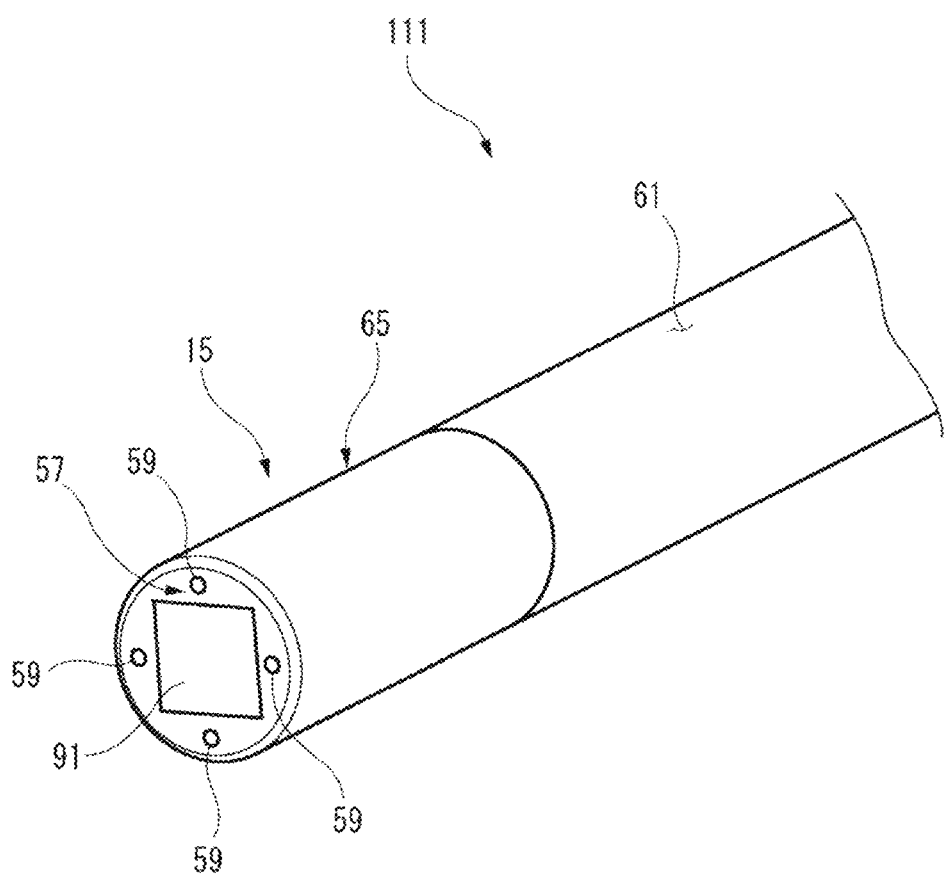
FIG. 12 is a perspective view illustrating a state where a distal portion of an endoscope according to a second embodiment is viewed from a front side.
Figure 13:
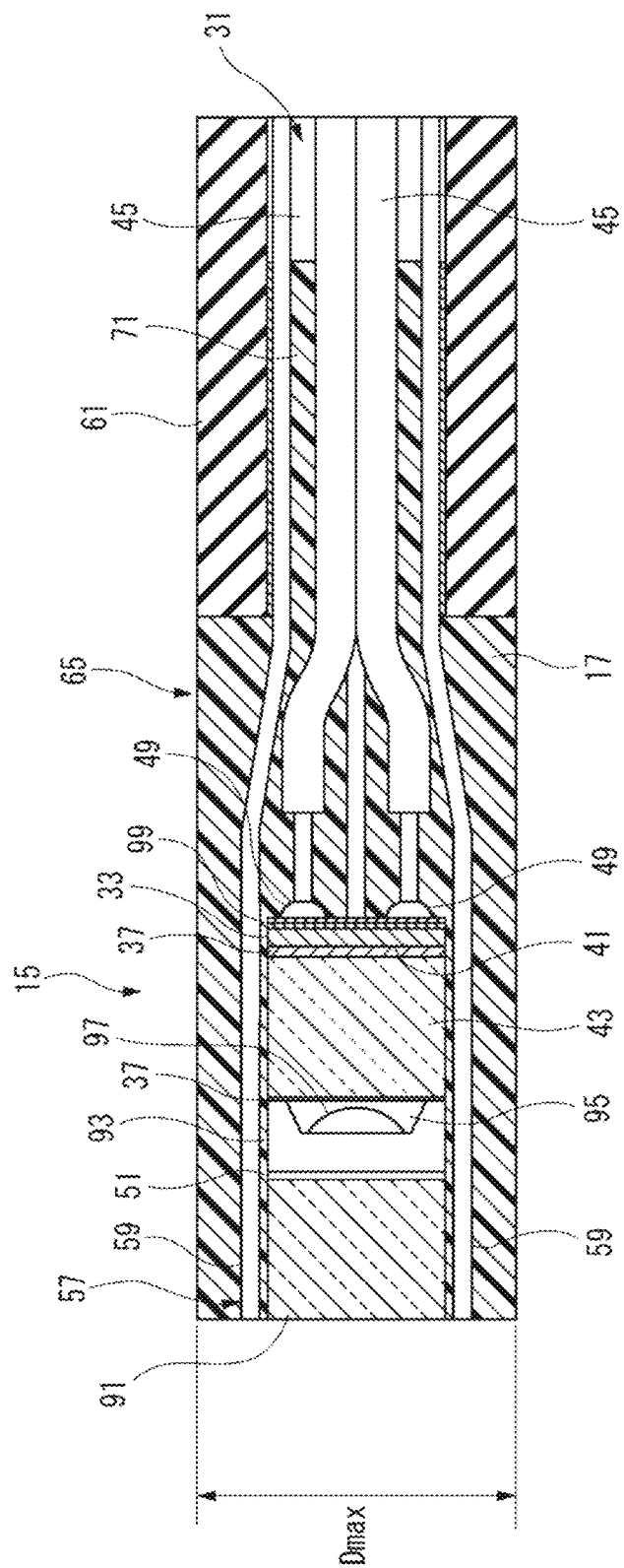
FIG. 13 is a sectional view illustrating a configuration example of the distal portion of the endoscope according to the second embodiment.
Figure 14:
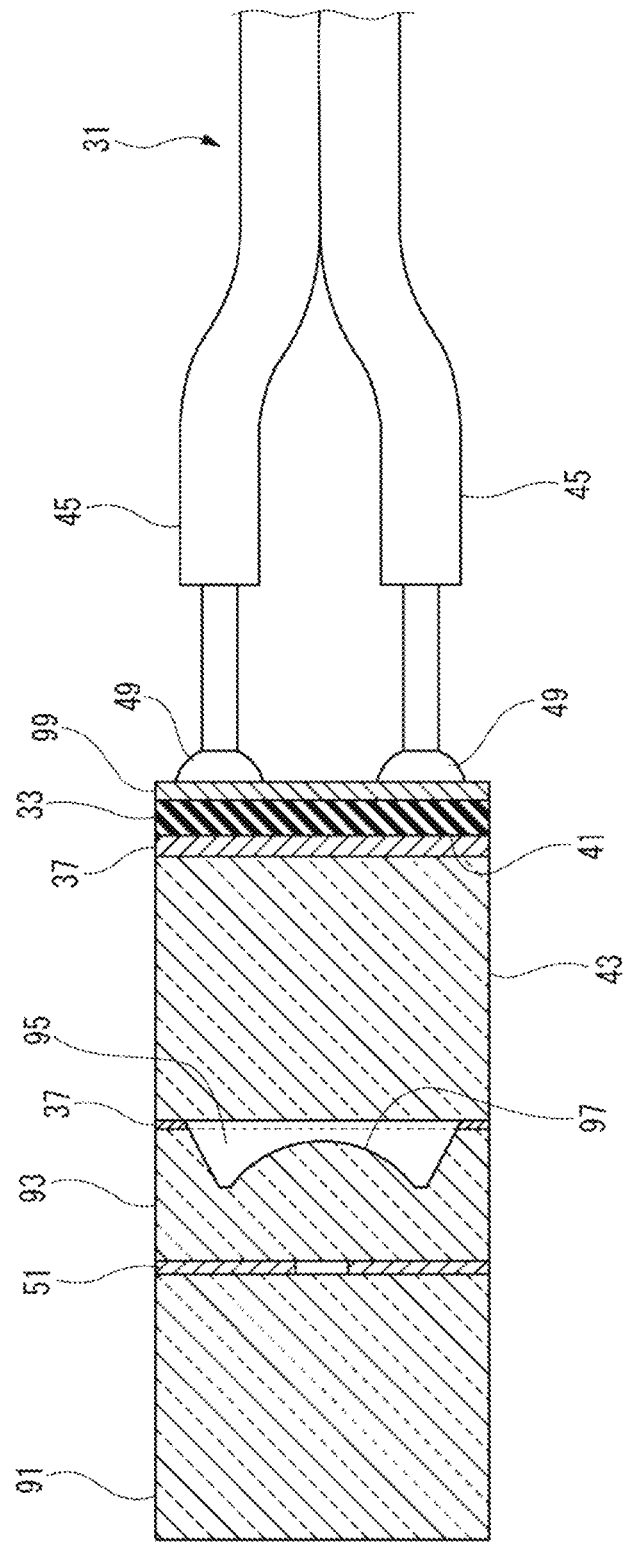
FIG. 14 is a sectional view illustrating a configuration example in a state where a lens and an image sensor in the endoscope according to the second embodiment are directly attached to each other via a bonding resin.
Figure 15:
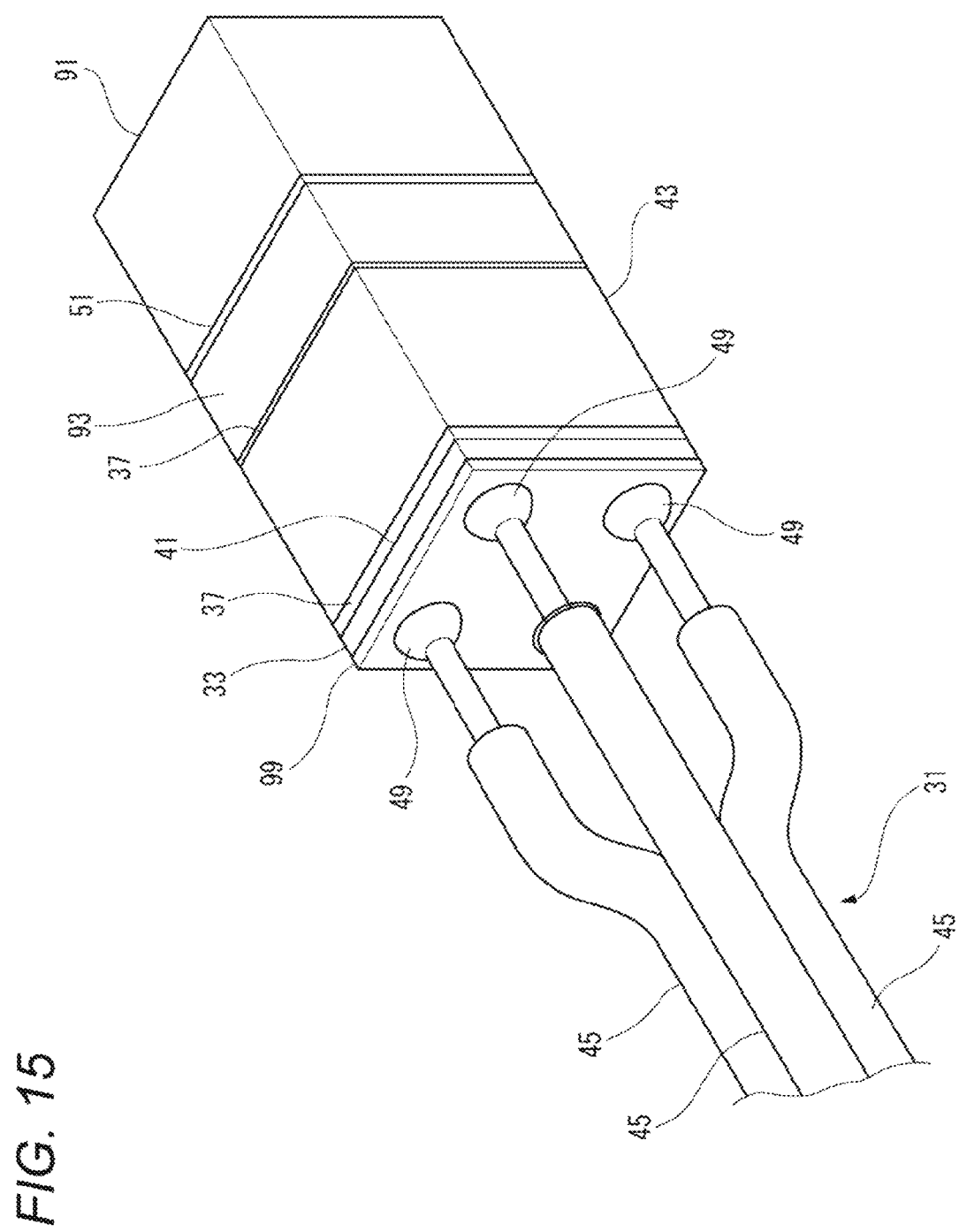
FIG. 15 is a perspective view illustrating a state where the image sensor having a transmission cable connected to a conductor connection part of the endoscope according to the second embodiment is viewed from a rear side.

FIG. 12 is a perspective view illustrating a state where the distal portion of the endoscope 111 according to the second embodiment is viewed from a front side. FIG. 13 is a sectional view illustrating a configuration example of the distal portion of the endoscope 111 according to the second embodiment. FIG. 14 is a sectional view illustrating a configuration example in a state where the lens and the image sensor in the endoscope 111 according to the second embodiment are directly attached to each other via the bonding resin. FIG. 15 is a perspective view illustrating a state where the image sensor having the transmission cable connected to the conductor connection part of the endoscope according to the second embodiment is viewed from a side opposite to the lens unit. In the second embodiment, the same reference numerals will be given to the same members as the members described in the first embodiment, and repeated description thereof will be omitted.

Eleventh Configuration Example

According to the endoscope 111 illustrated in FIG. 12, the maximum exterior diameter Dmax of the distal portion 15 illustrated in FIG. 13 can be formed within a range from the limited diameter to 1.0 mm which corresponds to the diameter of the circumscribed circle of the substrate of the image sensor 33 which can be diced.

In the endoscope 111 according to the present embodiment, as the image sensor 33 whose cross section in the direction perpendicular to the direction of the optical axis has a square shape, those in which a dimension of one side is 0.5 mm or smaller are used. In this manner, in the endoscope 111, a diagonal dimension of the image sensor 33 is approximately 0.7 mm. If the light guide 57 (for example, ($\phi$50 μm) as the lighting means is included therein, the maximum exterior diameter Dmax can be set to 1.0 mm or smaller.

As described above, according to the endoscope 111 of the eleventh configuration example, the maximum exterior diameter Dmax is set to be smaller than 1.0 mm. Accordingly, the endoscope 111 can be more easily inserted into the blood vessel of the human body, for example.

Twelfth Configuration Example

According to the endoscope 111 of a twelfth configuration example, in the endoscope 111 according to the present embodiment, the substrate of the image sensor 33 is formed in a square shape as illustrated in FIG. 15, and the conductor connection parts 49 are respectively arranged at four corners of the substrate of the image sensor 33. One conductor connection part 49 is formed in a circular shape, for example. The four conductor connection parts 49 are respectively arranged at four corners of the square shape. Accordingly, the four conductor connection parts 49 can be arranged so as to be separated from each other as far as the maximum distance.

In the transmission cable 31, each conductor of the power line and the signal line which are the electric cables 45 is covered with an insulating coating material. Among the four electric cables 45, two are laterally arranged, and two are vertically arranged at two stages. The exterior periphery of the insulating coating material is further bundled by an exterior cover, thereby forming one transmission cable 31. In a state where the insulating coating material of each conductor is peeled off, the four conductors are linearly formed parallel to each other. In the electric cables 45, the distal end of the conductor is connected to the conductor connection part 49 by means of soldering. As illustrated in FIG. 13, the image sensor 33 and the transmission cable 31 are covered with the mold resin 17. Accordingly, the conductor connection part 49, the conductors, the insulating coating material of the electric cable 45, and the exterior cover of the transmission cable 31 are embedded in the mold resin 17.

As described above, according to the endoscope 111 of the twelfth configuration example, the four conductor connection parts 49 can be respectively arranged at four corners of the substrate of the image sensor 33. Accordingly, as illustrated in FIG. 15, the four conductor connection parts 49 can be arranged so as to be separated from each other as far as the maximum distance, on the substrate of the square-shaped image sensor 33. In this manner, during a soldering process, two adjacent conductor connection parts 49 are not connected to each other due to the soldering, and it becomes easy to secure an insulating distance. Accordingly, it is possible to easily achieve a small diameter of the distal portion 15. As illustrated in FIG. 15, in the endoscope 11 according to the first embodiment, the four conductor connection parts 49 may be respectively arranged at four corners of the substrate of the image sensor 33.

Thirteenth Configuration Example

As illustrated in FIG. 14, the endoscope 111 according to a thirteenth configuration example includes an objective cover glass 91, the sensor cover glass 43, the image sensor 33 whose imaging area 41 is covered with the sensor cover glass 43, the lens 93 that is interposed between the objective cover glass 91 and the sensor cover glass 43, and in which the optical axis of the single lens is coincident with the center of the imaging area 41, the iris 51 that is disposed between the objective cover glass 91 and the lens 93, the bonding resin 37 that fixes the lens 93 and the sensor cover glass 43, and an air layer 95 that is disposed between the lens 93 and the sensor cover glass 43.

In the endoscope 11 according to the first embodiment, the separation portion 47 having a limited width between the last lens L3 among three lenses and the sensor cover glass 43 is coated with the bonding resin 37, thereby directly attaching the lens L3 and the sensor cover glass 43 to each other. On the other hand, in the endoscope 111 according to the second embodiment, the lens 93 and the sensor cover glass 43 are directly attached to each other via the bonding resin 37. As a result, in the endoscope 111, the bonding resin 37 has substantially a linear shape in a side view (refer to FIG. 15). In the endoscope 111 according to the second embodiment, the lens 93 and the sensor cover glass 43 are directly attached to each other via by the bonding resin 37 in an edge portion on both end sides of the lens 93. Only the edge portion is coated with the bonding resin 37.

For example, the lens 93 is a single lens. An exterior shape thereof is formed in a prismatic shape which is the same as that of the image sensor 33, and cross section in the direction perpendicular to the direction of the optical axis has a square shape. The lens 93 causes the incident light reflected from an imaging subject and passing through the objective cover glass 91 to form an image on the imaging area 41 of the image sensor 33 via the sensor cover glass 43. A concave portion is formed on a surface on the sensor cover glass 43 side of the lens 93. A convex curved surface portion 97 protruding in a substantially spherical shape is formed on a bottom surface of the concave portion. The lens 93 has a function as an optical element to focus the light by using the convex curved surface portion 97. A protruding distal end of the convex curved surface portion 97 is slightly separated from a portion between the lens 93 and the sensor cover glass 43. On the other hand, in the lens 93, a square and annular end surface surrounding the concave portion is bonded to the sensor cover glass 43 by the bonding resin 37. In this manner, the concave portion between the lens 93 and the sensor cover glass 43 is in an air-sealing state. The sealing air in the concave portion serving as a sealed space is preferably dried air. Nitrogen may seal the concave portion. In this way, the air layer 95 whose internal volume is set in the concave portion is formed between the lens 93 and the sensor cover glass 43. The convex curved surface portion 97 is arranged in the air layer 95. That is, in the lens 93, a light-emitting surface of the convex curved surface portion 97 is in contact with the air.

In the endoscope 111 in which the maximum exterior diameter Dmax is 1.0 mm, whether or not the number of lenses can be reduced is an important factor for reducing the diameter. Accordingly, in a case where the lens 93 serving as the single lens is disposed in the endoscope 111, it is important how to provide a refractive index between the lens 93 and the sensor cover glass 43, in a very small region in the width direction parallel to the direction of the optical axis. In the endoscope 111 according to the thirteenth configuration example, the air layer which can obtain a great refractive index difference between the lens 93 and the sensor cover glass 43 is disposed on an optical element surface.

As described above, according to the endoscope 111 of the thirteenth configuration example, the concave portion is formed in the lens 93, the convex curved surface portion 97 is formed on the bottom surface, and the square and annular end surface is boned to the sensor cover glass 43. Accordingly, it is possible to secure the air layer 95 for increasing the refractive index of the lens 93. At the same time, the optical axis of the lens 93 can be easily aligned with the imaging area 41. Since the lens 93 can secure the air layer 95, it is possible to obtain great lens power between the lens 93 and the sensor cover glass 43. In this manner, one lens can be reduced in the endoscope 111. As a result, it is possible to provide the miniaturized and cost-reduced endoscope 111.

Fourteenth Configuration Example

Figure 16:
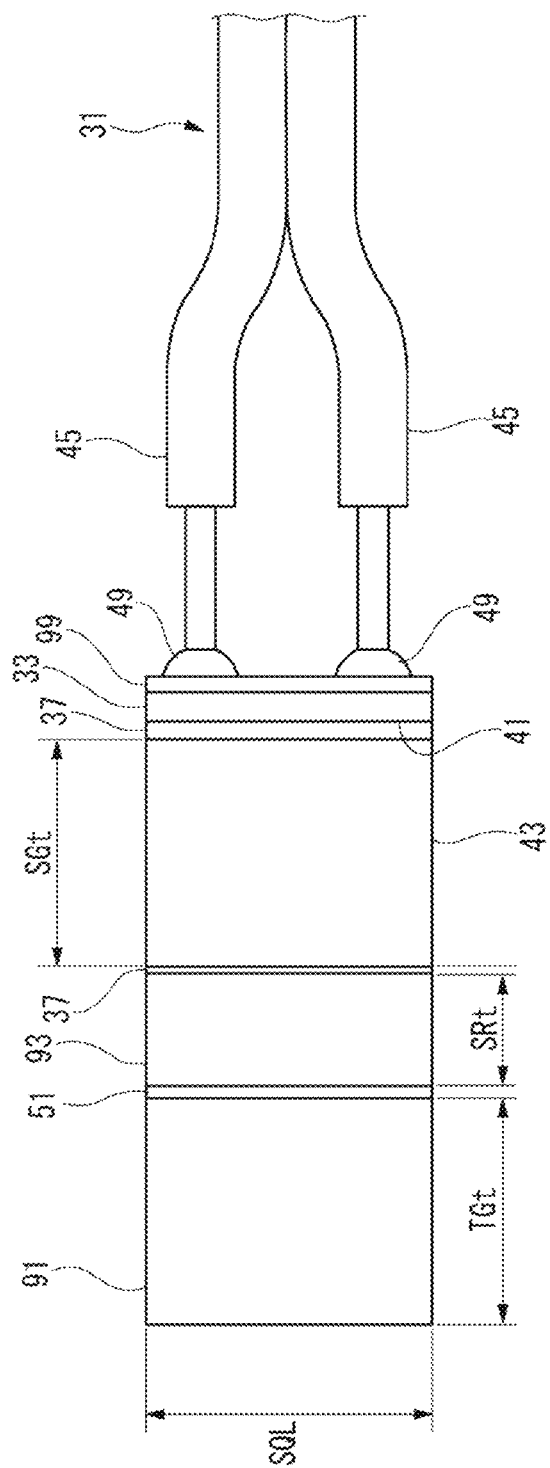
FIG. 16 is a side view illustrating an example of dimensions of an objective cover glass, a lens, and a sensor cover glass.

FIG. 16 is a side view illustrating an example of dimensions of the objective cover glass, the lens, and the sensor cover glass. In the endoscope 111 according to a fourteenth configuration example, in the endoscope 111 according to the present embodiment, a thickness TGt in the direction along the optical axis of the objective cover glass 91, a thickness SRt of the lens 93, and a thickness SGt of the sensor cover glass 43 are all formed within a range from 0.1 to 0.5 mm. The objective cover glass 91, the lens 93, the sensor cover glass 43, and the image sensor 33 have a square shape in which a length SQL of one side of the square shape of the cross section perpendicular to the direction of the optical axis is 0.5 mm. The image sensor 33 illustrated in FIGS. 13 to 16 is illustrated by providing the thickness for the electric circuit 99, and is illustrated by providing the thickness for the bonding resin 37 bonding the sensor cover glass 43 and the image sensor 33 to each other.

In accordance with the focal length and the optical characteristics of the lens 93, the sensor cover glass 43 has a function to hold a distance between the lens 93 and the imaging area 41. The sensor cover glass 43 is easily adjusted, since the thickness SGt is set within a range from 0.1 to 0.5 mm.

The lens 93 can function as the optical element and can secure the air layer 95, since the thickness SRt is set within a range from 0.1 to 0.5 mm.

The objective cover glass 91 can be used alone without using other reinforcing members, since the thickness TGt is set within a range from 0.1 to 0.5 mm. It is possible to prevent a viewing angle from being narrowed due to light beams rejected by the unnecessarily increased thickness.

As described above, according to the endoscope 111 of the fourteenth configuration example, a suitable distance is held between the lens 93 and the image sensor 33, while the air layer 95 is easily secured. It is possible to prevent the viewing angle from being narrowed. Moreover, it is possible to prevent an increase in the dimensions in the direction along the optical axis from the objective cover glass 91 to the image sensor 33.

Fifteenth Configuration Example

In the endoscope 111 according to the present embodiment, as illustrated in FIG. 13, the endoscope 111 according to a fifteenth configuration example includes the molded part 65 in which an exterior peripheral surface other than an objective surface of the objective cover glass 91, an exterior peripheral surface of the lens 93, and the image sensor 33 are coated with and fixed by the mold resin 17, and in which an exterior shell of the distal portion 15 is formed and exposed outward, and the tubular sheath 61 which is formed to have the same exterior diameter as that of the distal portion 15, and which is connected by covering at least a portion of the molded part 65.

The sheath 61 is formed of a flexible resin material as described above. In order to provide strength for the sheath 61, the sheath 61 can include a single wire on the inner peripheral side, multiple lines, and a braided tensile strength wire. A material of the tensile strength wire is as described above.

In the endoscope 111, the objective cover glass 91, the lens 93, the sensor cover glass 43, the overall image sensor 33, a portion of the transmission cable 31, and a portion of the light guide 57 are coated with and fixed by the mold resin 17, and the mold resin 17 is exposed outward. The distal portion 15 of the endoscope 111 may include an X-ray opaque marker. In this manner, the endoscope 111 easily checks a distal position under X-ray fluoroscopy.

In the endoscope 111, the objective cover glass 91, the lens 93, the sensor cover glass 43, the image sensor 33, a portion of the transmission cable 31, and a portion of the light guide 57 (imaging unit) are coated with and fixed by the mold resin 17. Accordingly, a small number of interposing components is disposed when these members are fixed to each other. In this manner, the distal portion 15 of the endoscope 111 can have a small diameter. Even in a case where the diameter of the distal portion 15 is further reduced, a configuration having the minimum dimension can be adopted. In addition, the component cost can be reduced. For example, it is possible to realize the endoscope 111 applicable so that the endoscope 111 can image a very thin lesion site such as the blood vessel of the human body. As a result, it is possible to provide the miniaturized and cost-reduced endoscope 11.

The molded resin 17 is molded from the image sensor 33 to the objective cover glass 91, thereby contributing to increased fixing strength of the imaging units. The mold resin 17 also improves air-tightness (that is, few minor gaps), water-tightness, and light blocking performance of the air layer 95. Furthermore, the mold resin 17 also improves the light blocking performance when the optical fiber 59 for light guide 57 is embedded therein.

In the distal portion 15 of the endoscope 111, the light guide 57 is molded by the mold resin 17. The light guide 57 is caused to act as a structural member. Accordingly, even in the small-diameter endoscope 111, it is possible to improve connection strength between the flexible portion 29 and the distal portion 15. In addition, in the endoscope 111, in a case where the distal portion 15 is viewed from the exterior most surface on the insertion side (refer to FIG. 12), the mold resin 17 coats the objective cover glass 91 of the distal portion 15 and the four optical fibers 59 together. Thus, there is no clearance around each of the objective cover glass 91 and the four optical fibers 59 (that is, no gap around each of them). Accordingly, if the endoscope 111 is subjected to sterilization (that is, cleaned) after being used during the inspection or the surgery, this reduces possibilities that cleaning remnants such as unnecessary liquids may adhere to the endoscope 111. Therefore, compared to the endoscope 11 according to the first embodiment, the endoscope 111 can be more conveniently used in terms of hygiene when the endoscope 111 is used for the subsequent inspection or surgery.

According to the endoscope 533 in the related art disclosed in WO2013/146091, the axis of the distal portion and the optical axis of the lens unit 547 are eccentric with each other. Therefore, a distance to an imaging subject is likely to vary due to a rotation angle of the distal portion, and it is difficult to stably obtain a satisfactory image. Furthermore, if the axis of the distal portion and the optical axis of the lens unit 547 are eccentric with each other, an interference condition between a tube inner wall and the distal portion varies due to the rotation angle of the distal portion, thereby degrading operability particularly when the distal portion enters a thin hole. In contrast, according to the endoscope 111, the objective cover glass 91, the lens 93, the sensor cover glass 43, and the image sensor 33 are coaxially continuous with each other. That is, the objective cover glass 91 is arranged so as to be concentric with the distal portion 15. As a result, according to the endoscope 111 in the fifteenth configuration example, a small diameter is likely to be achieved, a satisfactory image can be stably obtained, and insertion operability can be improved.

Sixteenth Configuration Example

In the endoscope 111 according to a sixteenth configuration example, it is preferable that the thickness of the sheath 61 is set within a range from 0.1 to 0.3 mm.

The molded part 65 of the endoscope 111 has the small-diameter extension portion 71 (illustrated in FIG. 13) which extends rearward from the rear end covering the image sensor 33. The small-diameter extension portion 71 is formed in a columnar shape, and has the four optical fibers 59 embedded therein. The small-diameter extension portion 71 has the transmission cable 31 embedded inside the four optical fibers 59. The inner diameter side of the sheath 61 is fixed to the exterior periphery of the small-diameter extension portion 71 by using an adhesive. That is, the molded part 65 and the sheath 61 are continuous with each other so as to coaxially have the maximum exterior diameter Dmax of 1.0 mm.

As described above, according to the endoscope 111 of the sixteenth configuration example, the thickness of the sheath 61 can be as thick as 0.3 mm. Accordingly, it becomes easy to increase tensile strength of the sheath 61. The minimum exterior diameter of the transmission cable 31 is currently approximately 0.54 mm. In a case where the maximum exterior diameter Dmax of the distal portion 15 is set to 1.0 mm, the thickness of the sheath 61 is 0.23 mm. In this manner, in the endoscope 111, the thickness of the sheath 61 is set to within a range from 0.1 to 0.3 mm as described above. Accordingly, the maximum exterior diameter Dmax of the distal portion 15 can be set to 1.0 mm.

Seventeenth Configuration Example

Figure 17A:
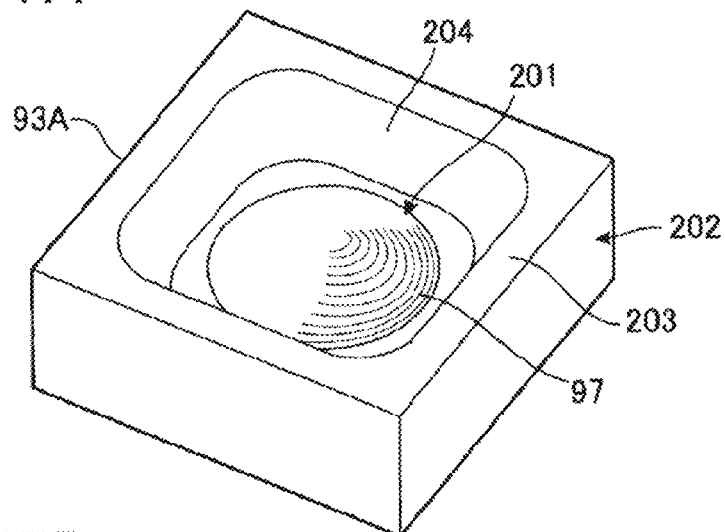
FIG. 17A is a view illustrating a first example of a lens shape in the endoscope according to the second embodiment.
Figure 17B:
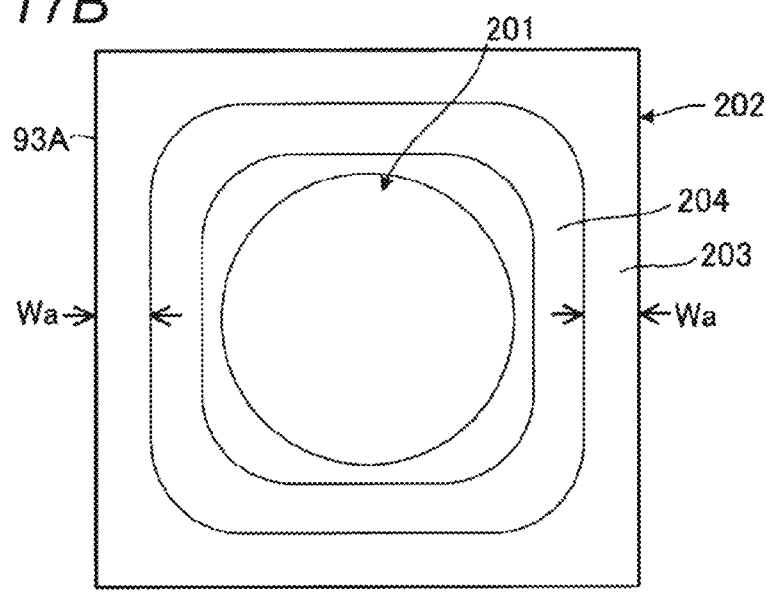
FIG. 17B is a view illustrating the first example of the lens shape in the endoscope according to the second embodiment.
Figure 17C:
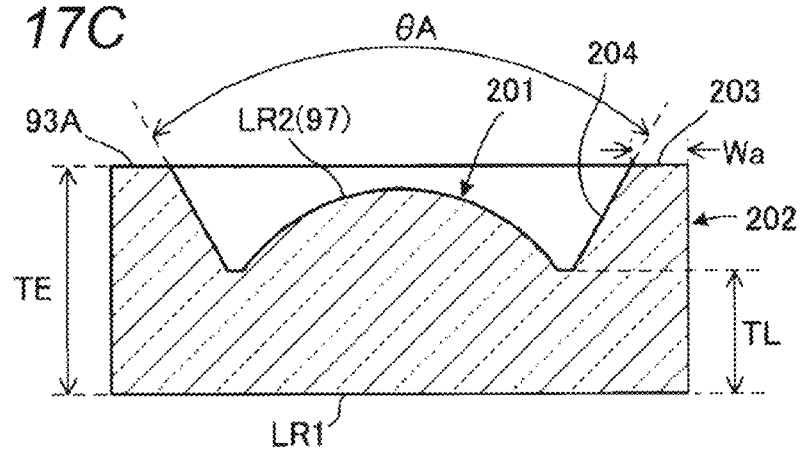
FIG. 17C is a view illustrating the first example of the lens shape in the endoscope according to the second embodiment.

According to a seventeenth configuration example, as a specific configuration example of the lens 93 in the endoscope 111, the configuration example shows a lens shape. FIGS. 17A, 17B, and 17C illustrate a first example of the lens shape.

A lens 93A in the first example is configured to include a single lens in which a first surface LR1 on the imaging subject side has a plane and a second surface LR2 on the imaging side has a convex surface. On the imaging side of the lens 93A, the central part has an optical element part 201 holding the convex curved surface portion 97 which protrudes in a substantially spherical shape configuring the lens surface of the second surface LR2 having the convex surface and which has a circular dome shape. The peripheral edge part has an integrally formed edge portion 202 serving as a frame body which has a bonding plane 203 whose end surface is a plane. The edge portion 202 has a shape in which the dimension in the thickness direction (direction of the optical axis) is greater than that of the center portion of the convex curved surface portion 97 of the optical element part 201 and the bonding plane 203 of the edge portion 202 protrudes from the convex curved surface portion 97. The edge portion 202 is a portion which is fixed to the sensor cover glass 43 by the bonding resin 37 adhering to the bonding plane 203. The bonding plane 203 of the edge portion 202 has a substantially square shape in which the exterior peripheral portion has a square shape and the inner peripheral portion has a substantially square shape whose corners are rounded. In the bonding plane 203 of the edge portion 202, a bonding width Wa of an equal width portion of four sides is 50 μm or greater, for example. The inner side of the edge portion 202 has the air layer 95 between the convex curved surface portion 97 serving as the lens surface of the second surface LR2 and the sensor cover glass 43.

For example, the dimension (thickness SRt) in the thickness direction of the lens 93A is 100 μm to 500 μm. In the illustrated example, a thickness TE of the edge portion 202 is 200 μm, and a thickness TL up to the first surface LR1 in the exterior peripheral portion of the convex curved surface portion 97 (second surface LR2) of the optical element part 201 is 110 μm to 120 μm. From the exterior peripheral portion of the convex curved surface portion 97 of the optical element part 201 to the inner peripheral portion of the bonding plane 203 of the edge portion 202, the lens 93A has an inclined plane 204 extending from the lens center to the exterior periphery. For example, an angle θA of the inclined plane 204 represents θA=60°, if an angle of an opening is set to θA when viewed from the lens center.

Figure 18A:
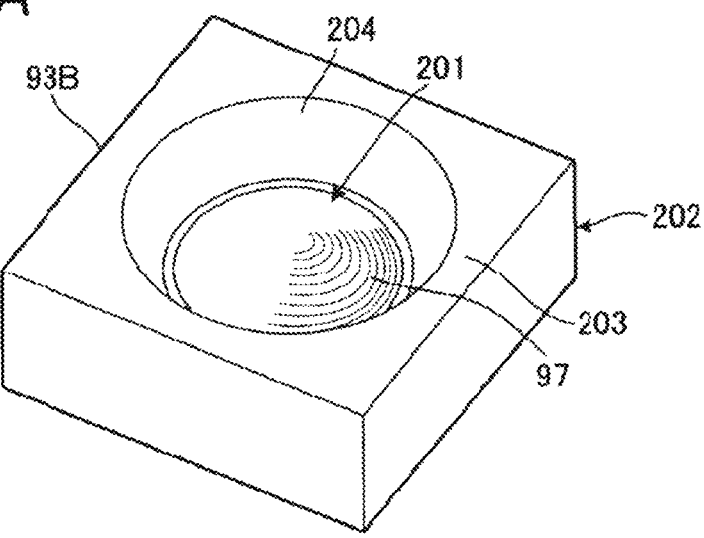
FIG. 18A is a view illustrating a second example of a lens shape in the endoscope according to the second embodiment.
Figure 18B:
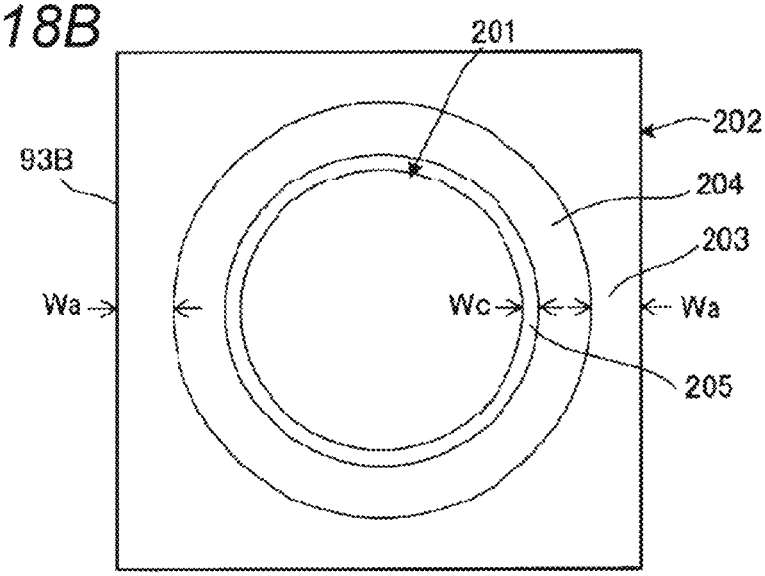
FIG. 18B is a view illustrating the second example of the lens shape in the endoscope according to the second embodiment.
Figure 18C:
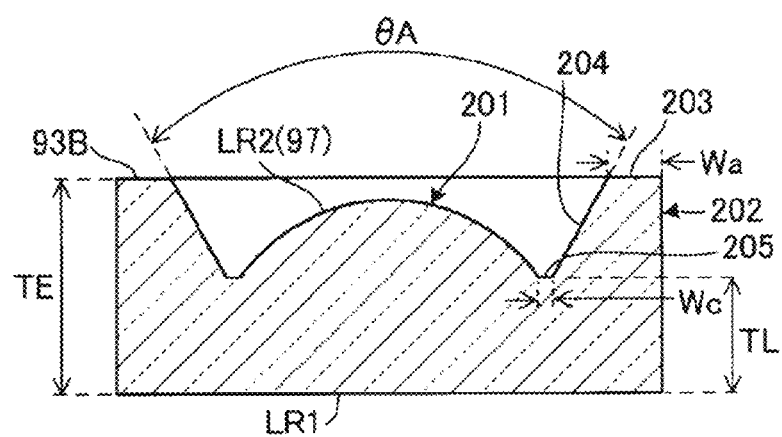
FIG. 18C is a view illustrating the second example of the lens shape in the endoscope according to the second embodiment.

FIGS. 18A, 18B, and 18C are views illustrating a second example of the lens shape. In a lens 93B in the second example, on the imaging side of the lens 93B, the central part has the optical element part 201 holding the convex curved surface portion 97 which protrudes in a substantially spherical shape configuring the lens surface of the second surface LR2 having the convex surface and which has a circular dome shape. The peripheral edge part has an integrally formed edge portion 202 serving as a frame body which has the bonding plane 203 whose end surface is a plane. Here, configurations which are different from those in the first example will be mainly described, and description of the configurations which are the same as those in the first example will be omitted. The bonding plane 203 of the edge portion 202 has a circular shape which is concentric with the convex curved surface portion 97 whose exterior peripheral portion has a square shape and whose inner peripheral portion has a circular dome shape. The bonding width Wa of the minimum portion is 50 μm, for example. A width We of a plane portion 205 formed in the exterior peripheral portion of the convex curved surface portion 97 (second surface LR2) of the optical element part 201 is 13 μm, for example. From the plane portion 205 of the exterior peripheral portion of the optical element part 201 to the inner peripheral portion of the bonding plane 203 of the edge portion 202, the lens 93B has the inclined plane 204 extending from the lens center to the exterior periphery. For example, the angle θA of the inclined plane 204 represents θA=60°, if the angle of the opening is set to θA when viewed from the lens center.

Figure 19A:
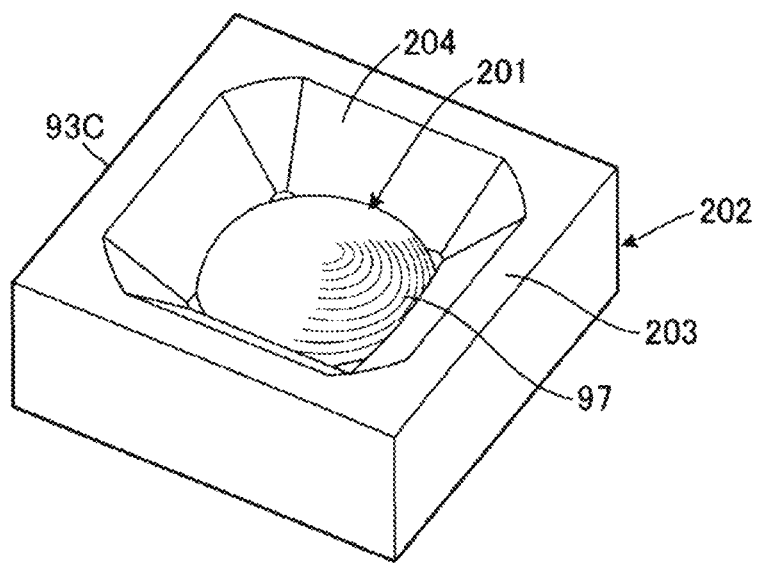
FIG. 19A is a view illustrating a third example of a lens shape in the endoscope according to the second embodiment.
Figure 19B:
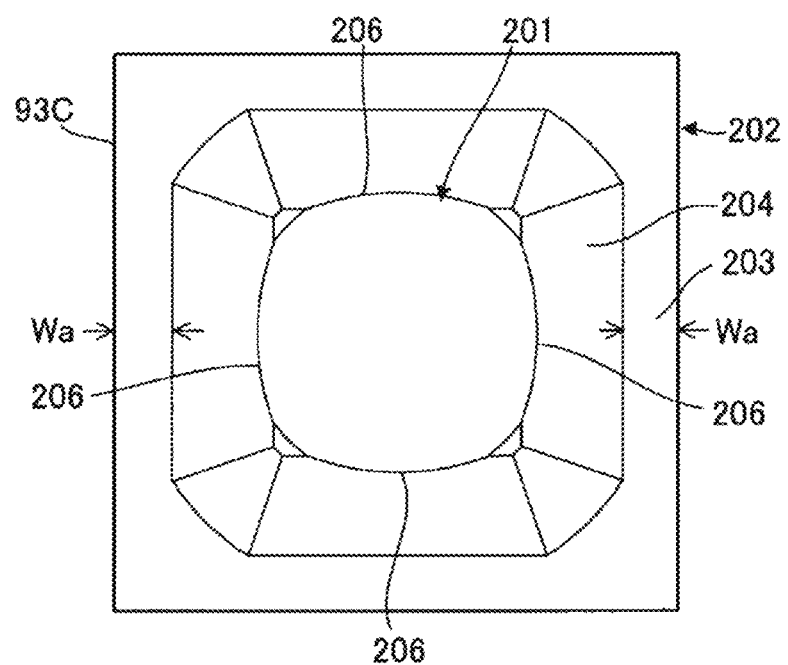
FIG. 19B is a view illustrating the third example of the lens shape in the endoscope according to the second embodiment.
Figure 19C:
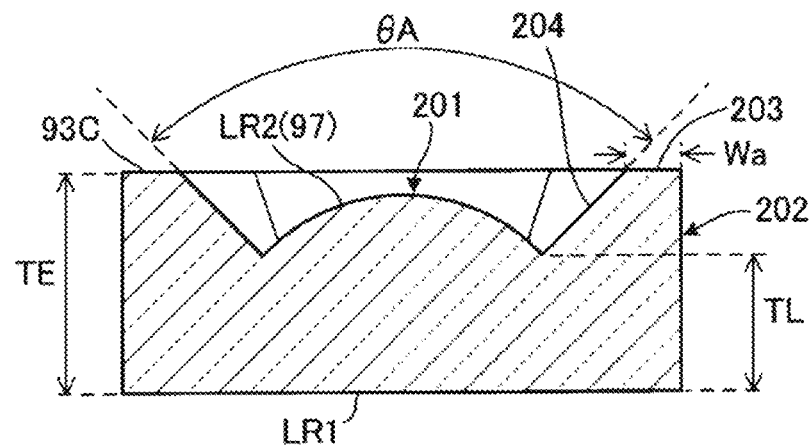
FIG. 19C is a view illustrating the third example of the lens shape in the endoscope according to the second embodiment.
Figure 19D:
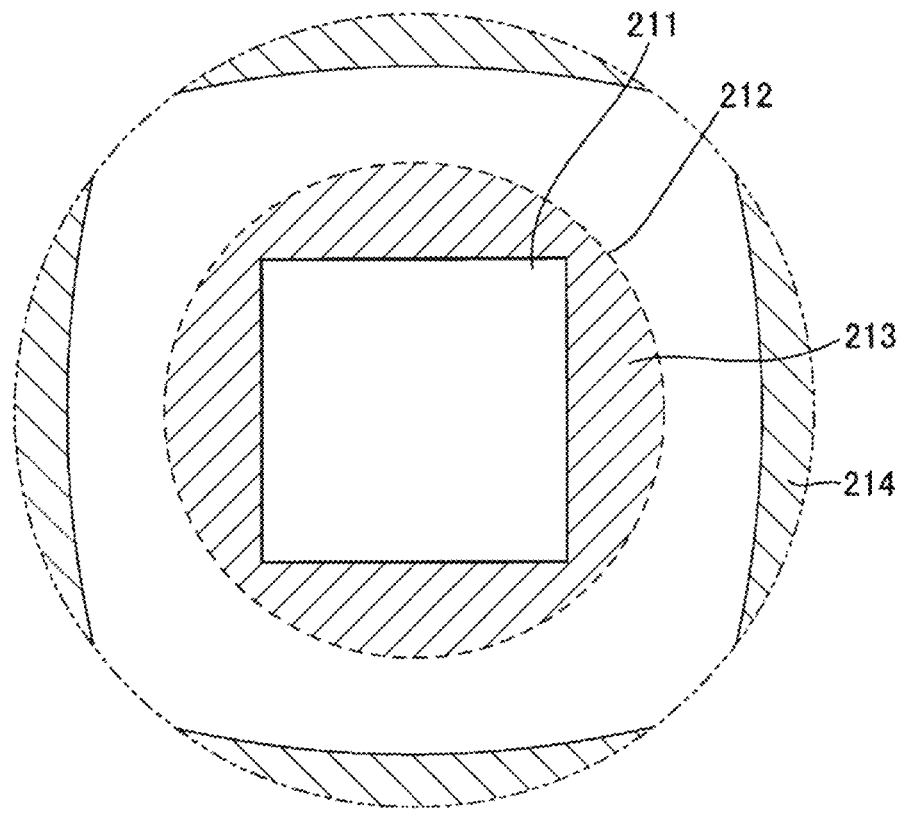
FIG. 19D is a view illustrating the third example of the lens shape in the endoscope according to the second embodiment.

FIGS. 19A, 19B, 19C, and 19D are views illustrating a third example of the lens shape. In a lens 93C in the third example, on the imaging side of the lens 93C, the central part has the optical element part 201 holding the convex curved surface portion 97 which protrudes in a substantially spherical shape configuring the lens surface of the second surface LR2 having the convex surface and which has a circular dome shape. The peripheral edge part has the integrally formed edge portion 202 serving as a frame body which has the bonding plane 203 whose end surface is a plane. Here, configurations which are different from those in the first example will be mainly described, and description of the configurations which are the same as those in the first example will be omitted. The optical element part 201 of the central part has a barrel shape in which four circumferential portions 206 corresponding to four sides of the square exterior shape of the lens are partially notched in an exterior peripheral portion of the convex curved surface portion 97 having the circular dome shape. The edge portion 202 of the peripheral edge part has the inclined plane 204 from the inner peripheral portion of the bonding plane 203 to the exterior peripheral portion of the barrel-shaped optical element part 201. As illustrated in FIG. 19D, the lens 93C in the third example has a shape in which an unnecessary portion of an image circle 212 of the circular lens 93C, that is, four exterior peripheral regions 214 on which a light beam for forming an image in a region 213 outside the four sides of the imaging area 211 is incident are cut from the imaging area 211 of the square image sensor 33. For example, the angle θA of the inclined plane 204 of the inner peripheral portion of the edge portion 202 represents θA=90°, if the angle of the opening is set to θA when viewed from the lens center. Compared to the first example and the second example, the inclined plane 204 can be more gently formed. On the other hand, similarly to the first example and the second example, if the angle θA of the inclined plane 204 of the inner peripheral portion of the edge portion 202 is set to θA=60°, it is possible to further increase the bonding width Wa of the bonding plane 203 of the edge portion 202.

For example, the lens 93 is manufactured by means of nano-imprint lithography or injection molding. The lens 93 is manufactured in such a way that a mold using an original in the nano-imprint lithography is used so as to form a lens group in which multiple small lenses having the same shape are arrayed, the lens group as a molded product is released from the mold, and thereafter the lens group is cut into individual lenses by means of dicing. When the lens 93 is manufactured, it is necessary to provide a draft angle in order to remove the lens 93 from the mold. The inclined plane 204 of the lens 93 functions as the draft angle. The draft angle of the molded product is preferably as large as possible in order to easily remove the molded product from the mold. Accordingly, in view of the removability, it is desirable that the inclined plane 204 of the lens 93 is gentle with respect to a surface perpendicular to the optical axis of the lens 93. On the other hand, in order to decrease the exterior dimension of the lens 93, it is preferable to erect the inclined plane 204 of the lens 93 as much as possible. In a case where the lens 93 is bonded to the sensor cover glass 43 by using the bonding resin 37, in view of the bonding strength, it is preferable that the bonding plane 203 of the edge portion 202 to which the bonding resin 37 adheres have a bonding plane as large as possible.

Therefore, while respective factors such as the small diameter, the removability, and the bonding strength of the lens 93 are comprehensively considered, the dimension of the bonding plane 203 of the edge portion 202 is set so that the lens 93 and the sensor cover glass 43 can be reliably bonded to each other in the edge portion 202. For example, as an example of the size of the lens 93 whose exterior shape is a quadrangular prism shape, in a case where a dimension of one side of a square shape of a cross section perpendicular to the direction of the optical axis is 0.5 mm, the bonding plane 203 of the edge portion 202 is set to have the bonding width Wa of 50 µm or greater, for example. In this case, in the endoscope 111 in which the maximum exterior diameter Dmax of the distal portion 15 is set to 1.0 mm or smaller, a dimension of one side of the exterior shape of the lens 93 is set to 0.5 mm or smaller. In this manner, the bonding width Wa of the bonding plane 203 in the edge portion 202 is secured to be 50 µm or greater. In order to compatibly achieve the small diameter and the removability of the lens 93, the angle θA of the inclined plane 204 is set to 60°≤θA≤90°, if the angle of the opening is set to θA when viewed from the lens center. In this case, the angle of the inclined plane 204 is 30° to 45° with respect to the direction of the optical axis of the lens 93 (direction parallel to the removal direction), and is 60° to 45° with respect to the surface perpendicular to the optical axis of the lens 93.

As described above, according to the endoscope 111 of the seventeenth configuration example, it is possible to realize the small-diameter lens 93 in which the maximum exterior diameter Dmax of the distal portion 15 can be set to 1.0 mm or smaller. In the lens 93 allowed to have the small diameter, the bonding width Wa of the bonding plane 203 of the edge portion 202 is set to 50 µm or greater. In this manner, the lens 93 and the sensor cover glass 43 can be reliably bonded and fixed to each other. As the angle of the inclined plane 204 between the optical element part 201 of the central part and the edge portion 202 of the peripheral edge part in the lens 93, the angle θA of the opening when viewed from the lens center is set to 60°≤θA≤90°. Accordingly, it is possible to improve the removability when the lens is manufactured.

Eighteenth Configuration Example

An eighteenth configuration example shows a configuration example of the bonding plane between the lens 93 and the sensor cover glass 43 in the endoscope 111.

Figure 20:
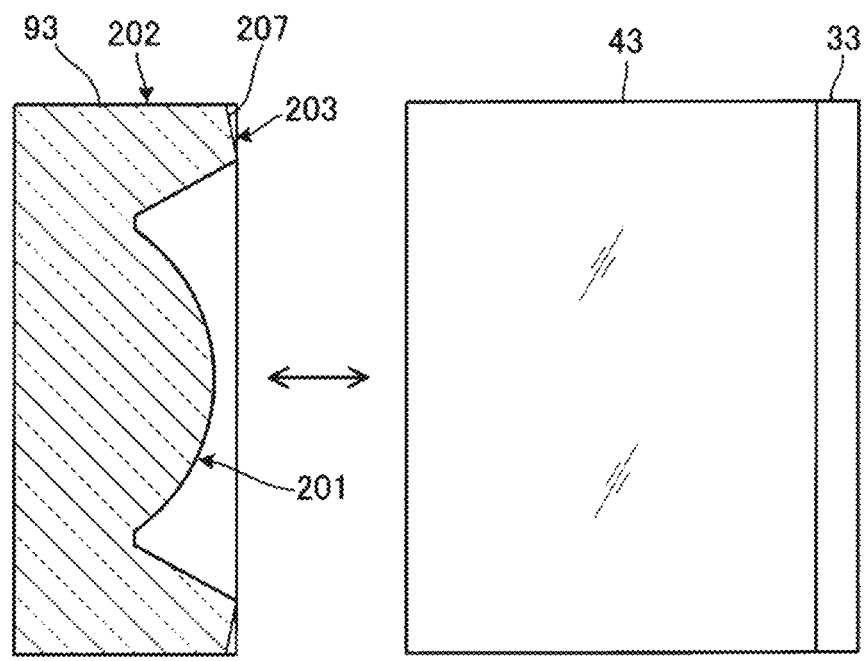
FIG. 20 is a view illustrating a configuration example of a bonding plane with a sensor cover glass in the lens of the endoscope according to the second embodiment.

FIG. 20 is a view illustrating the configuration example of the bonding plane with a sensor cover glass 43 in the lens 93. In the lens 93, the exterior shape of a quadrangular prism shape is coincident with the sensor cover glass 43 of the image sensor 33, and is bonded by using the bonding resin 37. In this manner, it is possible to fix both of these by easily aligning the optical axis with the imaging area 41 of the image sensor 33. The bonding plane 203 of the edge portion 202 of the lens 93 may have an inclined portion 207 which is inclined so as to have a predetermined angle instead of a plane parallel to an end surface of the sensor cover glass 43, in a state of facing each other for being bonded and fixed to the sensor cover glass 43. The inclined portion 207 of the bonding plane 203 has a tapered shape which is inclined in a direction to the exterior peripheral portion from the inner peripheral portion of the edge portion 202, and the thickness dimension of the exterior peripheral portion is slightly smaller. For example, an inclined angle of the inclined portion 207 of the bonding plane 203 is set to 0.5° or greater. In a case where the bonding plane 203 of the edge portion 202 is slightly coated with the bonding resin 37 in order to bond the lens 93 to the sensor cover glass 43, due to the inclined portion 207 of the bonding plane 203, the bonding resin 37 on the bonding plane is likely to move to the exterior peripheral side, and is less likely to enter the inside of the edge portion 202. Accordingly, it is possible to prevent the bonding resin 37 from interfering with the air layer 95 formed in the optical element part 201.

As described above, according to the endoscope 111 of the eighteenth configuration example, it is possible to prevent the bonding resin 37 from entering the air layer 95 between the lens 93 and the sensor cover glass 43. While the air layer 95 is secured, it is possible to reliably bond and fix the lens 93 and the sensor cover glass 43 to each other.

Nineteenth Configuration Example

A nineteenth configuration example shows a specific configuration example of an optical system in the endoscope 111.

Hereinafter, the specific configuration example of the optical system including the objective cover glass 91, the lens 93, and the sensor cover glass 43 will be described.

Objective Cover Glass 91

Thickness TGt of objective cover glass 91: TGt=0.1 to 0.5 mm

Example of material of objective cover glass 91: BK7 (manufactured by Schott AG), nd=1.52, vd=64.2

Refractive index ndF of objective cover glass 91: 1.3≤ndF

Abbe number vdF of objective cover glass 91: 30≤vdF

Sensor Cover Glass 43

Thickness SGt of sensor cover glass 43: SGt=0.1 to 0.5 mm

Example of material of sensor cover glass 43: BK7 (manufactured by Schott AG), nd=1.52, vd=64.2

Refractive index ndR of sensor cover glass 43: 1.3≤ndR≤2.0, ndF≤ndR

Abbe number vdR of sensor cover glass 43: 40≤vdR, vdF≤vdR

Lens 93

Focal length f of lens 93: 0.1 mm≤f≤1.0 mm

F-number FNO of lens 93: 1.4≤FNO≤8.0

Figure 21:
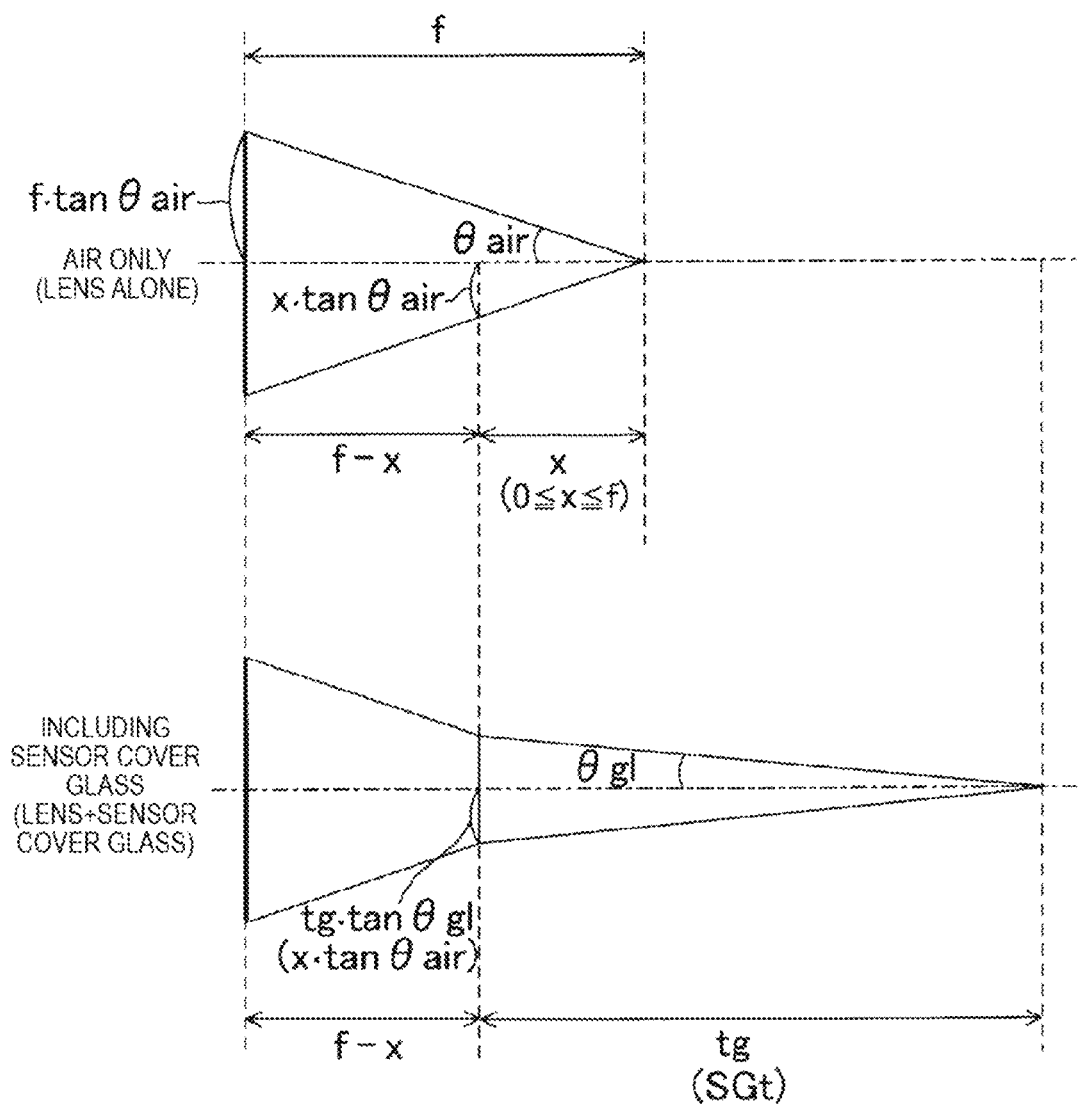
FIG. 21 is a view for describing a relationship between a focal length of the lens and a thickness of the sensor cover glass in the endoscope according to the second embodiment.

FIG. 21 is a view for describing a relationship between the focal length f of the lens 93 and a thickness tg (=SGt) of the sensor cover glass 43. In FIG. 21, f represents the focal length of the lens 93, x represents a distance from an imaging forming point on the imaging side to an end surface on the imaging subject side of the sensor cover glass 43 in the focal length of the lens 93, and tg represents the thickness SGt of the sensor cover glass 43. In addition, θair represents the maximum angle of a light beam emitted to the image forming point from the lens 93 in a state of air only (case of the lens alone) with respect to the optical axis (angle formed between the light beam connecting the image forming point in the air from an exit pupil of the lens and the optical axis). θgl represents the maximum angle of the light beam emitted to the image forming point through the sensor cover glass 43 from the lens 93 in a state including the sensor cover glass 43 (case of the lens+the sensor cover glass) with respect to the optical axis (angle formed between the light beam connecting the image forming point in a state including the air and the sensor cover glass from the exit pupil of the lens and the optical axis). Here, x represents 0≤x≤f. A distance from the exit pupil of the lens 93 to an end surface on the imaging subject side of the sensor cover glass 43 shows f–x.

A relationship between the F-number FNO of the lens 93 and the number of openings (numerical apertures) NA is $FNO=1/(2 \cdot NA)$.

Accordingly, FNO=1/(2·sin θair) is satisfied. Therefore, the following relationship of Expression (1) is obtained.

$\sin θair=1/(2 \cdot FNO)$ $$θair=\sin^{-1}\{1/(2 \cdot FNO)\} \qquad (1)$$

In addition, according to the Snell's law,

1·sin θair=ngl·sin θgl is satisfied.

Therefore, the following relationship of Expression (2) is obtained.

$\sin θgl=(\sin θair)/ngl=1/(2 \cdot FNO \cdot ngl)$ $$θgl=\sin^{-1}\{1/(2 \cdot FNO \cdot ngl)\} \qquad (2)$$

In FIG. 21, a radius of the exit pupil of the lens 93 is f·tan θair. In a state of the air only with the lens alone, with regard to the light beam connecting the image forming point in the air from the exit pupil of the lens 93, a distance to the optical axis at a position on an end surface on the imaging subject side of the sensor cover glass 43 is x·tan θair. In addition, in a state including the lens 93 and the sensor cover glass 43, with regard to the light beam connecting the image forming point in a state including the air and the sensor cover glass 43 from the exit pupil of the lens 93, a distance to the optical axis on an end surface on the imaging subject side of the sensor cover glass 43 is tg·tan θgl. Here, x·tan θair=tg·tan θgl is satisfied. Accordingly, the thickness tg of the sensor cover glass 43 is obtained by Expression (3) in the following.

$$tg=x \cdot \tan θair \times (1/\tan θgl)=x \cdot (\tan θair)/(\tan θgl) \qquad (3)$$

Therefore, in a case where the thickness tg (=SGt) of the sensor cover glass 43 is set to 0.1 mm≤tg≤0.5 mm, x is set as a parameter, and a combination of f, FNO, and ngl (=ndR), which satisfies a relationship of Expression (4) in the following, may be obtained from Expressions (1) and (2). The combination may be set as a numerical value of the optical characteristics of the lens 93 and the sensor cover glass 43.

$$0.1 \leq x \cdot (\tan θair)/(\tan θgl) \leq 0.5 \qquad (4)$$

Here, tan θair and tan θgl are obtained from sin θair and sin θgl. Accordingly, tan θair and tan θgl can be expressed by FNO and ngl.

Next, description will be made with regard to a specific example of the combination of f, FNO, and ngl (=ndR) in a case where the thickness tg (=SGt) of the sensor cover glass 43 is set to tg=0.40 mm as the optical characteristics of the lens 93 and the sensor cover glass 43. In the following example, BF represents a back focus (distance from the lens center (position of the exit pupil) to the image forming point (imaging area of the image sensor)), and is adjusted by a distance between the lens 93 and the sensor cover glass 43.

(1) Aerial Long Distance (f, FNO, ndR)=(0.306, 4.01, 1.5168), BF=0.0125

In the endoscope, an aerial long distance corresponds to observation of the bronchus and the larynx in the human body, for example. The aerial long distance is used in diagnosing the upper respiratory tract of the lungs or the respiratory organs in the human body.

(2) Aerial Short Distance (f, FNO, ndR)=(0.306, 4.50, 1.5168), BF=0.0375

In the endoscope, an aerial short distance corresponds to observation of the segmental bronchi and the bronchioles in the human body, for example. The aerial short distance is used in diagnosing the lower respiratory tract of the lungs or the respiratory organs in the human body.

(3) Underwater Long Distance (f, FNO, ndR)=(0.306, 4.02, 1.5168), BF=0.0125

In the endoscope, an underwater long distance corresponds to observation of the inside of the uterine or the stomach in the human body, for example.

(4) Underwater Short Distance (f, FNO, ndR)=(0.306, 4.47, 1.5168), BF=0.0375

In the endoscope, an underwater short distance corresponds to observation of the bladder, the inside of the coronary artery, the knee joint, or the hip joint in the human body, for example. The underwater short distance is used in diagnosing the inside of the blood vessel in the human body.

As described above, according to the endoscope 111 of the nineteenth configuration example, it is possible to realize the small-diameter lens 93 in which the maximum exterior diameter Dmax of the distal portion 15 can be set to 1.0 mm or smaller. In the small-diameter lens 93, it is possible to obtain desired optical performance.

Twentieth Configuration Example

Figure 22A:
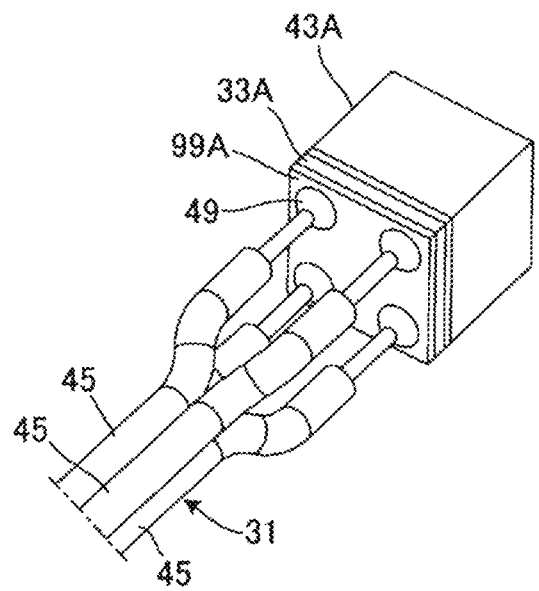
FIG. 22A is a view illustrating a first example of an image sensor in the endoscope according to the second embodiment.
Figure 22B:
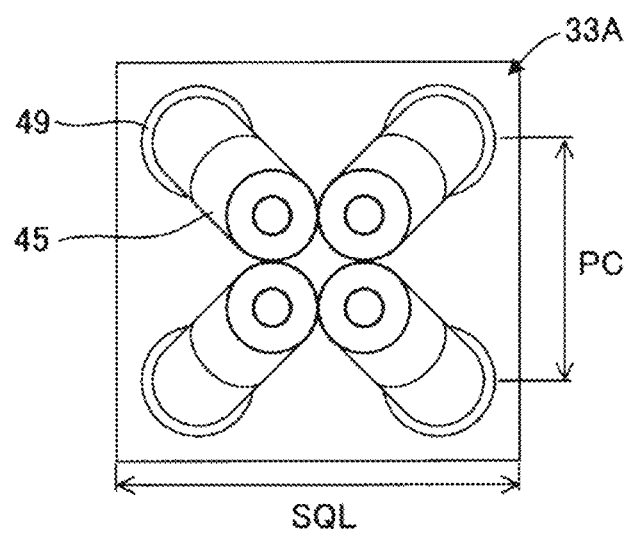
FIG. 22B is a view illustrating the first example of the image sensor in the endoscope according to the second embodiment.

A twentieth configuration example shows a specific configuration example of an image sensor 33A in the endoscope 111. FIGS. 22A and 22B are views illustrating a first example of the image sensor.

The image sensor 33A in the first example is formed so that a shape of a cross section taken along a plane perpendicular to the optical axis of the lens 93 is a quadrangular shape. In this case, the exterior shape of the imaging area on a sensor cover glass 43A side and a terminal surface on the transmission cable 31 side is the quadrangular shape. The exterior shape of the image sensor 33A and the sensor cover glass 43A is formed in a quadrangular prismatic shape. The exterior shape of the image sensor 33A and the sensor cover glass 43A, and the lens 93 (not illustrated) is formed in the same quadrangular prismatic shape.

An electric circuit 99A using a circuit pattern is disposed on a substrate (terminal surface) disposed on the rear end side of the image sensor 33A, and the conductor connection parts (connection lands) 49 are respectively disposed at four corners. The transmission cable 31 having the four electric cables 45 is connected thereto by means of soldering. That is, the four electric cables 45 are connected at four corners on the terminal surface of the image sensor 33A. The four electric cables 45 are located and connected at the four corners on the terminal surface of the image sensor 33A in a state where end portions are respectively formed in a crank shape. Here, a width (length of one side of the square cross section) SQL of the exterior shape of the image sensor 33A is 0.5 mm or smaller, for example. A pitch PC between the adjacent electric cables of the four electric cables 45 is 0.3 mm or greater, for example.

Figure 23A:
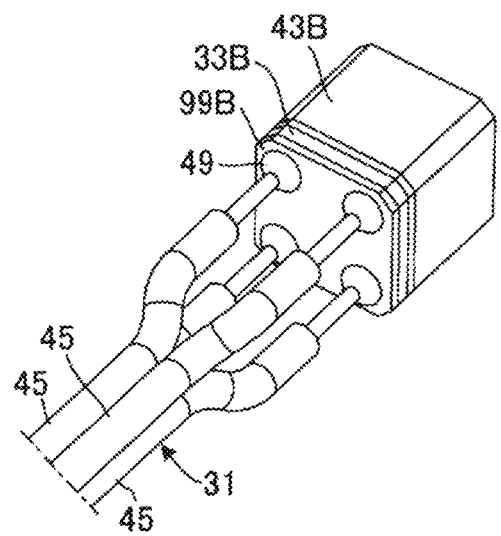
FIG. 23A is a view illustrating a second example of an image sensor in the endoscope according to the second embodiment.
Figure 23B:
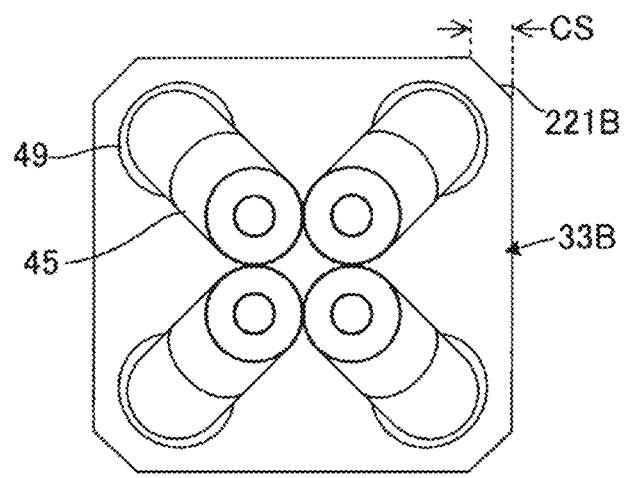
FIG. 23B is a view illustrating the second example of the image sensor in the endoscope according to the second embodiment.

FIGS. 23A and 23B are views illustrating a second example of the image sensor. An image sensor 33B in the second example is formed so that a shape of the cross section taken along the plane perpendicular to the optical axis of the lens 93 is an octagonal shape. An exterior shape of the image sensor 33B and a sensor cover glass 43B is formed in an octagonal prismatic shape. The exterior shape of the image sensor 33B, the sensor cover glass 43B, an electric circuit 99B, and the lens 93 (not illustrated) is formed in the same octagonal prismatic shape. Here, configurations which are different from those in the first example will be mainly described. With regard to configurations which are the same as those in the first example, description will be omitted.

The second example employs the octagonal shape in which four corner portions (four corners) of the square in a cross-sectional shape of the image sensor 33B are respectively cut out (chamfered) by one cutout plane 221B. In the dimension of the cutout portion of the exterior shape of the image sensor 33B, a dimension CS to an end surface of the cutout plane 221B with respect to apexes of the square is 20 to 50 µm, for example. In this way, the four corner portions of the exterior shape of the image sensor 33B are cut out by the cutout plane 221B. Accordingly, the pitch PC between the electric cables of the four electric cables 45 is separated as far as possible. The exterior shape dimension in the diagonal direction of the image sensor 33B can be reduced. This can further contribute to the small-diameter endoscope. For example, the dimension CS of the cutout portion is set to 21.2 µm, the exterior shape dimension in the diagonal direction of the image sensor 33B is reduced at one location as much as 15 µm, and the diameter is reduced in both ends in the diagonal direction as much as 30 µm. If the configuration of the cutout plane 221B is applied to the image sensor in which the exterior shape dimension SQL of one side is 0.5 mm and the exterior shape dimension in the diagonal direction is 0.705 mm in a state where the exterior shape is a square shape, the exterior shape dimension in the diagonal direction is reduced as much as 0.675 mm by chamfering. Accordingly, it is possible to realize the small-diameter endoscope of ϕ0.7 mm or smaller.

Figure 24A:
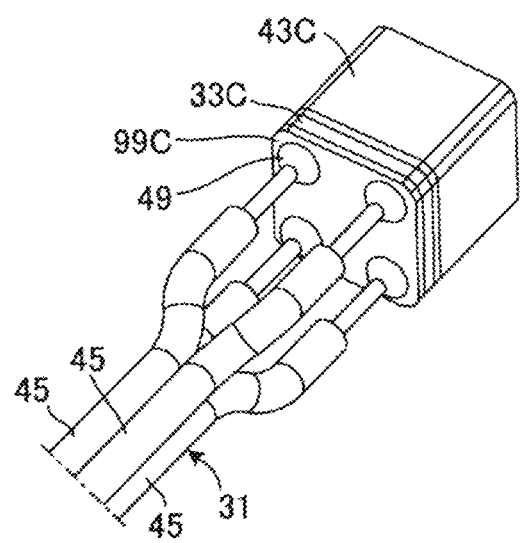
FIG. 24A is a view illustrating a third example of an image sensor in the endoscope according to the second embodiment.
Figure 24B:
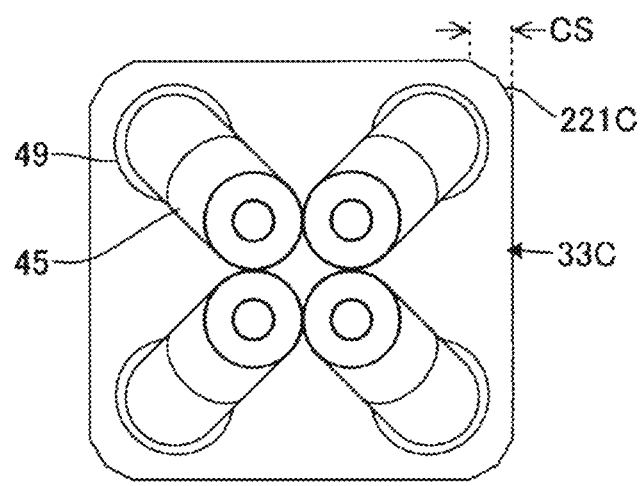
FIG. 24B is a view illustrating the third example of the image sensor in the endoscope according to the second embodiment.

FIGS. 24A and 24B are views illustrating a third example of the image sensor. An image sensor 33C in the third example is formed so that a shape of the cross section taken along the plane perpendicular to the optical axis of the lens 93 is a dodecagonal shape. An exterior shape of the image sensor 33C and a sensor cover glass 43C is formed in a dodecagonal prismatic shape. The exterior shape of the image sensor 33C, the sensor cover glass 43C, an electric circuit 99C, and the lens 93 (not illustrated) is formed in the same octagonal prismatic shape. Here, configurations which are different from those in the first example will be mainly described. With regard to configurations which are the same as those in the first example, description will be omitted. The third example employs the dodecagonal shape in which four corner portions of the square in a cross-sectional shape of the image sensor 33C are respectively cut out by two cutout planes 221C. In the dimension of the cutout portion of the exterior shape of the image sensor 33C, the four corner portions are cut out by two planes. Accordingly, the dimension CS to an end surface of the cutout plane with respect to apexes of the square can be further increased, compared to that in the second example. Therefore, it is possible to further reduce the diameter of the image sensor.

Without being limited to the square, octagonal, and dodecagonal shapes, the shape of the cross section perpendicular to the lens optical axis of the image sensor 33, a 4×n-polygonal shape (n is a natural number) such as a 16-polygonal shape may be employed. In this way, the cross-sectional shape of the image sensor 33 is configured to be the 4×n-polygonal shape. Accordingly, the transmission cable 31 using the four electric cables 45 can be connected, and the diameter of the image sensor and the endoscope can be further reduced. The image sensor 33 has a shape in which the four corners of the cross-sectional shape of the 4×n-polygonal shape of the image sensor 33 are chamfered. In this manner, the dimension in the diagonal direction of the image sensor 33 can be further reduced, and this can further contribute to the small-diameter image sensor 33.

As described above, according to the endoscope 111 of the twentieth configuration example, it is possible to realize the small-diameter image sensor 33 in which the maximum exterior diameter Dmax of the distal portion 15 can be set to 1.0 mm or smaller.

The endoscope 111 according to the present embodiment includes the image sensor 33 that is disposed in the distal portion 15 of the insertion part 21, and whose imaging area 41 is covered with the sensor cover glass 43, the lens 93 that causes the incident light reflected from an imaging subject to form an image on the imaging area 41, and the bonding resin 37 that fixes the lens 93 and the sensor cover glass 43. The lens 93 is configured to include the single lens whose the exterior shape is formed in a prismatic shape, and in which the first surface on the imaging subject side is the plane and the second surface on the imaging side has the convex surface. On the imaging side of the lens 93, the central part has the optical element part 201 holding the convex curved surface portion 97 which protrudes in a substantially spherical shape configuring the lens surface of the convex surface. The peripheral edge part has the integrally formed edge portion 202 which has the bonding plane 203 whose end surface is the plane. In this manner, it is possible to realize the small-diameter lens 93 in which the maximum exterior diameter Dmax of the distal portion 15 can be set to 1.0 mm or smaller.

In the endoscope 111 according to the present embodiment, the bonding plane 203 of the lens 93A is formed so that the exterior peripheral portion has the square shape and the inner peripheral portion has substantially the square shape whose corners are rounded.

In the endoscope 111 according to the present embodiment, the bonding plane 203 of the lens 93B has the circular shape which is concentric with the convex curved surface portion 97 whose exterior peripheral portion has the square shape and whose inner peripheral portion has the circular dome shape.

In the endoscope 111 according to the present embodiment, the optical element part 201 of the lens 93C has the barrel shape in which four circumferential portions corresponding to four sides of the square exterior shape of the lens are partially notched in the exterior peripheral portion of the convex curved surface portion 97 having the circular dome shape. In this manner, the inclined plane 204 between the optical element part 201 and the edge portion 202 can be gently formed. Accordingly, it is possible to improve the removability when the lens is manufactured. In a case where the inclined plane 204 is equally inclined, the bonding width Wa of the bonding plane 203 of the edge portion 202 can be further increased, and thus, the bonding strength can be improved.

In the endoscope 111 according to the present embodiment, from the exterior peripheral portion of the convex curved surface portion 97 to the inner peripheral portion of the bonding plane 203, the lens 93 has the inclined plane 204 extending from the lens center to the exterior periphery. The angle of the inclined plane 204 is $60°\leq\theta A\leq 90°$, and the bonding width Wa of the bonding plane 203 is 50 µm or greater, if the angle of the opening is set to $\theta A$ when viewed from the lens center. In this manner, in the lens 93 allowed to have the small diameter, the lens 93 and the sensor cover glass 43 can be reliably bonded and fixed to each other. In addition, the angle of the inclined plane 204 is sufficiently secured. Accordingly, it is possible to improve the removability when the lens is manufactured.

In the endoscope 111 according to the present embodiment, the bonding plane 203 of the lens 93 has the tapered inclined portion 207 which is inclined in the direction from the inner peripheral portion to the exterior peripheral portion of the edge portion 202. In this manner, the bonding resin 37 coating on the bonding plane 203 is likely to move to the exterior peripheral side, and is less likely to enter the inside of the edge portion 202. Accordingly, it is possible to prevent the bonding resin 37 from interfering with the air layer 95 formed in the optical element part 201.

The endoscope 111 according to the present embodiment includes the objective cover glass 91 that covers the image sensor 33, the sensor cover glass 43, the bonding resin 37, the lens 93, and the surface on the imaging subject side of the lens 93. The objective cover glass 91 is configured to include an optical material in which the thickness TGt is $0.1 \text{ mm} \leq TGt \leq 0.5 \text{ mm}$, the refractive index ndF is $1.3 \leq ndF$, and the Abbe vdF is $30 \leq vdF$. The sensor cover glass 43 is configured to include an optical material in which the thickness SGt is $0.1 \text{ mm} \leq SGt \leq 0.5 \text{ mm}$, the refractive index ndR is $1.3 \leq ndR \leq 2.0$, $ndF \leq ndR$, the Abbe vdR is $40 \leq vdR$, and $vdF \leq vdR$. In the lens 93 using the single lens, the focal length f is $0.1 \text{ mm} \leq f \leq 1.0 \text{ mm}$, and the F-number FNO is $1.4 \leq FNO \leq 8.0$. In this manner, it is possible to realize the small-diameter lens 93 in which the maximum exterior diameter Dmax of the distal portion 15 can be set to 1.0 mm or smaller.

In the endoscope 111 according to the present embodiment, when the distance from the image forming point on the imaging side to the end surface on the imaging subject side of the sensor cover glass 43 in the focal length of the lens 93 is set to x ($0 \leq x \leq f$), the maximum angle of the light beam emitted to the image forming point from the lens 93 in a state of air only with respect to the optical axis is set to θair, and the maximum angle of the light beam emitted to the image forming point through the sensor cover glass 43 from the lens 93 in a state including the sensor cover glass 43 with respect to the optical axis is set to θgl, the lens 93 and the sensor cover glass 43 have the combination of the focal length f, the F-number FNO, and the refractive index ndR, which satisfies $0.1 \leq x \cdot (\tan \theta air)/(\tan \theta gl) \leq 0.5$. In this manner, in the small-diameter lens 93, it is possible to obtain desired optical performance.

The endoscope 111 according to the present embodiment includes the image sensor 33, the sensor cover glass 43, the bonding resin 37, the lens 93, and the transmission cable 31 having the four electric cables 45 which are respectively connected to the four conductor connection parts 49 disposed on the surface opposite to the imaging area 41 of the image sensor 33. In the image sensor 33, the shape of the cross section perpendicular to the optical axis of the lens 93 is the 4×n-polygonal shape (n is a natural number). The four electric cables 45 are respectively connected to the four conductor connection parts 49 arranged at four corners on the rear end surface of the 4×n-polygonal shape of the image sensor 33. In this manner, it is possible to realize the small-diameter image sensor 33 in which the maximum exterior diameter Dmax of the distal portion 15 can be set to 1.0 mm or smaller.

The endoscope 111 according to the present embodiment has the shape in which four corners on the rear end surface of the 4×n-polygonal shape of the image sensor 33 are chamfered. In this manner, the dimension in the diagonal direction of the image sensor 33 can be further reduced, and this can further contribute to the small-diameter image sensor 33.

In the endoscope 111 according to the present embodiment, the exterior shape of the image sensor 33, the sensor cover glass 43, and the lens 93 is formed in the same prismatic shape of the 4×n-polygonal shape. In this manner, the exterior diameter from the lens 93 to the image sensor 33 through the sensor cover glass 43 can be further reduced.

In the endoscope 111 according to the present embodiment, the image sensor 33 is configured so that the length of one side of the 4×n-polygonal shape of the cross section perpendicular to the optical axis is 0.5 mm or smaller. In this manner, the exterior shape dimension in the diagonal direction of the image sensor 33 can be reduced to approximately 0.7 mm.

In the endoscope 111 according to the present embodiment, the maximum exterior diameter of the distal portion 15 can be formed within a range from the limited diameter to 1.0 mm which corresponds to the diameter of the circumscribed circle of the substrate of the image sensor 33. In this manner, the maximum exterior diameter Dmax is set to be smaller than 1.0 mm. Accordingly, the endoscope 111 can be more easily inserted into the blood vessel of the human body, for example.

Twenty First Configuration Example

Figure 25:
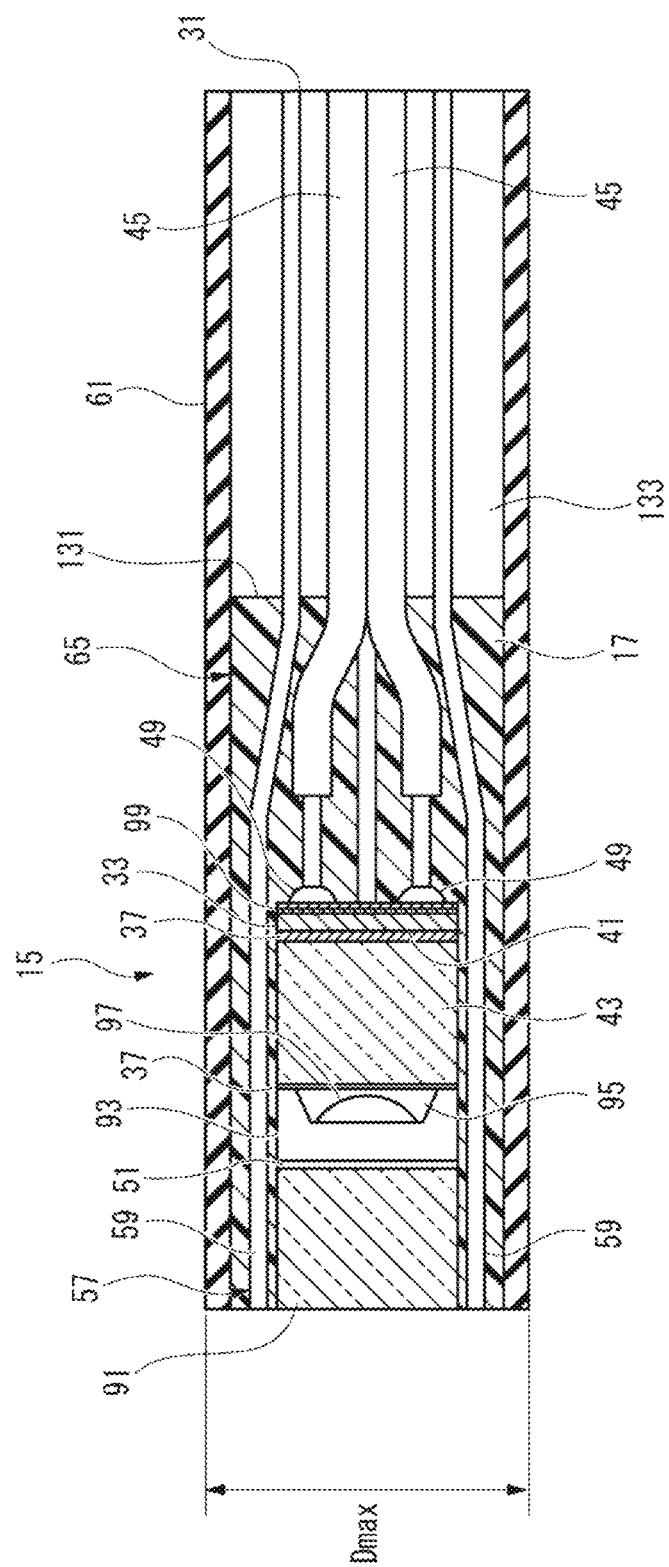
FIG. 25 is a side sectional view in which a sheath in the endoscope according to the present embodiment extends to a distal end.

FIG. 25 is a side sectional view in which the sheath 61 in the endoscope 11 according to the present embodiment extends to the distal end. In the endoscope 11 according to a twenty first configuration example, the molded part 65 is formed to have a smaller diameter than the shape in FIG. 13. The molded part 65 illustrated in FIG. 25 does not have the small-diameter extension portion 71, and is formed in a cylindrical shape. The sheath 61 is coated in the exterior periphery of the molded part 65. That is, according to the twenty first configuration example, the molded part 65 is thinned compared to that illustrated in FIG. 13, and the thin sheath 61 having the same thickness is extended to the distal end. The sheath 61 has a cavity 133 on the plug part 23 side rather than a mold rear end surface 131. The optical fiber 59 and the electric cable 45 pass through the cavity 133. The lens 93 and the image sensor 33 are coaxially arranged. The coaxial arrangement means a relative position relationship between the lens 93 and the image sensor 33, in which the optical axis of the lens 93 passes through the center of the imaging area 41. The structure according to the above-described twenty first configuration example is common to that according to the twenty second configuration example, the twenty third configuration example, and the twenty fourth configuration example in the following.

In the endoscope 11 according to the twenty first configuration example, the exterior shape in the direction perpendicular to the axial direction passing through the optical axis or the lens center is formed in a right-angled quadrangular shape having four corners. The right-angled quadrangular shape having four corners includes a square shape and a rectangular shape, for example. The square shape in the exterior shape in the direction perpendicular to the axial direction passing through the optical axis of the lens 93 or the lens center includes a square shape having the same size as the image sensor 33, and a square shape similar to the shape of the image sensor 33. That is, in a case where the lens 93 has the square shape in the exterior shape in the direction perpendicular to the axial direction passing through the optical axis of the lens 93 or the lens center, the lens 93 can employ the square shape which is smaller in size than that of the image sensor 33.

In the image sensor 33, the exterior shape in the direction perpendicular to the axial direction passing through the optical axis of the lens 93 or the lens center is the square shape. In the image sensor 33, the length of a side is longer than or the same as the length of the longest side of the lens 93. Accordingly, in a case where the lens 93 has the square shape, in the image sensor 33, the long side and four sides of the rectangular shape have the equal length. The "longest side' of the lens 93 means one side of the square shape, in a case where the lens 93 has the square shape.

According to the endoscope 11 in the twenty first configuration example, similarly to the above-described configuration examples, it is possible to achieve miniaturization (for example, reduced exterior diameter in the insertion part on the distal side) and cost reduction. In addition, it is possible to eliminate a connection portion for connecting the sheath 61 and the molded part 65 to each other by using end surfaces thereof. As a result, it is possible to obtain the very smooth insertion part 21 having no connection portion on the exterior peripheral surface. The connection portion of the end surfaces between the sheath 61 and the molded part 65 is not present in the extending direction of the insertion part 21. Therefore, there is no possibility that the connection portion may be detached, and it is possible to improve the reliability of the endoscope 11.

Twenty Second Configuration Example

Figure 26:
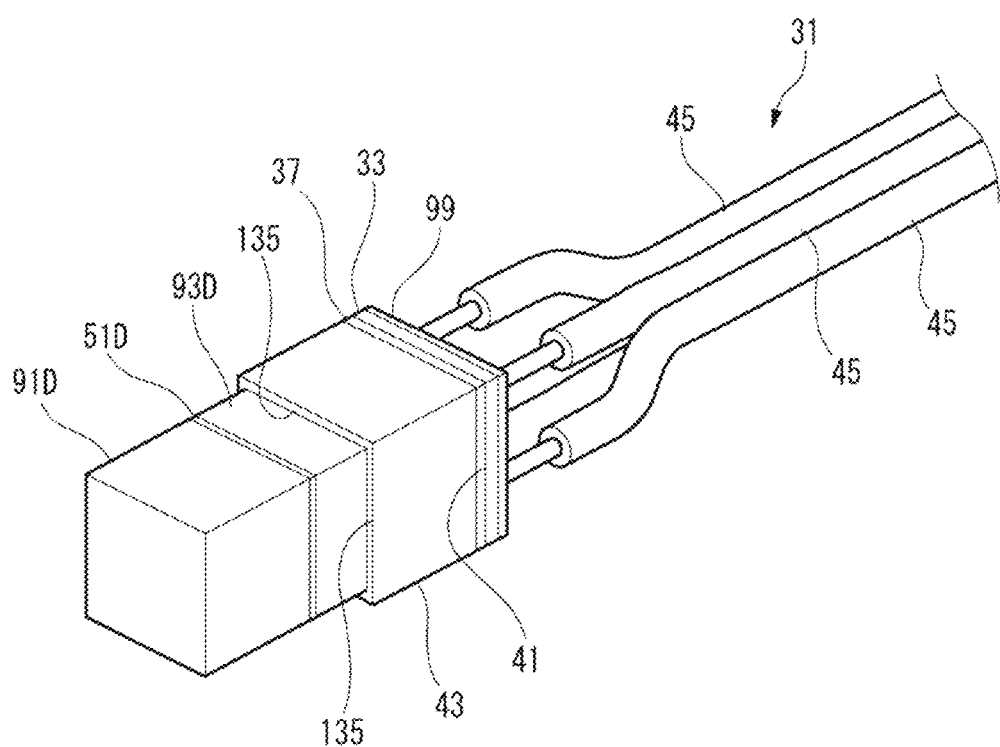
FIG. 26 is a perspective view illustrating an example in which the lens has a rectangular shape and the imaging area has a square shape in the endoscope according to the present embodiment.
Figure 27:
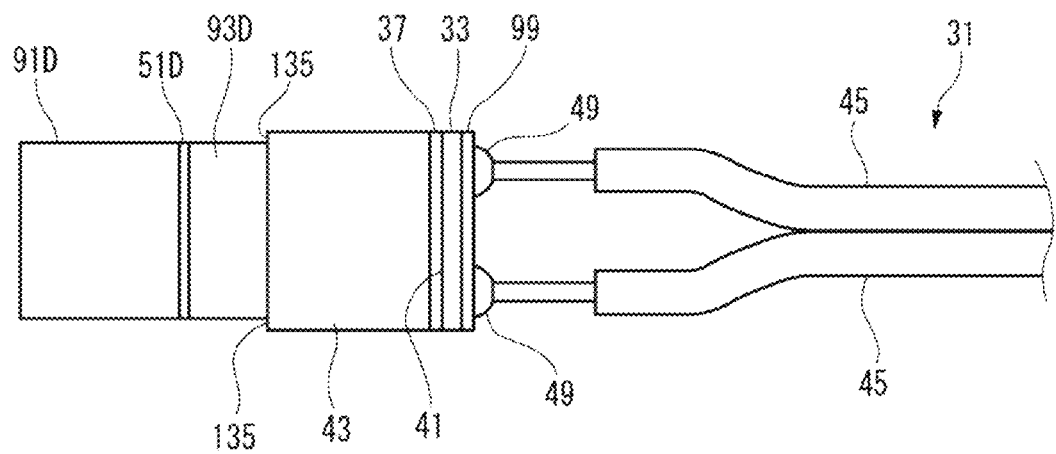
FIG. 27 is a side view of FIG. 26.

FIG. 26 is a perspective view illustrating an example in which a lens 93D has a rectangular shape and the image sensor 33 has a square shape in the endoscope 11 according to the present embodiment. FIG. 27 is a side view of FIG. 26. In the endoscope 11 according to a twenty second configuration example, the exterior shape in the direction perpendicular to the axial direction passing through the optical axis of the lens 93D or the lens center is smaller than and similar to the exterior shape in the direction perpendicular to the axial direction passing through the optical axis of the image sensor 33 or the lens center. In other words, the exterior shape in the direction perpendicular to the axial direction passing through the optical axis of the lens 93D or the lens center is the square shape. The length of one side of the exterior shape of the lens 93 is smaller than the length of one side of the exterior shape of the image sensor 33. According to the twenty second configuration example, on the surface of the image sensor 33 to which the lens 93D is bonded, a frame-shaped surface 135 surrounding the lens 93D is exposed by protruding from the lens 93D. That is, a step portion is formed between the lens 93D and the image sensor 33. The frame-shaped surface 135 is covered with the molded part 65. An objective cover glass 91D and an iris 51D are formed to have an exterior shape and a size which are the same as those of the lens 93D.

According to the endoscope 11 in the twenty second configuration example, similarly to the above-described configuration examples, it is possible to achieve miniaturization (for example, reduced exterior diameter in the insertion part on the distal side) and cost reduction. In addition, the frame-shaped surface 135 of the image sensor 33 is covered with the molded part 65. Accordingly, the step portion between the lens 93D and the image sensor 33 is embedded in the molded part 65. Compared to a case where the length of one side of the exterior shape of the lens 93 and the length of one side of the exterior shape of the image sensor 33 are the same as each other, the coating amount of the molded part 65 increases. In this regard, it is possible to further increase fixing strength in the molded part 65, the lens 93D, and the image sensor 33.

Twenty Third Configuration Example

Figure 28:
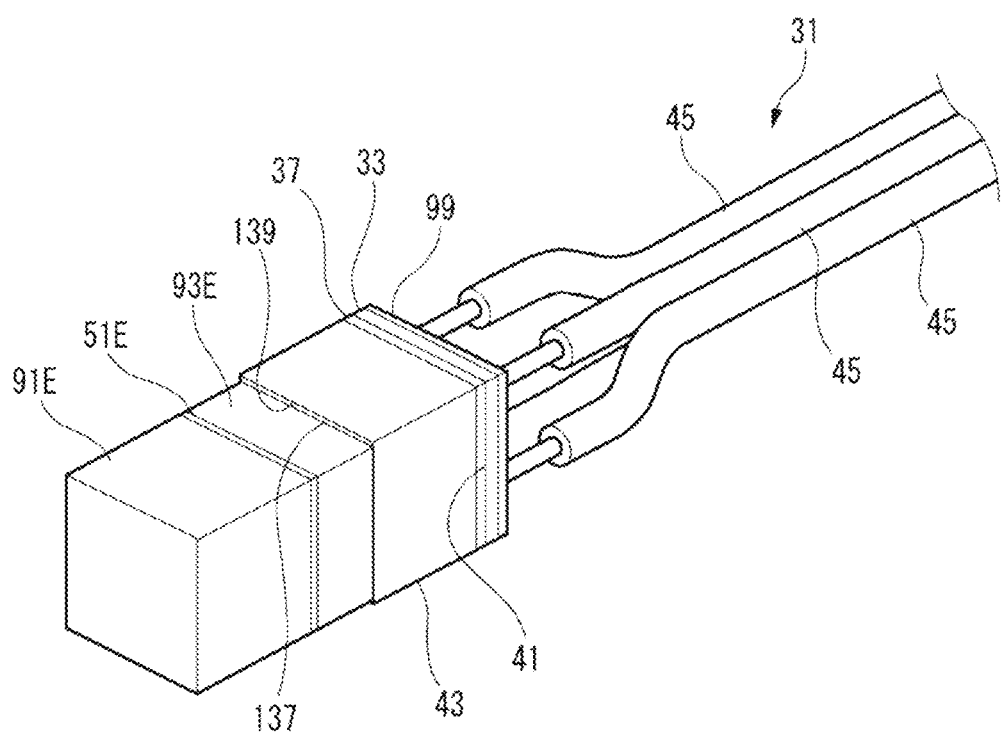
FIG. 28 is a perspective view illustrating an example in which the lens has a rectangular shape and the image sensor has a square shape in the endoscope according to the present embodiment.
Figure 29:
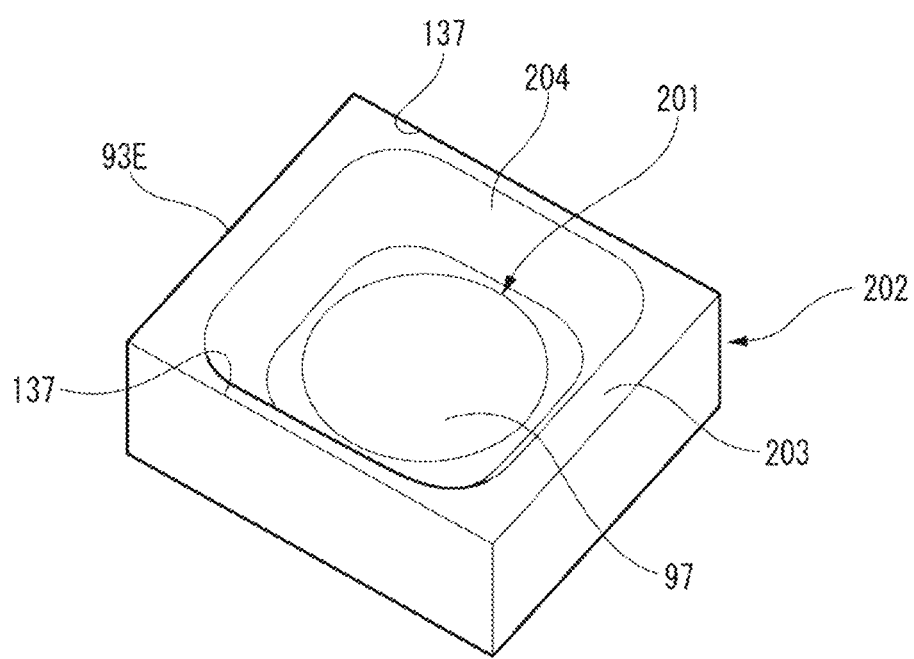
FIG. 29 is a perspective view of the rectangular lens illustrated in FIG. 28, in the endoscope according to the present embodiment.
Figure 30:
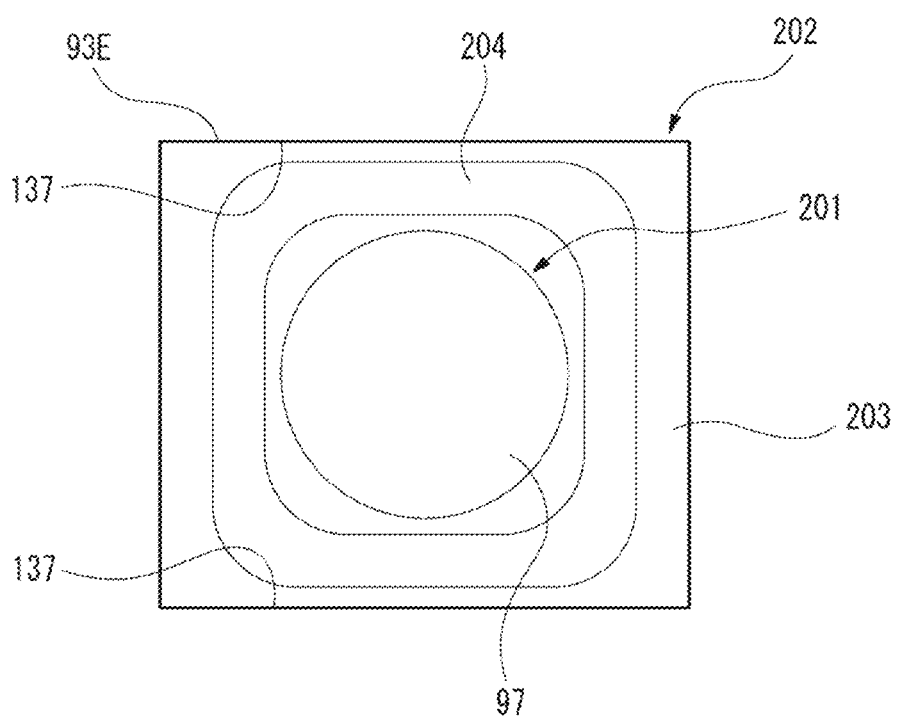
FIG. 30 is a front view of the rectangular lens illustrated in FIG. 28, in the endoscope according to the present embodiment.

FIG. 28 is a perspective view illustrating an example in which a lens 93E has a rectangular shape and the image sensor 33 has a square shape in the endoscope 11 according to the present embodiment. FIG. 29 is a perspective view of the rectangular lens 93E illustrated in FIG. 28, in the endoscope 11 according to the present embodiment. FIG. 30 is a front view of the rectangular lens 93E illustrated in FIG. 28, in the endoscope 11 according to the present embodiment.

In the endoscope 11 according to the twenty third configuration example, the exterior shape in the direction perpendicular to the axial direction passing through the optical axis of the lens 93E or the lens center is rectangular. In the rectangular lens 93E, a long side 137 is the same as one side of the image sensor 33. In the rectangular lens 93E, the axis passing through the optical axis or the lens center passes through an intersection of a pair of diagonal lines. In the rectangular lens 93E, the axis passing through the optical axis or the lens center is coincident with the center of the imaging area 41. According to the twenty third configuration example, on the surface of the image sensor 33 to which the lens 93E is bonded, a pair of long frame surfaces 139 interposing the lens 93E therebetween are exposed by protruding from the lens 93E. That is, a step portion is formed between the lens 93E and the image sensor 33. The long frame surface 139 is covered with the molded part 65. An objective cover glass 91E and an iris 51E are formed to have the same exterior shape as the lens 93E.

According to the endoscope 11 in the twenty third configuration example, similarly to the above-described configuration examples, it is possible to achieve miniaturization (for example, reduced exterior diameter in the insertion part on the distal side) and cost reduction. In addition, the long frame surface 139 of the image sensor 33 is covered with the molded part 65. Accordingly, the step portion between the lens 93E and the image sensor 33 is embedded in the molded part 65. Compared to a case where the length of one side of the exterior shape of the lens 93 and the length of one side of the exterior shape of the image sensor 33 are the same as each other, the coating amount of the molded part 65 increases. In this regard, it is possible to further increase fixing strength in the molded part 65, the lens 93E, and the image sensor 33.

The fixing strength of the molded part 65 in the endoscope 11 according to the twenty third configuration example will be described in detail. Particularly in a case where the endoscope 11 has a small diameter so that the maximum exterior diameter Dmax is smaller than 1.0 mm, whereas the image sensor 33 employs the square shape, the lens 93E employs the rectangular shape. In this manner, the greater advantageous effect can be obtained. That is, since the sheath 61 is allowed to have the small diameter, in the distal portion 15, the inner peripheral surface of the sheath 61 is as close as possible to the corner portions (external corners) of the image sensor 33. If this structure is employed, in a case where the exterior shape of the lens 93 is the same square shape as image sensor 33, the inner peripheral surface of the sheath 61 is similarly close to the corner portion of the lens 93. As a result, the lens 93 is less likely to secure bonding strength between the corner portion and the sheath 61. In contrast, according to the twenty third configuration example, whereas the image sensor 33 employs the square shape, the lens 93E employs the rectangular shape in which the long side has the same length as the side of the image sensor 33. In this manner, the corner portion of the lens 93E can be separated from the inner peripheral surface of the sheath 61. That is, a sheath adhesion space can be secured between the inner peripheral surface of the sheath 61 and the corner portion of the lens 93E. As a result, even if the endoscope 11 has a particularly small diameter, it is possible to secure the fixing strength between the sheath 61 and the lens 93E.

Twenty Fourth Configuration Example

Figure 31:
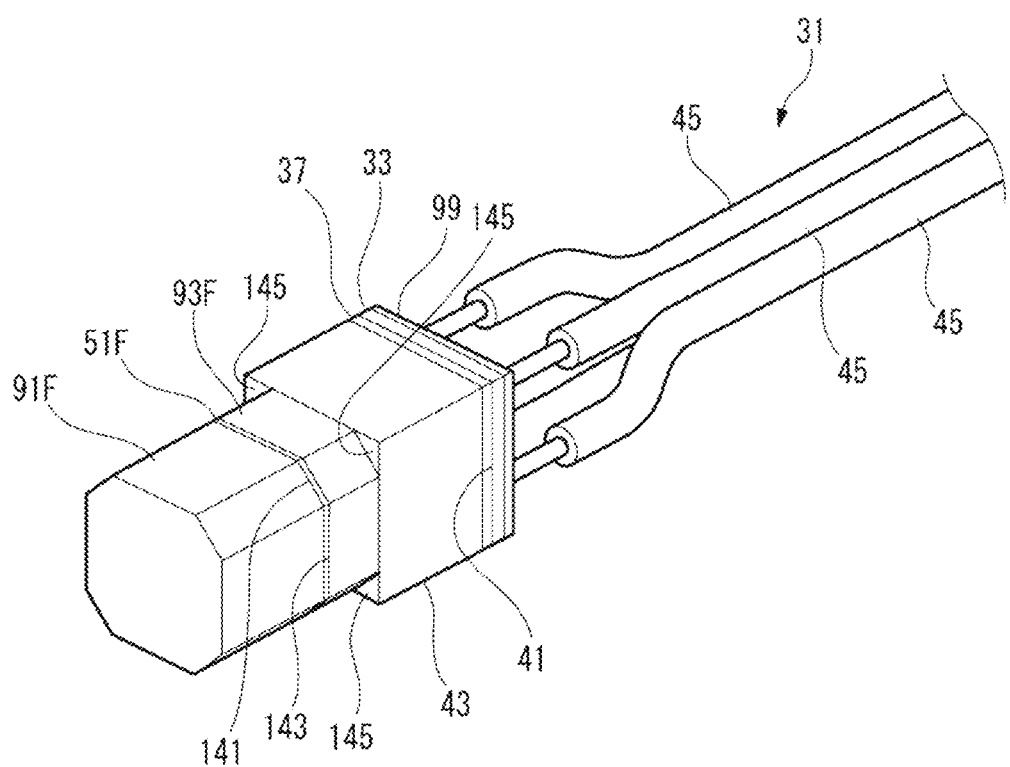
FIG. 31 is a perspective view illustrating an example in which the lens has an octagonal shape and the image sensor has a square shape in the endoscope according to the present embodiment.
Figure 32:
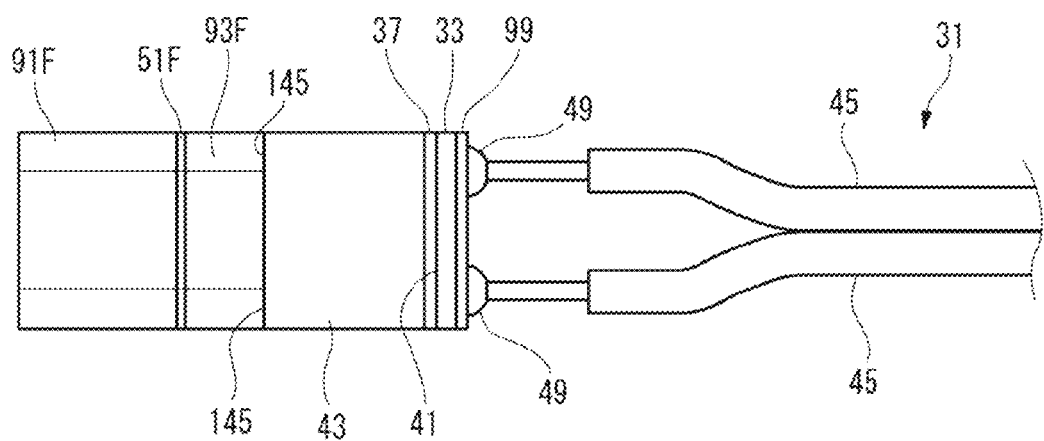
FIG. 32 is a side view of FIG. 31.
Figure 33:
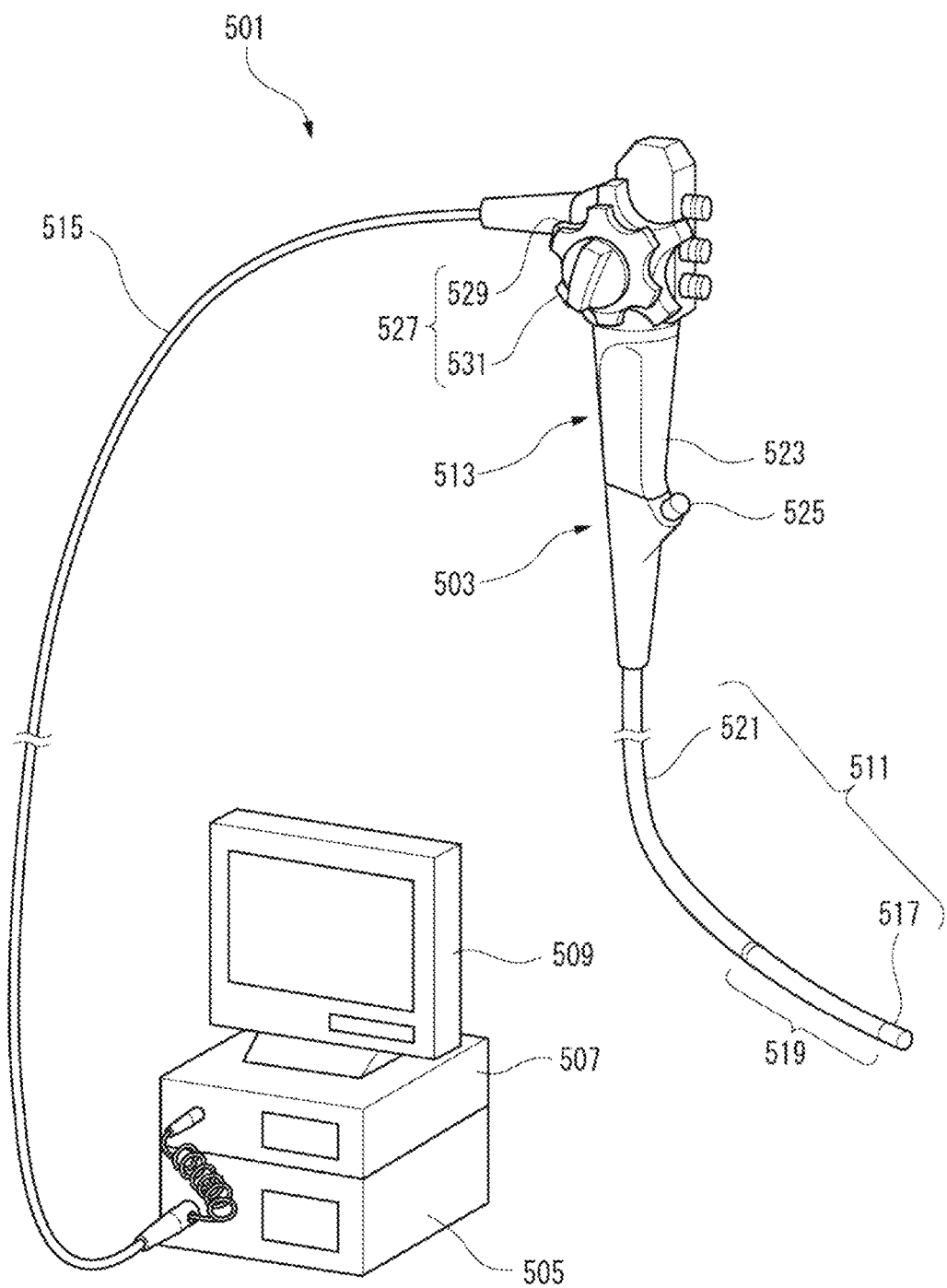
FIG. 33 is an overall configuration diagram of an electronic endoscopic system including an endoscope according to an example in the related art.
Figure 34:
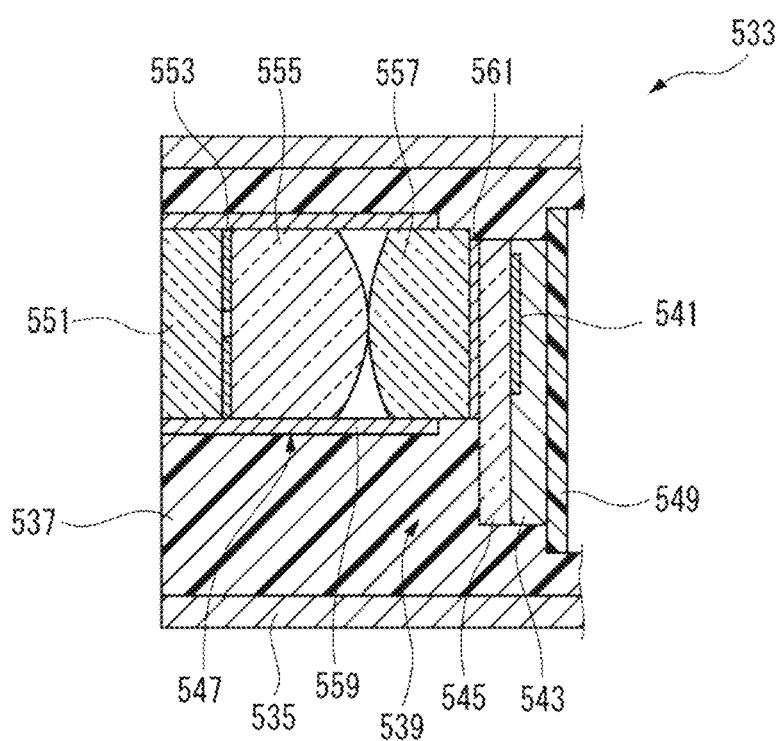
FIG. 34 is a partial sectional view illustrating an example of an end structure of the endoscope in the related art.

FIG. 31 is a perspective view illustrating an example in which a lens 93F has an octagonal shape and the image sensor 33 has a square shape in the endoscope according to the present embodiment. FIG. 32 is a side view of FIG. 31. In the endoscope 11 according to a twenty fourth configuration example, the exterior shape of the lens 93F is the octagonal shape. In other words, the lens 93F has an octagonal prismatic shape. In the octagonal shape, four short sides 141 having the same length and four long sides 143 having the same length are alternately arrayed side by side and connected to each other, and the opposing short sides 141 and the opposing long sides 143 are parallel to each other. In other words, the octagonal shape obtained by chamfering four corners of the quadrangular shape at an angle of 45 degrees. In the lens 93F, the chamfered portion is the short side 141. In this case, FIG. 31 illustrates an example when the quadrangular shape is the square shape. The length of one side of the image sensor 33 is the same as the distance between a pair of opposing long sides of the lens 93F.

According to the twenty fourth configuration example, on the surface of the image sensor 33 to which the lens 93F is bonded, four internal corner surfaces 145 are exposed by protruding from the short sides 141 of the lens 93F. That is, four step portions are formed between the lens 93F and the image sensor 33. The internal corner surfaces 145 are covered with the molded part 65. An objective cover glass 91F and an iris 51F are formed to have the same exterior shape as the lens 93F.

According to the endoscope 11 in the twenty fourth configuration example, similarly to the above-described configuration examples, it is possible to achieve miniaturization (for example, reduced exterior diameter in the insertion part on the distal side) and cost reduction. In addition, the internal corner surfaces 145 of the image sensor 33 are covered with the molded part 65. Accordingly, the step portions between the lens 93F and the image sensor 33 are embedded in the molded part 65. Compared to a case where the length of one side of the exterior shape of the lens 93 and the length of one side of the exterior shape of the image sensor 33 are the same as each other, the coating amount of the molded part 65 increases. In this regard, it is possible to further increase fixing strength in the molded part 65, the lens 93F, and the image sensor 33. The lens 93F employs the octagonal shape. In this manner, it is possible to secure the convex curved surface portion 97 having the same area as that in a case of substantially square shape. It is not necessary to degrade the optical characteristics in order to secure the fixing strength. That is, while the octagonal lens 93F secures the optical characteristics similarly to a case of the square shape, it is possible to increase the fixing strength.

According to the endoscope 11 in the twenty fourth configuration example, the exterior shape in the direction perpendicular to the axial direction passing through the optical axis of the lens 93F or the lens center has a structure in which the short side with respect to the long side of the octagonal shape is chamfered. In this manner, compared to the endoscope 11 according to the third configuration example (for example, refer to FIG. 15), it is possible to further miniaturize the distal side (for example, a side inserted into the body) of the endoscope 11.

Hitherto, although various embodiments have been described with reference to the drawings, the present invention is not limited to the examples, as a matter of course. It is apparent for those skilled in the art that various modification examples or correction examples are conceivable within the scope disclosed in claims. It is understood that the modification examples and the correction examples are naturally included in the technical scope of the present invention. Within the scope not departing from the gist of the invention, respective configuration elements in the above-described embodiments may be optionally combined with each other.

According to the present invention, there is provided an endoscope having a single lens that has a square exterior shape in the direction perpendicular to an optical axis, an image sensor that has an square exterior shape which is same as the exterior shape of the single lens, in the direction perpendicular to the optical axis, a sensor cover that covers an imaging area of the image sensor, and has an exterior shape which is same as the exterior shape of the single lens, in the direction perpendicular to the optical axis, and a bonding resin portion that fixes the sensor cover to the single lens, the optical axis of the single lens coinciding with a center of the imaging area. The image sensor has one side whose length is 0.5 mm or smaller. The single lens is a lens which is formed in the prismatic shape, and whose first surface on an imaging subject side has a plane and whose second surface on an imaging side has the convex surface. The central portion of the single lens has the convex curved surface which protrudes in substantially spherical shape configuring a lens surface of the convex surface on the imaging side. The peripheral edge portion of the single lens has a planar end surface, and has a bonding plane with the sensor cover over the entire area of the planar end surface.

According to another aspect of the present invention, there is provided the endoscope in which the bonding plane is formed so that the exterior peripheral portion has the square shape and the inner peripheral portion has substantially the square shape whose corners are rounded.

According to another aspect of the present invention, there is provided the endoscope in which the bonding plane has an exterior peripheral portion which has a square shape and an inner peripheral portion which has a circular shape concentric with the convex curved surface having a circular dome shape.

According to another aspect of the present invention, there is provided the endoscope in which an exterior peripheral portion of the convex curved surface having a circular dome shape has the barrel shape in which the four circumferential portions corresponding to four sides of the square exterior shape of the single lens are partially notched.

According to another aspect of the present invention, there is provided the endoscope in which from the exterior peripheral portion of the convex curved surface to the inner peripheral portion of the bonding plane, the single lens has the inclined plane extending from a center of the single lens toward an exterior periphery of the single lens. An angle of the inclined plane is $60°≤θA≤90°$, in case that the angle of the inclined plane is defined as an angle of an opening being set to θA when viewed from the lens center of the single lens.

According to another aspect of the present invention, there is provided the endoscope in which the bonding plane has an inclined portion which is tapered so as to be inclined in the direction from the inner peripheral portion to the exterior peripheral portion of the peripheral edge portion.

According to another aspect of the present invention, there is provided the endoscope in which the bonding plane has the bonding width of 50 μm or greater.

According to another aspect of the present invention, there is provided the endoscope having an image sensor that is disposed in the distal portion of an insertion portion, and whose imaging area is covered with a sensor cover, a single lens that has a square exterior shape in a direction perpendicular to the optical axis, and a bonding resin portion that fixes the single lens and the sensor cover glass. The single lens is a lens which is formed in the prismatic shape, and whose first surface on the imaging subject side has the plane and whose second surface on an imaging side has the convex surface. The central portion of the single lens has the convex curved surface which protrudes in substantially spherical shape configuring the lens surface of the convex surface on the imaging side. The peripheral edge portion of the single lens has a planar end surface, and has a bonding plane with the sensor cover over an entire area of the planar end surface. The peripheral edge portion has an inclined portion which is tapered so as to be inclined from the planar end surface to the lens surface of the convex surface.

According to another aspect of the present invention, there is provided an endoscope having a single lens that has a square exterior shape in the direction perpendicular to an optical axis, an image sensor that has same exterior shape as the exterior shape of the single lens in the direction perpendicular to the optical axis, a sensor cover glass that covers an imaging area of the image sensor, and has same exterior shape as the exterior shape of the single lens in the direction perpendicular to the optical axis, an objective cover glass that covers a surface on the imaging subject side of the single lens, and has same exterior shape as the exterior shape of the single lens in the direction perpendicular to the optical axis, and a bonding resin with which the sensor cover glass is fixed to the single lens, the optical axis of which coincides with a center of the imaging area. The single lens is configured to include the lens which is formed in the prismatic shape, and in which the first surface on the imaging subject side has the plane and the second surface on the imaging side has the convex surface. The central part of the single lens has the convex curved surface which protrudes in substantially the spherical shape configuring the lens surface of the convex surface on the imaging side. The peripheral edge part of the single lens has the planar end surface, and has the bonding plane with the sensor cover glass over the entire area of the end surface. The length of one side of the image sensor is 0.5 mm or smaller.

According to another aspect of the present invention, there is provided the endoscope in which the iris is disposed between the objective cover glass and the single lens.

According to another aspect of the present invention, in the endoscope, the sensor cover glass is configured to include the optical material in which the thickness SGt is 0.1 mm≤SGt≤0.5 mm and the refractive index ndR is 1.3≤ndR≤2.0.

According to another aspect of the present invention, in the endoscope, when the distance from the image forming point of the single lens on the imaging side to the end surface on the imaging subject side of the sensor cover glass in the focal length of the lens is set to x (0≤x≤f), the maximum angle of the light beam emitted to the image forming point on the imaging side from the single lens in the state of air only with respect to the optical axis is set to θair, and the maximum angle of the light beam emitted to the image forming point on the imaging side through the sensor cover glass from the single lens in the state including the sensor cover glass with respect to the optical axis is set to θgl, the single lens and the sensor cover glass have the combination of the focal length f, the F-number FNO, and the refractive index ndR, which satisfies 0.1≤x·(tan θair)/(tan θgl)≤0.5.

According to another aspect of the present invention, there is provided the endoscope in which the lighting means is disposed along the single lens, and the maximum exterior diameter of the distal portion including the single lens and the lighting means is 1.0 mm.

According to the present invention, there is provided an endoscope having a single lens that has a square exterior shape in the direction perpendicular to an optical axis, an image sensor that has same exterior shape as the exterior shape of the single lens in the direction perpendicular to the optical axis, a sensor cover glass that covers an imaging area of the image sensor, and has same exterior shape as the exterior shape of the single lens in the direction perpendicular to the optical axis, a bonding resin with which the sensor cover glass is fixed to the single lens, the optical axis of which coincides with a center of the imaging area, and a transmission cable that has the four electric cables respectively connected to the four conductor connection parts disposed in the image sensor. The length of one side of the image sensor is 0.5 mm or smaller. The four electric cables are respectively connected to the four conductor connection parts arranged at four corners on the rear end surface having the square shape of the image sensor. The central part of the single lens has the convex curved surface which protrudes in substantially the spherical shape configuring the lens surface of the convex surface on the imaging side. The peripheral edge part of the single lens has the planar end surface, and has the bonding plane with the sensor cover glass over the entire area of the end surface.

According to the present invention, there is provided an endoscope having a single lens whose exterior shape in the direction perpendicular to an optical axis is the octagonal shape in which long sides and short sides are alternately arrayed side by side, an image sensor whose exterior shape in the direction perpendicular to the optical axis is the same as the exterior shape of the single lens, a sensor cover glass that covers the imaging area of the image sensor, and whose exterior shape in the direction perpendicular to the optical axis is the same as the exterior shape of the single lens, a bonding resin with which the sensor cover glass is fixed to the single lens, the optical axis of which coincides with a center of the imaging area, and a transmission cable that has the four electric cables respectively connected to the four conductor connection parts disposed in the image sensor. The length of one side of the image sensor is 0.5 mm or smaller. The four electric cables are respectively connected to the four conductor connection parts arranged at four corners on the rear end surface having the octagonal shape of the image sensor. The central part of the single lens has the convex curved surface which protrudes in substantially the spherical shape configuring the lens surface of the convex surface on the imaging side. The peripheral edge part of the single lens has the planar end surface, and has the bonding plane with the sensor cover glass over the entire area of the end surface.

According to the present invention, there is provided an endoscope having a single lens whose exterior shape in the direction perpendicular to an optical axis is the quadrangular shape, an image sensor whose exterior shape in the direction perpendicular to the optical axis is a square shape, and in which the length of one side thereof is longer than or the same as the longest side of the single lens, and the sensor cover glass that covers the imaging area of the image sensor, and whose exterior shape in the direction perpendicular to the optical axis is the same as the exterior shape of the image sensor. The single lens in which the optical axis of the single lens is coincident with a center of the imaging area and the sensor cover glass are fixed to each other by the bonding resin. The single lens is configured to include the lens which is formed in the prismatic shape, and in which the first surface on the imaging subject side has the plane and the second surface on the imaging side has the convex surface. The central part of the single lens has the convex curved surface which protrudes in substantially the spherical shape configuring the lens surface of the convex surface on the imaging side. The peripheral edge part of the single lens has the planar end surface, and has the bonding plane with the sensor cover glass over the entire area of the end surface.

According to another aspect of the present invention, there is provided the endoscope in which the exterior shape in the direction perpendicular to the optical axis of the single lens is the square shape, and the length of one side of the exterior shape of the single lens is smaller than the length of one side of the exterior shape of the image sensor.

According to another aspect of the present invention, there is provided the endoscope in which the exterior shape in the direction perpendicular to the optical axis of the single lens is the rectangular shape.

According to the present invention, there is provided an endoscope having a single lens whose exterior shape in the direction perpendicular to an optical axis is the octagonal shape in which long sides and short sides are alternately arrayed side by side, the image sensor whose exterior shape in the direction perpendicular to the optical axis is a square shape, and in which the length of one side thereof is the same as the distance between the pair of opposing long sides of the single lens, and the sensor cover glass that covers an imaging area of the image sensor, and whose exterior shape in the direction perpendicular to the optical axis is the same as the exterior shape of the image sensor. The single lens in which the optical axis of the single lens is coincident with the center of the imaging area and the sensor cover glass are fixed to each other by the bonding resin. The single lens is configured to include the lens which is formed in the octagonal prismatic shape, and in which the first surface on the imaging subject side has the plane and the second surface on the imaging side has the convex surface. The central part of the single lens has the convex curved surface which protrudes in substantially the spherical shape configuring the lens surface of the convex surface on the imaging side. The peripheral edge part of the single lens has the planar end surface, and has the bonding plane with the sensor cover glass over the entire area of the end surface.

According to another aspect of the present invention, there is provided the endoscope in which in the exterior shape in the direction perpendicular to the optical axis, the single lens has the structure in which the short side with respect to the long side is chamfered.

The present invention provides an advantageous effect in that it is possible to achieve miniaturization and cost reduction in an endoscope. For example, the present invention is usefully applied to a small-diameter endoscope used for medical surgery.

In addition, this application is based on Japanese patent applications (Japanese Patent Application Nos. 2015-171553, 2015-171557, 2015-171558) filed on Aug. 31, 2015 and a Japanese patent application (Japanese Patent Application No. 2016-076173) filed on Apr. 5, 2016, and contents thereof are incorporated herein by reference.

What is claimed is:

1. An endoscope, comprising:
   a single lens that has a square exterior shape in a direction perpendicular to an optical axis;
   an image sensor that has an square exterior shape which is same as the exterior shape of the single lens, in the direction perpendicular to the optical axis;
   a sensor cover that covers an imaging area of the image sensor, and has an exterior shape which is same as the exterior shape of the single lens, in the direction perpendicular to the optical axis; and
   a bonding resin portion that fixes the sensor cover to the single lens, the optical axis of the single lens coinciding with a center of the imaging area,
   wherein the single lens is a lens which is formed in a prismatic shape, and whose first surface on an imaging subject side has a plane and whose second surface on an imaging side has a convex surface;
   wherein a central portion of the single lens has a convex curved surface which protrudes in a substantially spherical shape configuring a lens surface of the convex surface on the imaging side; and
   wherein a peripheral edge portion of the single lens has a planar end surface, and has a bonding plane with the sensor cover over an entire area of the planar end surface.

2. The endoscope according to claim 1, wherein the bonding plane has an exterior peripheral portion which has a square shape and an inner peripheral portion which has a substantially square shape whose corners are rounded.

3. The endoscope according to claim 2, wherein the bonding plane has an inclined portion which is tapered so as to be inclined in a direction from the inner peripheral portion to the exterior peripheral portion of the peripheral edge portion.

4. The endoscope according to claim 1, wherein the bonding plane has an exterior peripheral portion which has a square shape and an inner peripheral portion which has a circular shape concentric with the convex curved surface having a circular dome shape.

5. The endoscope according to claim 1, wherein an exterior peripheral portion of the convex curved surface having a circular dome shape has a barrel shape in which four circumferential portions corresponding to four sides of the square exterior shape of the single lens are partially notched.

6. The endoscope according to claim 5,
   wherein from the exterior peripheral portion of the convex curved surface to the inner peripheral portion of the bonding plane, the single lens has an inclined plane extending from a center of the single lens toward an exterior periphery of the single lens; and
   wherein an angle of the inclined plane is $60° \leq \theta A \leq 90°$, in case that the angle of the inclined plane is defined as an angle of an opening being set to $\theta A$ when viewed from the center of the single lens.

7. The endoscope according to claim 1, wherein the bonding plane has a bonding width of 50 μm.

8. The endoscope of claim 1, wherein the image sensor has one side whose length is 0.5 mm.

9. An endoscope, comprising:
- an image sensor that is disposed in a distal portion of an insertion portion, and whose imaging area is covered with a sensor cover;
- a single lens that has a square exterior shape in a direction perpendicular to an optical axis; and
- a bonding resin portion that fixes the single lens and the sensor cover,
- wherein the single lens is a lens which is formed in a prismatic shape, and whose first surface on an imaging subject side has a plane and whose second surface on an imaging side has a convex surface;
- wherein a central portion of the single lens has a convex curved surface which protrudes in a substantially spherical shape configuring a lens surface of the convex surface on the imaging side;
- wherein a peripheral edge portion of the single lens has a planar end surface, and has a bonding plane with the sensor cover over an entire area of the planar end surface; and
- wherein the peripheral edge portion of the single lens has an inclined portion which is tapered so as to be inclined from the planar end surface to the lens surface of the convex surface.

* * * * *